US005851991A

United States Patent [19]
Lee et al.

[11] Patent Number: 5,851,991
[45] Date of Patent: Dec. 22, 1998

[54] THERAPEUTIC USE OF THE RETINOBLASTOMA SUSCEPTIBILITY GENE PRODUCT

[75] Inventors: Wen-Hwa Lee; Eva Y-H.P. Lee, both of San Antonio; David W. Goodrich, Houston, all of Tex.; H. Michael Shepard, Rancho Santa Fe, Calif.; Nan Ping Wang, Seattle, Wash.; Duane Johnson, Encinitas, Calif.

[73] Assignees: The Regents of the University of California, Oakland; Canji, Inc., San Diego, both of Calif.

[21] Appl. No.: 306,513

[22] Filed: Sep. 13, 1994

Related U.S. Application Data

[63] Continuation-in-part of Ser. No. 121,108, Sep. 13, 1993, abandoned, Ser. No. 956,472, Oct. 2, 1992, abandoned, and Ser. No. 126,810, Sep. 24, 1993, abandoned, which is a continuation of Ser. No. 778,510, Oct. 17, 1991, abandoned, which is a continuation-in-part of Ser. No. 91,547, Aug. 31, 1987, Pat. No. 5,011,773, Ser. No. 98,612, Sep. 17, 1987, Pat. No. 4,942,123, Ser. No. 550,877, Jul. 11, 1990, abandoned, Ser. No. 553,892, Jul. 16, 1990, abandoned, Ser. No. 108,748, Oct. 15, 1987, abandoned, Ser. No. 265,829, Oct. 31, 1988, abandoned, and Ser. No. 553,905, Jul. 16, 1990, abandoned, said Ser. No. 121,108, is a continuation-in-part of Ser. No. 79,207, Jun. 17, 1993, abandoned, which is a continuation of Ser. No. 914,039, Jul. 14, 1992, abandoned, which is a continuation of Ser. No. 550,877, which is a division of Ser. No. 98,612, said Ser. No. 956,472, is a continuation of Ser. No. 553,892, which is a continuation-in-part of Ser. No. 91,547, Ser. No. 98,612, Ser. No. 108,748, Ser. No. 265,829, and Ser. No. 553,905.

[51] Int. Cl.[6] .................................................. A61K 38/17
[52] U.S. Cl. .............................. 514/12; 514/7; 530/350
[58] Field of Search ........................... 514/7, 12; 530/350

[56] References Cited

U.S. PATENT DOCUMENTS

| 4,497,796 | 2/1985 | Salser et al. | 914/44 |
|---|---|---|---|
| 4,736,866 | 4/1988 | Leder et al. | 800/2 |
| 4,783,313 | 11/1988 | Makari et al. | 424/1.57 |
| 4,803,072 | 2/1989 | Dalton et al. | 424/85.5 |
| 4,851,341 | 7/1989 | Hopp et al. | 435/69.7 |
| 4,942,123 | 7/1990 | Lee et al. | 435/7.23 |
| 5,011,773 | 4/1991 | Lee et al. | 536/23.2 |

FOREIGN PATENT DOCUMENTS

| 0259031 A2 | 8/1987 | European Pat. Off. . |
| WO 89/06703 | 7/1989 | WIPO . |
| WO 90/05180 | 5/1990 | WIPO . |
| WO 91/09114 | 6/1991 | WIPO . |

OTHER PUBLICATIONS

Madraperla et al., Cancer Res. 51:6381–6384 (1991).
Wang et al., Oncogene 8:279–288 (1993).
Lee, et al., "The retinoblastoma susceptibility gene encodes a nuclear phosphoprotein associated with DNA binding activity." *Nature* 329:642–645 (1987).
Levine, Arnold, "The Tumor Suppressor Genes." *Annu. Rev. Biochem.* 62:623–651 (1993).
Ludlow, et al., "SV40 Large T Antigen Binds Preferentially to an Underphosporylated Member of the Retinoblastoma Susceptibility Gene Product Family." *Cell* 56:57–65 (1989).

(List continued on next page.)

*Primary Examiner*—Eric Grimes
*Attorney, Agent, or Firm*—Townsend and Townsend and Crew LLP

[57] ABSTRACT

This invention provides a method of preventing or inhibiting the proliferation of a pathologically proliferating cell, wherein the pathological proliferation of the cell is the result of the absence of a functional retinoblastoma protein or polypeptide in the cell. The method requires contacting the cell with an effective amount of retinoblastoma protein or polypeptide. This method also is useful to prevent or treat retinoblastoma or a secondary cancer to retinoblastoma by administering to a patient a functional retinoblastoma protein or polypeptide.

24 Claims, 38 Drawing Sheets

OTHER PUBLICATIONS

Lundberg, et al., "Loss of heterozygosity in human ductal breast tumors indicates a recessive mutation on chromosomes 13." *Proceedings of the National Academy of Sciences* 84:2372–2376 (1987).

Mann, et al., "Construction of a Retrovirus Packaging Mutant and Its Use to Produce Helper–Free Defective Retrovirus." *Cell* 33:153–159 (1983).

Matsuura, "Baculovirus Expression Vectors: the Requirements for High Level Expression of Proteins, Including Glycoproteins." *J. Gen. Virol.* 68:1233–1250 (1987).

McCune, et al., "The SCID–hu Mouse: Murine Model for the Analysis of Human Hematolymphoid Differentiation and Function." *Science* 241: 1632–1639 (1988).

Mendoza, et al., "A Case of Synovial Sarcoma with Abnormal Expression of the Human Retinoblastoma Susceptibiltiy Gene." *Human Pathology* 19:487–489 (1988).

Mihara, et al., "Cell Cycle–Dependent Regulation of Phosphorylation of the Human Retinoblastoma Gene Product." Science 246:1300–1303 (1989).

Hooper, et al., "HPRT–deficient (Lesch–Nyhan) mouse embryos derived from germline colonization by cultured cells." *Nature* 326:292–295 (1987).

Horowitz, et al., "Frequent inactivation of the retinoblastoma anti–oncogene is restricted to a subset of human tumor cell." *Proceedings of the National Academy of Sciences* 87:2775–2779 (1990).

Horowitz, et al., "Point Mutational Inactivation of the Retinoblastoma Antioncogene." *Science* 243:937–940 (1989).

Hu, et al., "The regions of the retinoblastoma protein needed for binding to adenovirus E1A or SV40 large T antigen are common sites for mutations." *The EMBO Journal* 9(4):1147–1155 (1990).

Huang, et al., "Suppression of the Neoplastic Phenotype by Replacement of the RB Gene in Human Cancer Cells." *Science* 242:1563–66 (1988).

Huang, et al., "A cellular protein that competes with SV40 T antigen for binding to the retinoblastoma gene product." *Nature* 350:160–162 (1991).

Huang, et al., "Two distinct and frequently mutated regions of retinoblastoma protein are required for binding to SV40 T antigen." *The EMBO Journal* 9(6):1815–1822 (1990).

Hudson, et al., *Practical Immunology*, Blackwell Scientific Publications, 338–340 (1980).

Jansen, et al., "Successful Treatment of Human Acute T–Cell Leukemia in SCID Mice Using the Anti–CD7–deglycosylated Ricin A–Chain Immunotoxin DA7." *Cancer Research* 52:1314–1321 (1992).

Jeang, et al., "Abundant Synthesis of Functional Human T–Cell Leukemia Virus Type I p40$^x$ Protein in Eucaryotic Cells by Using a Baculovirus Expression Vector." *Journal of Virology* 61(3):708–713 (1987).

Kantoff, et al., "Correction of adenosine deaminase deficiency in cultured human T and B cells by retrovirus–mediated gene transfer." *Proceedings of the National Academy of Sciences* 83:6563–6567 (1986).

Kaye, et al., "A single amino acid substitution results in a retinoblastoma protein defective in phosphorylation and oncoprotein binding." *Proceedings of the National Academy of Sciences* 87:6922–6926 (1990).

Kitagawa, et al., "cdc2–like kinase is associated with the retinoblastoma protein." *Onocogene* 7:1067–1074 (1992).

Kuehn, et al., "A potential animal model for Lesch–Nyhan syndrome through introduction of HPRT mutations into mice." *Nature* 326:295–298 (1987).

LaLande, et al., "Isolation of Human Chromosome 13–Specific DNA Sequences Cloned from Flow Sorted Chromosomes and Potentially Linked to the Retinoblastoma Locus." *Cancer Genetics and Cytogenetics* 13:283–295 (1984).

LaLande, et al., "Molecular Detection and Differentiation of Deletions in Band 13q14 in Human Retinoblastoma." *Cancer Genet. Cytogenet.* 23:151–157 (1986).

Lee, Eva Y–H.P., et al., "Inactivation of the Retinoblastoma Susceptibility Gene in Human Breast Cancers." *Science* 241:218–221 (1988).

Lee, et al., "Molecular cloning of the human esterase D gene, a genetic market of retinoblastoma." *Proceedings of the National Academy of Sciences* 83:6337–6341 (1986).

Lee, et al., "Molecular mechanism of retinoblastoma gene inactivation in retinoblastoma cell line Y79." *Proceedings of the National Academy of Sciences* 85:6017–6021 (1988).

Lee, et al., "Human Retinoblastoma Susceptibility Gene: Cloning, Identification and Sequence." *Science* 235:1394–1399 (1987).

Lee, et al., "Purification, biochemical characterization, and biological function of human esterase D." *Proceedings of the National Academy of Sciences* 83:6790–6794 (1986).

Miller, et al., "Generation of Helper–Free Amphotropic Retroviruses That Transduce a Dominant–Acting, Methotrexate–Resistant Dihydrofolate Reductase Gene." *Mol. Cell. Biol.* 5(3):431–437 (1985).

Miller, et al., "Transfer of Genes into Human Somatic Cells Using Retrovirus Vectors." *Cold Spring Harbor Symposia on Quantitative Biology* LI:1013–1019 (1986).

Miller, et al., "A transmissible retrovirus expressing human hypoxanthine phosphoribosyltransferase (HPRT): Gene transfer into cells obtained from humans deficient in HPRT." *Proceedings of the National Academy of Sciences USA* 80:4709–4713 (1983).

Miyamoto, et al., "Production of Human c–myc Protein in Insect Cells Infected with a Baculovirus Expression Vector." *Molecular and Cell Biology* 5(10): 2860–2865 (1985).

Mosier, et al., "Transfer of a functional human immune system to mice with severe combined immnodeficiency." *Nature* 335:256–259 (1988).

Murphree, A. Linn and Benedict, William F., "Retinoblastoma: Clues to Human Oncogenesis." *Science* 223:1028–1033 (1984).

Pendergast, et al., "Baculovirus expression of functional P210 BCR–ABL oncogene product." *Oncogene* 4:759–766 (1989).

Ramsay, et al., "Human Proto–Oncogene N–myc Encodes Proteins That Bind DNA." *Molecular and Cellular Biology* 6(12):4450–4457 (1986).

Ratajczak, et al., "In vivo treatment of human leukemia in a scid mouse model with c–myb antisense oligodeoxynucleotides." *Proceedings of the National Academy of Sciences* 89:11823–11827 (1992).

Reissmann, et al., "Inactivation of the retinoblastoma susceptibility gene in non–small–cell lung cancer." *Oncogene* 8:1913–1919 (1993).

Sachse, et al., "DNA aberrations at the retinoblastoma gene locus in human squamous cells carcinomas of the lung." *Oncogene* 9:39–47 (1994).

Eliyahu, et al., "Wild–type p53 can inhibit oncogene–mediated focus formation." *Proceedings of the National Academy of Sciences* 86:8763–8767 (1989).

Friedmann, Theodore, "Gene Therapy of Cancer through Restoration of Tumor–Suppressor Functions?" *Cancer* 70:1810–1817 (1992).

Friedmann, Theodore, "Progress Toward Human Gene Therapy." *Science* 244:1275–1281 (1989).

Friend, et al., "Deletions of a DNA sequence in retinoblastomas and mesenchymal tumors: Organization of the sequence and its encoded protein." *Proceedings of the National Academy of Sciences* 84:9059–9063 (1987).

Friend, et al., "A human DNA segment with properties of the gene that predisposes to retinoblastoma and osteosarcoma." *Nature* 323:643–646 (1986).

Fung, et al., "Structural Evidence for the Authenticity of the Human Retinoblastoma Gene." *Science* 236:1657–1661 (1987).

Funk, Sarah E. and Sage, E. Helene, "The $Ca^{2+}$–binding glycoprotein SPARC modulates cell cycle progression in bovine aortic endothelial cells." *Proceedings of the National Academy of Sciences* 88:2648–2652 (1991).

Gishizky, et al., "Efficient transplantation of BCR–ABL–induced chronic myelogenous leukemia–like syndrome in mice." *Proceedings of the National Academy of Sciences* 90–3755–3759 (1993).

Gluzman, Yakov, "SV40–Transformed Simian Cells Support the Replication of Early SV40 Mutants." *Cell* 23:175–182 (1981).

Thomas, Kirk R. and Capecchi, Mario R., "Site–Directed Mutagenesis by Gene Targeting in Mouse Embryo–Derived Stem Cells." *Cells* 51:503–512 (1987).

Toguchida, et al., "Chromosomal Reorganization for the Expression of Recessive Mutation of Retinoblastoma Susceptibility Gene in the Development of Osterosarcoma" *Cancer Research* 48:3939–3943 (1988).

Wang, et al., "Expression of the Human Retinoblastoma Gene Product pp110$^{RB}$ in Insect Cells Using the Baculovirus System." *Cell Growth & Differ.* 1:429–437 (1990).

Ward, et al., "Location of the retinoblastoma susceptibility gene(s) and the human esterase D locus." *Journal of Medical Genetics* 21:92–95 (1984).

Weissman, et al., "Introduction of a Normal Human Chromosome 11 into a Wilms' Tumor Cell Line Controls Its Tumorigenic Expression." *Science* 236:175–180 (1987).

Whyte, et al., "Association between an oncogene and an anti–oncogene: the adenovirus E1A proteins bind to the retinoblastoma gene product." *Nature* 334:124–129 (1988).

Yokota, et al., "Altered expression of the retinoblastoma (RB) gene in small–cell carcinoma of the lung." *Oncogene* 3:471–475 (1988).

Yunis, J., and Ramsay, N., "Retinoblastoma and Subband Deletion of Chromosome 13." *Am J Dis Child* 132:161–163, (1978).

Sager, Ruth, "Tumor Suppressor Genes: The Puzzle and the Promise." *Science* 246:1406–1412 (1989).

Schneider, et al., "A One–step Purification of Membrane Proteins Using a High Efficiency Immunomatrix." *J. Biol. Chem.* 257(18):10766–10769 (1982).

Shew, et al., "Antibodies Detecting Abnormalities of the Retinoblastoma Susceptibility Gene Product (pp110 $^{RB}$) in Osteosarcomas and Synovial Sarcomas." *Oncogene Research* 1:205–214 (1989).

Shew, et al., "C–terminal truncation of the retinoblastoma gene product leads to functional inactivation." *Proceedings of the National Academy of Sciences* 87:6–10 (1990).

Simanis, V., and Lane, D.P., "An Immunoaffinity Purification Procedure for SV40 Large T Antigen." *Virology* 144:88–100 (1985).

Smith, G.E., et al., "Production of Human Beta Interferon in Insect Cells Infected with a Baculovirus Expression Vector." *Mol. Cell. Biol.* 3(12):2156–2165 (1983).

Strong, et al., "Familial Retinoblastoma and Chromosome 13 Deletion Transmitted via an Insertional Translocation." *Science* 213:1501–1503 (1981).

Takahashi, et al., "The retinoblastoma gene functions as a growth and tumor suppressor in human bladder carcinoma cells." *Proceedings of the National Academy of Sciences* 88:5257–5261 (1991).

Tertoolen, et al., "Electrophysiological responses to bradykinin and microinjected inositol polyphosphates in neuroblastoma cells." *FEBS Lett.* 214:365–369 (1987).

Thomas, et al., "High Frequency Targeting of Genes to Specific Sites in the Mammalian Genome." *Cell* 44:419–428 (1986).

Angier, N., "Light Cast on a Darkling Gene." *Discover* Mar.:85–96 (1987).

Bender, et al., "Chromosomal Walking and Jumping to Isolate DNA from the Ace and rosy Loci and the Bithorax Complex in *Drosophila melanogaster.*" *J. Mol. Biol.* 168:17–33 (1983).

Benedict, et al., "Nonrandom Chromosomal Changes in Untreated Retinoblastomas." *Cancer Genet. and Cytogenet.* 10:311–333 (1983).

Benedict, et al., "Patient with 13 Chromosome Deletion Evidence that the Retinoblastoma Gene Is a Recessive Cancer Gene." *Science* 219:973–975 (1983).

Bignon, et al., "Expression of a retinoblastoma transgene results in dwarf mice." *Genes & Development* 7:1654–1662 (1993).

Bookstein, et al., "Human retinoblastoma susceptibility gene: Genomic organization and analysis of heterozygous intragenic deletion mutants." *Proceedings of the National Academy of Sciences* 85:2210–2214 (1988).

Bookstein, et al., "Suppression of Tumorigenicity of Human Prostate Carcinoma Cells by Replacing a Mutated RB Gene." *Science* 247:712–715 (1990).

Bowen, et al., "The detection of DNA–binding proteins by protein blotting." *Nucleic Acids Research* 8:1–20 (1980).

Buchkovich, et al., "The Retinoblastoma Protein Is Phosphorylated during Specific Phases of the Cell Cycle." *Cell* 58:1097–1105 (1989).

Capecchi, Mario R, "Altering the Genome by Homologous Recombination." *Science* 244:1288–1292 (1989).

Cavenee, et al., "Expression of recessive alleles by chromosomal mechanisms in retinoblastoma." *Nature* 305:779–783 (1983).

Cavenee, et al., "Isolation and Regional Localization of DNA Segments Revealing Polymorphic Loci from Human Chromosome 13." *Am. J. Hum. Genet.* 36:10–24 (1984).

Cepko, et al., "Construction and Applications of a Highly Transmissible Murine Retrovirus Shuttle Vector." *Cell* 37:1053–1062 (1984).

Chen, et al., "Phosphorylation of the Retinoblastoma Gene Product Is Modulated during the Cell Cycle and Cellular Differentiation." *Cell* 58:1193–1198 (1989).

Cooper, Geoffrey M. "Tumor Suppressor Genes." *Oncogenes,* 121–139 (1990).

Cooper, J.A. and Whyte, Peter, "RB and the Cell Cycle: Entrance or Exit?" Cell 58:1009–1011 (1989).

Cordaro, J.C., "Transgenic Mice as Future Tools in Risk Assessment." *Risk Analysis* 9(2):157–168 (1989).

Cordon–Cardo, et al., "Altered Expression of the Retinoblastoma Gene Product: Prognostic Indicator in Bladder Cancer." *J. Natl. Cancer Inst.* 84(16):1251–1256 (1992).

DeCaprio, et al., "The Product of the Retinoblastoma Susceptibility Gene Has Properties of a Cell Cycle Regulatory Element." *Cell* 58:1085–1095 (1989).

DeCaprio, et al., "SV40 Large Tumor Antigen Forms a Specific Complex with the Product of the Retinoblastoma Susceptibiltiy Gene." *Cell* 54:275–283 (1988).

Dixon, Richard A. and Nathans, Daniel, "Purification of Simian Virus 40 Large T Antigen by Immunoaffinity Chromatography." *Journal of Virology* 53:1001–1004 (1985).

Goodrich, D.W. and Lee, Wen–Hwa, "Molecular characterization of the retinoblastoma susceptibility gene." *Biochimica et Biophysica Acta* 1155:43–61 (1993).

Goodrich, et al., "The Retinoblastoma Gene Product Regulates Progression through the G1 Phase of the Cell Cycle." *Cell* 67:293–302 (1991).

Gossler, et al., "Transgenesis by means of blastocyst–derived embryonic stem cell lines." *Proceedings of the National Academy of Sciences* 83:9065–9096 (1986).

Gu, et al., "Interaction of Myogenic Factors and the Retinoblastoma Protein Mediates Muscles Cell Commitment and Differentiation." *Cell* 72:309–324 (1993).

Harbour, et al., "Abnormalities in Structure and Expression of the Human Retinoblastoma Gene in SCLC." *Science* 241:353–256 (1988).

Harris, Henry, "Malignant tumours generated by recessive mutations." *Nature* 323:582–583 (1986).

Helin, et al., "A cDNA Encoding a pRB–Binding Protein with Properties of the Transcription Factor E2F." *Cell* 70:337–350 (1992).

Hird, V. and Epenetos, A.A., "Immunotherapy with Monoclonal Antibodies." *Genes and Cancer*, John Wiley & Sons, New York, NY, 183–189 (1990).

Hong, et al., "Structure of the human retinoblastoma gene." *Proceedings of the National Academy of Sciences* 86:5502–5506 (1989).

Doerfler, W., "Expression of the *Autographa californica* Nuclear Polyhedrosia Virus Genome in Insect Cells: Homologous Viral and Heterologous Vertebrate Genes—The Baculovirus Vector System." *Current Topics in Microl. Immunol.* 131:51–68 (1986).

Donner, et al., "Nuclear localization and DNA binding of the transforming gene product of avian myelocytomatosis virus." *Nature* 296:262–266 (1982).

Dryja, et al., "Chromosome 13 Homozygosity in Osteosarcoma without Retinoblastoma." *Am. J. Hum Genet.* 38:59–66 (1986).

Dryja, et al., "Genetic Sequences That Predispose to Retinoblastoma and Osteosarcoma." *Symposium on Fundamental Cancer Research* 39:115–119 (1987).

Dryja, et al., "Molecular detection of deletions involving band q14 of chromosome 13 in retinoblastomas." *Proceedings of the National Academy of Sciences* 83:7391–7394 (1986).

Dyson, et al., "The Human Papilloma Virus–16 E7 Oncoprotein Is Able to Bind to the Retinoblastoma Gene Product." Science 243:934–937 (1989).

Edwards, et al., "Purification and Characterization of a Functionally Homogenous 60–kDa Species of the Retinoblastomas Gene Product" *The Journal of Biological Chemistry* 267(12):7971–7974 (1992).

Xu et al., Proc. Natl. Acad. Sci. USA 91:9837–9841 1994.

```
TTCCGGTTTT TCTCAGGGGA CGTTGAAATT ATTTTTGTAA CGGGAGTCGG GAGAGGACGG         60

GGCGTGCCCC GCGTGCGCGC GCGTGCGTCC CCCCGGCGCT CCTCCACAGC TCGCTGGCTC        120

CCGCCGCGGA AAGGCGTC ATG CCG CCC AAA ACC CCC CGA AAA ACG GCC GCC         171
              Met Pro Pro Lys Thr Pro Arg Lys Thr Ala Ala
                1                 5                  10

ACC GCC GCT GCC GCC GCG GAA CCC CCG GCA CCG CCG CCG CCC                   219
Thr Ala Ala Ala Ala Ala Glu Pro Pro Ala Pro Pro Pro Pro
           15                  20                  25

CCT CCG TAG GAG GAC CCA GAG CAG GAC AGC GGC CCG GAG GAC CTG CCT           267
Pro Pro Glu Glu Asp Pro Glu Gln Asp Ser Gly Pro Glu Asp Leu Pro
               30                  35                  40

CTC GTC AGG CTT GAG TTT GAA GAA ACA GAA GAA CCT GAT TTT ACT GCA           315
Leu Val Arg Leu Glu Phe Glu Glu Thr Glu Glu Pro Asp Phe Thr Ala
       45                  50                  55

TTA TGT CAG AAA TTA AAG ATA CCA GAT CAT GTC AGA GAG AGA GCT TGG           363
Leu Cys Gln Lys Leu Lys Ile Pro Asp His Val Arg Glu Arg Ala Trp
  60                  65                  70                  75
```

FIG.2A

```
TTA ACT TGG GAG AAA GTT TCA TCT GTG GAT GGA GTA TTG GGA GGT TAT    411
Leu Thr Trp Glu Lys Val Ser Ser Val Asp Gly Val Leu Gly Gly Tyr
            80                      85                      90

ATT CAA AAG AAA AAG GAA CTG TGG GGA ATC TGT ATC TTT ATT GCA GCA    459
Ile Gln Lys Lys Lys Glu Leu Trp Gly Ile Cys Ile Phe Ile Ala Ala
            95                     100                     105

GTT GAC CTA GAT GAG ATG TCG TTC ACT TTT ACT GAG CTA CAG AAA AAC    507
Val Asp Leu Asp Glu Met Ser Phe Thr Phe Thr Glu Leu Gln Lys Asn
           110                     115                     120

ATA GAA ATC AGT GTC CAT AAA TTC TTT AAC TTA CTA AAA GAA ATT GAT    555
Ile Glu Ile Ser Val His Lys Phe Phe Asn Leu Leu Lys Glu Ile Asp
           125                     130                     135

ACC AGT ACC AAA GTT GAT AAT GCT ATG TCA AGA CTG TTG AAG AAG TAT    603
Thr Ser Thr Lys Val Asp Asn Ala Met Ser Arg Leu Leu Lys Lys Tyr
           140                     145                     150                     155

GAT GTA TTG TTT GCA CTC TTC AGC AAA TTG GAA AGG ACA TGT GAA CTT    651
Asp Val Leu Phe Ala Leu Phe Ser Lys Leu Glu Arg Thr Cys Glu Leu
           160                     165                     170
```

FIG.2B

```
ATA TAT TTG ACA CAA CCC AGC AGT TCG ATA TCT ACT GAA ATA AAT TCT    699
Ile Tyr Leu Thr Gln Pro Ser Ser Ser Ile Ser Thr Glu Ile Asn Ser
            175                 180                 185

GCA TTG GTG CTA AAA GTT TCT TGG ATC ACA TTT TTA TTA GCT AAA GGG    747
Ala Leu Val Leu Lys Val Ser Trp Ile Thr Phe Leu Leu Ala Lys Gly
            190                 195                 200

GAA GTA TTA CAA ATG GAA GAT CTG GTG ATT TCA TTT CAG TTA ATG        795
Glu Val Leu Gln Met Glu Asp Leu Val Ile Ser Phe Gln Leu Met
            205                 210                 215

CTA TGT GTC CTT GAC TAT TTT ATT AAA CTC TCA CCT CCC ATG TTG CTC    843
Leu Cys Val Leu Asp Tyr Phe Ile Lys Leu Ser Pro Pro Met Leu Leu
            220                 225                 230      235

AAA GAA CCA TAT AAA ACA GCT GTT ATA CCC ATT AAT GGT TCA CCT CGA    891
Lys Glu Pro Tyr Lys Thr Ala Val Ile Pro Ile Asn Gly Ser Pro Arg
            240                 245                 250

ACA CCC AGG CGA GGT CAG AAC AGG AGT GCA CGG ATA GCA AAA CAA CTA    939
Thr Pro Arg Arg Gly Gln Asn Arg Ser Ala Arg Ile Ala Lys Gln Leu
            255                 260                 265
            Rb 49
```

FIG.2C

```
GAA AAT GAT ACA AGA ATT ATT GAA GTT CTC TGT AAA GAA CAT GAA TGT      987
Glu Asn Asp Thr Arg Ile Ile Glu Val Leu Cys Lys Glu His Glu Cys
                270                 275                 280

AAT ATA GAT GAG GTG AAA AAT GTT TAT TTC AAA AAT TTT ATA CCT TTT     1035
Asn Ile Asp Glu Val Lys Asn Val Tyr Phe Lys Asn Phe Ile Pro Phe
            285                 290                 295

ATG AAT TCT CTT GGA CTT GTA ACA TCT AAT GGA CTT CCA GAG GTT GAA     1083
Met Asn Ser Leu Gly Leu Val Thr Ser Asn Gly Leu Pro Glu Val Glu
300                 305                 310                 315

AAT CTT TCT AAA CGA TAC GAA GAA ATT TAT CTT AAA AAT AAA GAT CTA     1131
Asn Leu Ser Lys Arg Tyr Glu Glu Ile Tyr Leu Lys Asn Lys Asp Leu
                320                 325                 330

GAT GCA AGA TTA TTT TTG GAT CAT GAT AAA ACT CTT ACT GAT TCT         1179
Asp Ala Arg Leu Phe Leu Asp His Asp Lys Thr Leu Thr Asp Ser
            335                 340                 345

ATA GAC AGT TTT GAA ACA CAG AGA ACA CCA CGA AAA AGT AAC CTT GAT     1227
Ile Asp Ser Phe Glu Thr Gln Arg Thr Pro Arg Lys Ser Asn Leu Asp
350                 355                 360
```

FIG.2D

```
GAA GAG GTG AAT GTA ATT CCT CCA CAC ACT CCA GTT AGG ACT GTT ATG    1275
Glu Glu Val Asn Val Ile Pro Pro His Thr Pro Val Arg Thr Val Met
365                         370                         375    ↑
                                                                A

AAC ACT ATC CAA CAA TTA ATG ATG ATT TTA AAT TCA GCA AGT GAT CAA    1323
Asn Thr Ile Gln Gln Leu Met Met Ile Leu Asn Ser Ala Ser Asp Gln
380                         385                         390                395

CCT TCA GAA AAT CTG ATT TCC TAT TTT AAC AAC TGC ACA GTG AAT CCA    1371
Pro Ser Glu Asn Leu Ile Ser Tyr Phe Asn Asn Cys Thr Val Asn Pro
            400                         405                         410

AAA GAA AGT ATA CTG AAA AGA GTG AAG GAT ATA GGA TAC ATC TTT AAA    1419
Lys Glu Ser Ile Leu Lys Arg Val Lys Asp Ile Gly Tyr Ile Phe Lys
            415                         420                         425

GAG AAA TTT GCT AAA GCT GTG GGA CAG GGT TGT GTC GAA ATT GGA TCA    1467
Glu Lys Phe Ala Lys Ala Val Gly Gln Gly Cys Val Glu Ile Gly Ser
430                         435                         440
```

FIG.2E

```
CAG CGA TAC AAA CTT GGA GTT CGC TTG TAT TAC CGA GTA ATG GAA TCC    1515
Gln Arg Tyr Lys Leu Gly Val Arg Leu Tyr Tyr Arg Val Met Glu Ser
445                 450                 455

ATG CTT AAA TCA GAA GAA CGA TTA TCC ATT CAA AAT TTT AGC AAA        1563
Met Leu Lys Ser Glu Glu Arg Leu Ser Ile Gln Asn Phe Ser Lys
    460                 465                 470             475

CTT CTG AAT GAC AAC ATT TTT CAT ATG TCT TTA TTG GCG TGC GCT CTT    1611
Leu Leu Asn Asp Asn Ile Phe His Met Ser Leu Leu Ala Cys Ala Leu
            480                 485                 490

GAG GTT GTA ATG GCC ACA TAT AGC AGA AGT ACA TCT CAG AAT CTT GAT    1659
Glu Val Val Met Ala Thr Tyr Ser Arg Ser Thr Ser Gln Asn Leu Asp
                495                 500                 505

TCT GGA ACA GAT TTG TCT TTC CCA TGG ATT CTG AAT GTG CTT AAT TTA    1707
Ser Gly Thr Asp Leu Ser Phe Pro Trp Ile Leu Asn Val Leu Asn Leu
        510                 515                 520
```

FIG.2F

```
AAA GCC TTT GAT TTT TAC AAA GTG ATC GAA AGT TTT ATC AAA GCA GAA   1755
Lys Ala Phe Asp Phe Tyr Lys Val Ile Glu Ser Phe Ile Lys Ala Glu
525                 530                 535

GGC AAC TTG ACA AGA GAA ATG ATA AAA CAT TTA GAA CGA TGT GAA CAT   1803
Gly Asn Leu Thr Arg Glu Met Ile Lys His Leu Glu Arg Cys Glu His
540                 545                 550                 555

CGA ATC ATG GAA TCC CTT GCA TGG CTC TCA CCT TTA TTT GAT           1851
Arg Ile Met Glu Ser Leu Ala Trp Leu Ser Pro Leu Phe Asp
560                 565                 570

CTT ATT AAA CAA TCA AAG GAC CGA GAA GGA CCA ACT GAT CAC CTT GAA   1899
Leu Ile Lys Gln Ser Lys Asp Arg Glu Gly Pro Thr Asp His Leu Glu
575                 580                 585

TCT GCT TGT CCT CTT AAT CTT CCT CTC CAG AAT CAC AAT CAC ACT GCA GCA   1947
Ser Ala Cys Pro Leu Asn Leu Pro Leu Gln Asn His Asn His Thr Ala Ala
590                 595                 600

GAT ATG TAT CTT TCT CCT GTA AGA TCT CCA AAG AAA GGT TCA ACT       1995
Asp Met Tyr Leu Ser Pro Val Arg Ser Pro Lys Lys Gly Ser Thr
605                 610                 615
```

FIG.2G

```
ACG CGT GTA AAT TCT ACT GCA AAT GCA GAG ACA CAA GCA ACC TCA GCC    2043
Thr Arg Val Asn Ser Thr Ala Asn Ala Glu Thr Gln Ala Thr Ser Ala
620                     625                 630                 635

TTC CAG ACC CAG AAG CCA TTG AAA TCT ACC TCT CTT TCA CTG TTT TAT    2091
Phe Gln Thr Gln Lys Pro Leu Lys Ser Thr Ser Leu Ser Leu Phe Tyr
                640                 645                 650

AAA AAA GTG TAT CGG CTA GCC TAT CTC CGG CTA AAT ACA CTT TGT GAA    2139
Lys Lys Val Tyr Arg Leu Ala Tyr Leu Arg Leu Asn Thr Leu Cys Glu
        655                 660                 665

CGC CTT CTG TCT GAG CAC CCA GAA TTA GAA CAT ATC ATC TGG ACC CTT    2187
Arg Leu Leu Ser Glu His Pro Glu Leu Glu His Ile Ile Trp Thr Leu
670                 675                 680

TTC CAG CAC ACC CTG CAG AAT GAG TAT GAA CTC ATG AGA GAC AGG CAT    2235
Phe Gln His Thr Leu Gln Asn Glu Tyr Glu Leu Met Arg Asp Arg His
        685                 690                 695
```

FIG.2H

```
TTG GAC CAA ATT ATG ATG TGT TCC ATG TAT GGC ATA TGC AAA GTG AAG    2283
Leu Asp Gln Ile Met Met Cys Ser Met Tyr Gly Ile Cys Lys Val Lys
700                 705                 710                 715

AAT ATA GAC CTT AAA TTC AAA ATC ATT GTA ACA GCA TAC AAG GAT CTT    2331
Asn Ile Asp Leu Lys Phe Lys Ile Ile Val Thr Ala Tyr Lys Asp Leu
            720                 725                 730

CCT CAT GCT GTT CAG GAG ACA TTC AAA CGT GTT TTG ATC AAA GAA GAG    2379
Pro His Ala Val Gln Glu Thr Phe Lys Arg Val Leu Ile Lys Glu Glu
        735                 740                 745

GAG TAT GAT TCT ATT ATA GTA TTC ATA GTA TTC TAT AAC TCG GTC TTC ATG CAG AGA    2427
Glu Tyr Asp Ser Ile Ile Val Phe Tyr Asn Ser Val Phe Met Gln Arg
    750                 755                 760

CTG AAA ACA AAT ATT TTG CAG TAT GCT TCC ACC AGG CCC CCT ACC TTG    2475
Leu Lys Thr Asn Ile Leu Gln Tyr Ala Ser Thr Arg Pro Pro Thr Leu
765                 770                 775
```

FIG. 2I

```
TCA CCA ATA CCT CAC ATT CCT CGA AGC CCT TAC AAG TTT CCT AGT TCA   2523
Ser Pro Ile Pro His Ile Pro Arg Ser Pro Tyr Lys Phe Pro Ser Ser
780                 785                 790                 795

CCC TTA CGG ATT CCT GGA GGG AAC ATC TAT ATT TCA CCC CTG AAG AGT   2571
Pro Leu Arg Ile Pro Gly Gly Asn Ile Tyr Ile Ser Pro Leu Lys Ser
800                 805                 810

CCA TAT AAA ATT TCA GAA GGT CTG CCA ACA CCA ACA AAA ATG ACT CCA   2619
Pro Tyr Lys Ile Ser Glu Gly Leu Pro Thr Pro Thr Lys Met Thr Pro
        815                 820                 825

AGA TCA AGA ATC TTA GTA TCA ATT GGT GAA TCA TTC GGG ACT TCT GAG   2667
Arg Ser Arg Ile Leu Val Ser Ile Gly Glu Ser Phe Gly Thr Ser Glu
830                 835                 840

AAG TTC CAG AAA ATA AAT CAG ATG GTA TGT AAC AGC GAC CGT GTG CTC   2715
Lys Phe Gln Lys Ile Asn Gln Met Val Cys Asn Ser Asp Arg Val Leu
845                 850                 855

AAA AGA AGT GCT GAA GGA AGC AAC CCT CCT AAA CCA CTG AAA AAA CTA   2763
Lys Arg Ser Ala Glu Gly Ser Asn Pro Pro Lys Pro Leu Lys Lys Leu
860                 865                 870                 875
```

FIG.2J

```
CGC TTT GAT ATT GAA GGA TCA GAT GAA GCA GAT GGA AGT AAA CAT CTC    2811
Arg Phe Asp Ile Glu Gly Ser Asp Glu Ala Asp Gly Ser Lys His Leu
                880                 885                 890

CCA GAG TCC AAA TTT CAG CAG AAA CTG GCA GAA ATG ACT TCT ACT        2859
Pro Gly Glu Ser Lys Phe Gln Gln Lys Leu Ala Glu Met Thr Ser Thr
                895                 900                 905

CGA ACA CGA ATG CAA AAG CAG AAA ATG AAT GAT AGC ATG GAT ACC TCA    2907
Arg Thr Arg Met Gln Lys Gln Lys Met Asn Asp Ser Met Asp Thr Ser
                910                 915   ↑             920
                                           C

AAC AAG GAG AAA GAG AAA TGAGGATCTC AGGACCTTGG TGGACACTGT GTACACCTCT   2962
Asn Lys Glu Lys Glu Lys
                925  ↑
                     B

GGATTCATTG TCTCTCACAG ATGTGACTGA TAT                                 2995
```

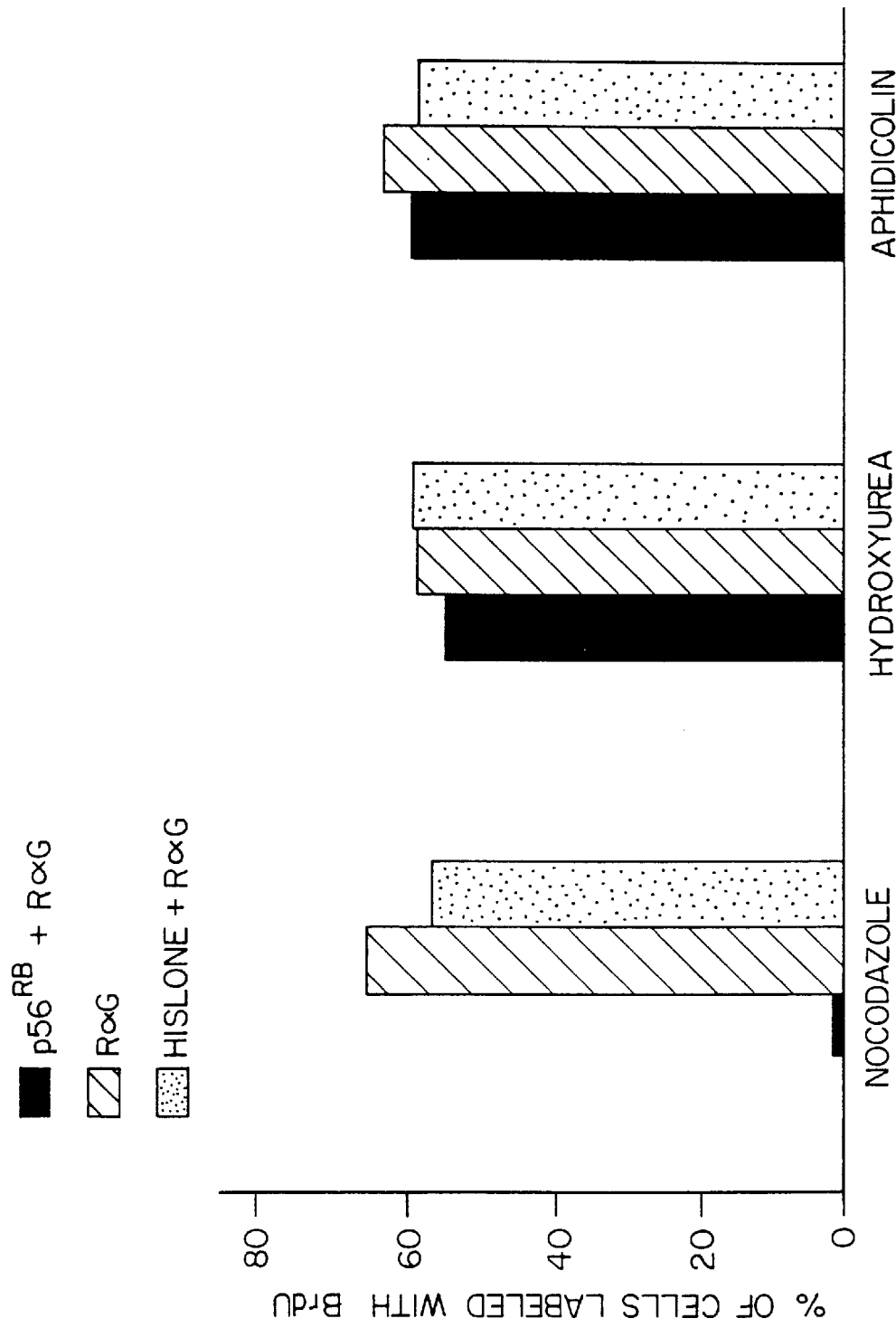

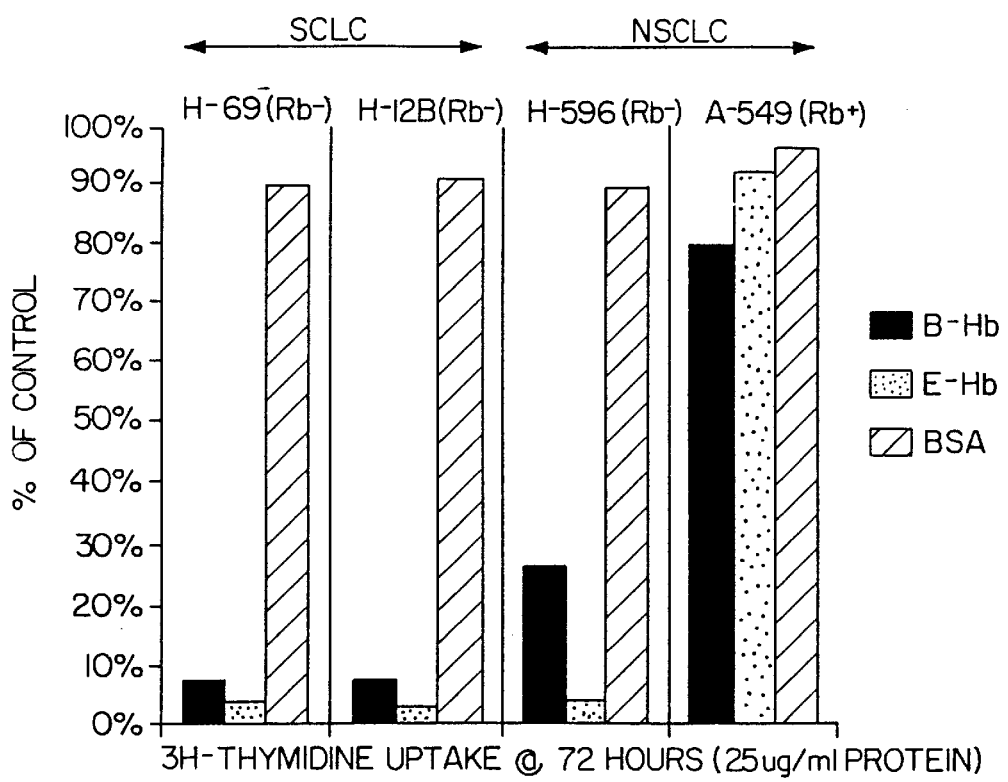
FIG. 25
FIG. 26
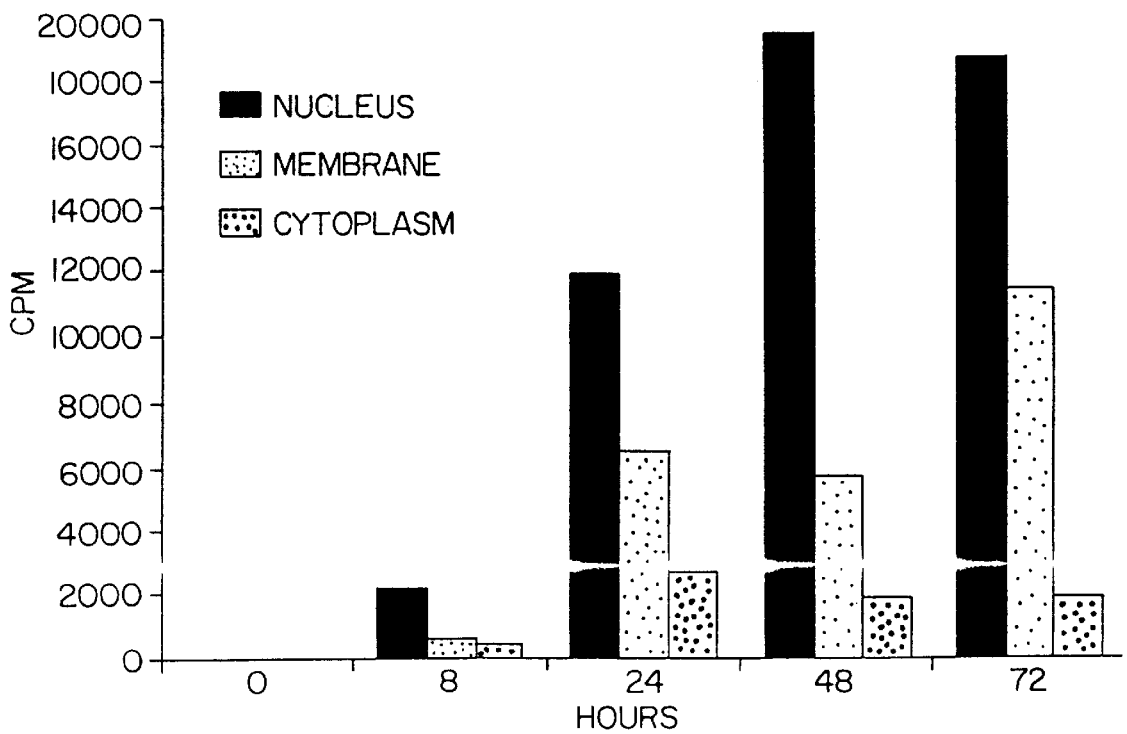

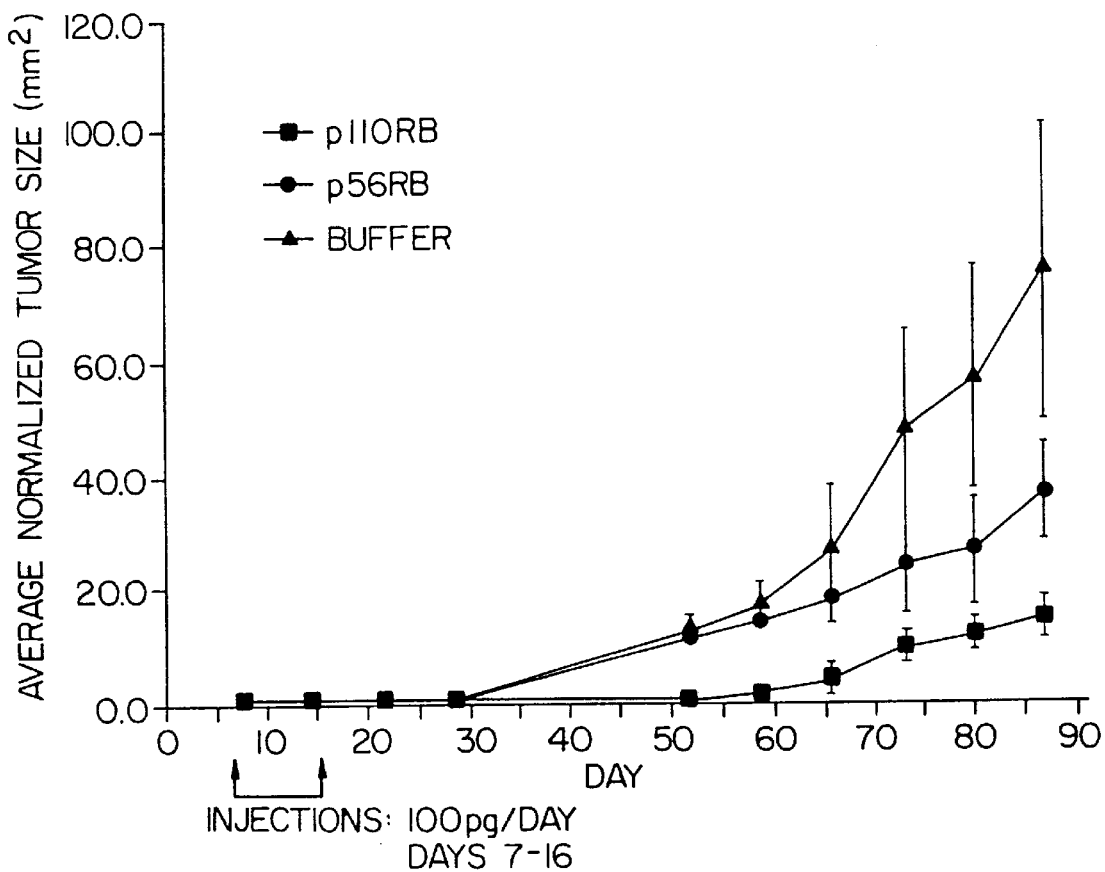
FIG. 28
FIG. 29
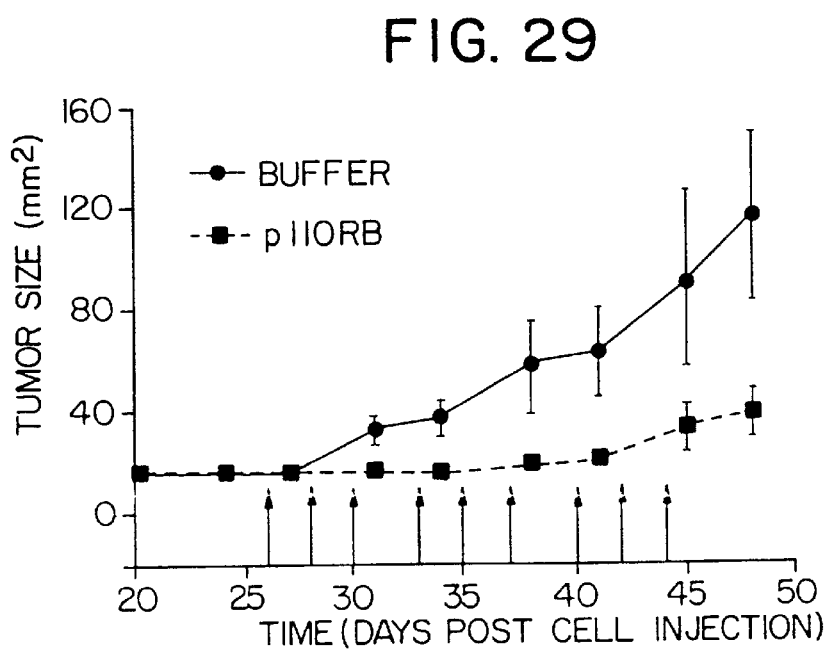

DNASIS
RE PROTEIN SEQ

Rb bacterial amino acid sequence

```
         10         20         30         40         50         60
  MAPKTPRKTA ATAAAAAAEP PAPPPPPPPE EDPEQDSGPE DLPLVRLEFE ETEEPDFTAL
         70         80         90        100        110        120
  CQKLKIPDHV RERAWLTWEK VSSVDGVLGG YIQKKKELWG ICIFIAAVDL DEMSFTFTEL
        130        140        150        160        170        180
  QKNIEISVHK FFNLLKEIDT STKVDNAMSR LLKKYDVLFA LFSKLERTCE LIYLTQPSSS
        190        200        210        220        230        240
  ISTEINSALV LKVSWITFLL AKGEVLQMED DLVISFQLML CVLDYFIKLS PPMLLKEPYK
        250        260        270        280        290        300
  TAVIPINGSP RTPRRGQNRS ARIAKQLEND TRIIEVLCKE HECNILEVKN VYFKNFIPFM
        310        320        330        340        350        360
  NSLGLVTSNG LPEVENLSKR YEETYLKNKD LDARLFLDHD KTLQTDSIDS FETQRTPRKS
        370        380        390        400        410        420
  NLDEEVNVIP PHTPVRTVMN TIQQLMMILN SASDQPSENL ISYFNNCTVN PKESILKRVK
        430        440        450        460        470        480
  DIGYIFKEKF AKAVGQGCVE IGSQKYKLGV FLYYRVMESM LKSRRRRLSI QNFSKLLNIN
        490        500        510        520        530        540
  IFHMSLLACA LEVVMATYSR STSQNLDSGT DLSFPWILNV LNLKAFDFYK VIESFIKAEG
        550        560        570        580        590        600
  MLTREMIKHL ERCEHRIMES LAWLSDSPLF DLIKQSKDRE GPTDHLESAC PLNLPLQNNH
        610        620        630        640        650        660
  TAADMYLSPV RSPKKKGSTT RVNSTANAET QATSAFQTQK PLKSTSLSLF YKKBYRLAYL
        670        680        690        700        710        720
  RLNTLCERLL SEHPELEHII WTLFUHTLQN EYELMRDRHL DQIMMCSMYG ICKVKNIDLK
        730        740        750        760        770        780
  FKIIVTAYKD LPHAVQETFK RVLIKEEEYD SIIVFYNSVF MQRLKTNILQ YASTRPPTLS
        790        800        810        820        830        840
  PIPHIPRSPY KFPSSPLRIP GGNIYISPLK SPYKISEGLP TPTKMTPRSR ILVSIGESFG
        850        860        870        880        890        900
  TSEKFQKINQ MVCNSDRVLK RSAEGSNPPK PLKKLRFDIE GSDEADGSKH LPGESKFQQK
        910        920        930        940        950        960
  LAEMTSTRTR MQKQKMNDSM DSTNKEEK.. .......... .......... ..........
```

FIG. 30

THERAPEUTIC USE OF THE RETINOBLASTOMA SUSCEPTIBILITY GENE PRODUCT

This application is a continuation-in-part of U.S. Ser. No. 121,108, filed Sep. 13, 1993, now abandoned, which in turn is a continuation-in-part of U.S. Ser. No. 079,207, filed Jun. 17, 1993, now abandoned, which is a continuation of U.S. Ser. No. 914,039, filed Jul. 14, 1992, now abandoned, which is a continuation of U.S. Ser. No. 550,877, filed Jul. 11, 1990, now abandoned, which is a divisional of U.S. Ser. No. 098,612, filed Sep. 17, 1987, now U.S. Pat. No. 4,942,123, issued Jul. 17, 1990, the disclosures of which are hereby incorporated by reference.

This application also is a continuation-in-part of U.S. Ser. No. 956,472, filed Oct. 2, 1992, now abandoned, which in a continuation application of U.S. Ser. No. 553,892, filed Jul. 16, 1990, now abandoned, which in turn is a continuation-in-part application of each of U.S. Ser. No. 091,547, filed Aug. 31, 1987, now U.S. Pat. No. 5,011,773, issued Apr. 30, 1991; U.S. Ser. No. 098,612, filed Sep. 17, 1987, now U.S. Pat. No. 4,942,123, issued Jul. 17, 1990; U.S. Ser. No. 108,748, filed Oct. 15, 1987, now abandoned; U.S. Ser. No. 265,829, filed Oct. 31, 1988, now abandoned; and U.S. Ser. No. 553,905,; filed Jul. 16, 1990, now abandoned. The contents of each of these applications also is incorporated herein by reference.

This application is a further continuation-in-part of U.S. Ser. No. 126,810, filed Sep. 24, 1993, now abandoned which in turn is a continuation application of U.S. Ser. No. 778,510, filed Oct. 17, 1991, now abandoned, which in turn is a continuation-in-part application of each of U.S. Ser. No. 091,547, filed Aug. 31, 1987, now U.S. Pat. No. 5,011,773, issued Apr. 30, 1991; U.S. Ser. No. 098,612, filed Sep. 17, 1987, now U.S. Pat. No. 4,942,123, issued Jul. 17, 1990; U.S. Ser. No. 550,877, filed Jul. 11, 1990, now abandoned; U.S. Ser. No. 553,892, filed Jul. 16, 1990, now abandoned; U.S. Ser. No. 108,748, filed Oct. 15, 1987, now abandoned; U.S. Ser. No. 265,829, filed Oct. 31, 1988, now abandoned; and U.S. Ser. No. 553,905,; filed Jul. 16, 1990, now abandoned. The contents of each of these applications are further incorporated herein by reference.

This invention was made with Government support under grant No. EY 05758 from the National Institute of Health. The United States Government has certain rights in this invention.

Throughout this application, references to publications are referred to by their bibliographic citations. The disclosures of these publications are hereby incorporated by reference to more fully describe the state of the art to which this invention pertains.

This invention relates generally to a method of cell therapy to prevent proliferation of pathologically proliferating cells, i.e., to accomplish tumor suppression by administration of either a prophylactically or therapeutically effective amount of a cancer suppressor protein such at the RB protein or polypeptide.

BACKGROUND OF THE INVENTION

Significant progress has been made in understanding the function of genes in maintenance of the health of the organism. As a general rule, it may be stated that the failure of a cellular gene to produce an appropriate protein is the cause of numerous pathologies in the organism. The failure may be due to the fact that an entire gene is missing or because the gene is itself defective for various reasons. In recognition of these factors, significant advances have been made in gene therapy.

For example, Wilms tumor, a childhood cancer of the kidney, is thought to arise by inactivation of a gene on chromosome 11. Using the technique of microcell fusion-mediated transfer of single chromosomes, it has been demonstrated that introduction of a normal chromosome 11 into Wilm's tumor cells suppressed the tumorigenicity. On the other hand, the introduction of chromosomes X and 13 did not have this effect.

While the transfer of entire human chromosomes may have some value, on an experimental basis, it is not feasible for such transfer to be considered for the treatment of genetic defects. For one thing, preparation of suitable chromosomes for therapeutic applications is very exacting, time consuming and expensive. As a result, such a technique has not been found to be acceptable for many applications.

The next logical consideration, given the undesirability of attempting therapeutic use of entire chromosomes, is to deliver to the patient all, or at least operative portions, of the appropriate gene. While such an approach may be more feasible than the delivery of entire chromosomes, gene therapy is desirable for certain applications only.

In this regard, the isolation, sequencing and cloning of the appropriate nucleic acid material is very expensive, and time consuming. In addition, such techniques require a level of sophisticated molecular genetic techniques that are available only in very limited locations in the world. Further, at the present time, such techniques are not adapted for production of large amounts of materials suitable for therapeutic applications.

In view of the above, it would be highly desirable to have a method for specific therapeutic treatment, at the cellular level, utilizing biotechnical techniques, and employing materials which are relatively low-cost, reliable, more generally available and specific in their biochemical action. Further, it would be highly desirable to have methods of treatment which would be capable of permitting delivery of a therapeutic product at the cellular level to effect changes such as the suppression or suppression of tumors. Of course, it would be highly desirable to have a product which could be made, in large quantities, in a consistently purified state and which would be readily and effectively deliverable to the defective cell.

One disease that would be desirable to be treated in this manner is retinoblastoma. Retinoblastoma is a malignant tumor of the sensory layer of the retina. The neoplastic tumor is composed of primitive retinal cells, occurring often bilaterally, usually before the third year of life. It exhibits a familiar tendency. Retinoblastomas are characterized by small round cells with deeply stained nuclei, and elongated cells forming rosettes. They usually cause death by local invasion, especially along the optic nerves.

The retinoblastoma may be hereditary but also acquired. It is the most common intraocular tumor and represents one of the prototypes of inheritable cancers. The hereditary form is characterized by early age of onset and multiple tumor foci. Acquired form occurs later in life with single unilateral tumor (*Proc. Natl. Acad. Sci.* (1971) 68:820–823; *Hum. Genet.* (1979) 52:1–54; *Science* (1984) 223:1028–1033.

Susceptibility to hereditary retinoblastoma is transmissible to offsprings as an autosomal dominant trait with 90% penetrance, and the tumor has been and is, therefore, a prototypic model for the study of genetic determination in cancer (*Am. J. Hum. Genet.* (1978) 30:406–410; *Cancer* (1975) 35:1022–1026).

There are at least two hypotheses related to the oncogenesis of retinoblastoma. The first hypothesis suggests that the tumor is caused by two mutational events (*Proc. Natl. Acad. Sci.* (1971) 68:820–823; *Cancer* (1975) 35:1022–1026). The other hypothesis proposes that autosomal dominant hereditary tumors, such as retinoblastoma, represent the inheritance of a defective regulatory or suppressor gene which normally regulates a group of transforming genes, most probably proto-oncogenes. During retinal cell development, it is assumed that a mutation causes loss of a second copy of the RB gene. Therefore, the RB protein is not produced at the appropriate time and differentiation cannot occur.

It is well recognized that in the development of higher organisms, such as animals and humans, orderly cell cycle progression is a critical factor. Because of such progression, ordered and systematic cell differentiation occurs so that, ultimately from a single undifferentiated cell, a highly structured organism, having a variety of specialized tissues, develops. In general, physiologically normal cell cycle progression is very important to the organism, not only during the stages of early growth, but throughout the entire life of the organism. Thus, even after the organism has reached maturity, normal cycle progression is still a very important aspect of health. This, for example, can be clearly seen in the importance of proper cellular regulation in the blood forming and reproductive organs.

Under certain circumstances, normal cell cycle progression fails, often with catastrophic effects for the organism. Such a failure is seen, for example, in the various forms of cancer where, because of an unchecked, and uncontrolled, progression of cells through the cell cycle, from the completion of mitosis through interphase and back into mitosis, tumorigenesis becomes, in many cases, a life threatening event. Thus, a restraint on uncontrolled cell cycle progression is sometimes attempted in an effort to treat or control the tumorigenic condition.

Based on these hypotheses, hereditary retinoblastoma might arise from a precursor retinoblast cell, carrying one inherited defective allele which suffers an additional somatic mutation, while nonhereditary cases would require two somatic mutations in the same cell. Recent circumstantial evidence supports the existence of such cancer suppressor genes in retinoblastoma as well as nephroblastoma also known as Wilm's tumor, neuroblastoma, and osteosarcoma.

The RB locus was implicated in non-hereditary retinoblastoma by observing frequent abnormalities of chromosome 13 in tumor karyotypes and reduced esterase D activity in tumors (*Cancer Genet. Cytogenet.* (1983) 10:311–333; *Cancer Genet. Cytogenet.* (1982) 6:213–221). It has been proposed that inactivation of both alleles of the RB gene located in region 13q14 resulted in retinoblastoma. Such proposal was based in part on a case of hereditary retinoblastoma in which both RB alleles were inferred to be absent (*Science* (1983) 219:973–975). However, the assumption upon which this proposal was based, namely that the absence of esterase D activity implied loss of both esterase D and RB genes, has been disproved (*Hum. Genet.* (1987) 76:33–40). Nonetheless, the other findings show that chromosome 13 markers which were heterozygous in somatic cells often became homozygous or hemizygous in retinoblastoma tumors, and that there are homozygous deletions in the 13q14 region in 3/37 retinoblastoma cell lines (*Nature* (1983) 305:779–784; *Proc. Natl. Acad. Sci.* (1986) 83:7391–7394). These experiments provide evidence that the proposed RB gene indeed functions in a recessive manner at the cellular level (*Science* (1987) 235:305–311; *Cancer Res.* (1986) 46:1573–1580) in distinction to the "dominant" activity of classical oncogenes (*Science* (1985) 228:669–676; *Nature* (1985) 315:190–195) as measured, for example, by transfection assays.

Both forms of retinoblastoma can now be treated and most patients can be followed through adult life. However, patients with hereditary retinoblastoma have an extraordinarily high risk for developing a second non-ocular malignancy (*Ophthalmology* (1984) 91:1351–1355; *New Engl. J. Med.* (1971) 285:307–311; *Cancer* (1974) 34:2077–2079), with up to 90% incidence within 30 years of initial diagnosis (*Ophthalmology* (1984) 91:131–136). The most frequently occurring secondary cancer is osteosarcoma, which is otherwise uncommon. In contrast, cured nonhereditary retinoblastoma patients show the same cancer rates as the general population. This finding is of considerable interest, since it implies that the RB gene may have a critical role in regulating other tumors as well.

The human retinoblastoma gene has been successfully cloned, identified and sequenced (*Science* (1987) 235:1394–1399). The retinoblastoma gene was located in the chromosome 13 region 13q14:11 in the close proximity of the esterase D gene, which also has been identified, cloned and sequenced (*Proc. Natl. Sci.* (1986) 83:6790–6794; *Proc. Natl. Acad. Sci.* (1986) 83:6337–6341; *Proc. Natl. Acad. Sci.* (1986) 83:6337–6341). By chromosomal walking from esterase D gene, the retinoblastoma (RB) gene was identified on the basis of chromosomal location, homozygous deletion and tumor-specific alterations in expression. RB gene was shown to have 4723 nucleotides and encodes a messenger RNA (mRNA) of 4.8 kilobases (kb).

Transcription of RB DNA to RB mRNA was found to be abnormal in retinoblastoma patients. Transcription was either not detected at all, suggesting the absence or complete inactivation of the RB gene, or transcribed mRNA had shown decreased molecular size of about 4.0 kb, suggesting defective RB gene.

Sequencing of RB complementary DNA (cDNA) clones yielded a single long open reading frame suggesting that it could encode a hypothetical protein of 816 amino acids. A computer-assisted search of a protein sequence data base revealed no closely related proteins suggesting a unique amino acid sequence of the predicted protein (*Science* (1987) 235:1394–1399. The predicted protein will seem to have several proline rich regions, similar to those previously observed in other nuclear oncogene proteins such as proteins "myc" and "myb" (*RNA Tumor Viruses*, Cold Spring Harbor Laboratory, Cold Spring Harbor, N.Y. (1985)).

Under current conditions, where tumorigenesis has developed, drastic treatment measures, such as radiation therapy and chemotherapy are employed. Both of these modalities are very expensive and, in some cases, very damaging to the organism. Chemotherapy, for example, can cause the death of the patient and when chemotherapy is successful in controlling tumorigenesis, it may have long term adverse effects on the body. Such an adverse effect may result in premature heart problems for the patient. Thus, while conventional therapeutic methods, such as radiation and chemotherapy, serve a useful purpose in destroying certain uncontrolled cells, they also produce the unwanted effects of destroying useful cells and weakening organ systems.

In view of the foregoing, it would be highly desirable to have techniques and compositions for regulating unwanted cell progression, such as in tumorigenesis, while maintaining cell viability. In addition, it would be further very highly desirable if such techniques and compositions produce little or no adverse effects on the cell and, halt the development of tumorigenesis without causing irreversible changes at the cellular level.

A significant advantage of such novel techniques and compositions, in the case of tumorigenesis, would be the possibility of regulating unwanted cell proliferation, for enough time for other cancer treating procedures to be applied. Thus, the use of such techniques could reduce or eliminate the ravaging effects of conventional radiation and chemotherapeutic treatments, while arresting tumorigenesis. Hence, the patient would retain strength and vigor so that conventional techniques, such as surgery, could be more safely utilized.

SUMMARY OF THE INVENTION

This invention provides methods for preventing or inhibiting the proliferation of a pathologically proliferating cell, wherein the pathological proliferation of the cell is the result of the absence of a functional retinoblastoma protein or polypeptide in the cell. The methods require contacting the cell with an effective amount of retinoblastoma protein or polypeptide. These methods also are useful to prevent or treat retinoblastoma or a cancer secondary to retinoblastoma, by administering to a patient a functional retinoblastoma protein or polypeptide.

DETAILED DESCRIPTION OF THE FIGURES

FIG. 1 is the chromatogram illustrating the identification of RB proteins by immunoprecipitation with rabbit anti-RB IgG in various cell lines. Human cells such as neuroblastoma LAN-1 (Lanes 1 and 2), Alexander hepatoma (Lane 3), osteosarcoma U20S (Lane 4), normal fibroblasts (Lane 5), and five retinoblastomas (Lanes 6 to 10) were labeled with $^{35}$S-methionine and immunoprecipitated with preimmune rabbit IgG (Lane 1) or rabbit anti-RB IgG (Lanes 2–10). The immunoprecipitates were analyzed by 7.5% SDS-polyacrylamide gel electrophoresis and autoradiographed.

FIG. 2 is the complete RB cDNA nucleotide sequence and predicted amino acid sequence of the RB protein. This protein is designated ppRB$^{110}$ or p110$^{RB}$. The most 5'~240 nucleotides were obtained from a cDNA clone from retinoblastoma cell line Y79. Nucleotide sequences from this clone and the original normal RB clones were aligned by sequence overlap. The first and second initiation sites are boxed, and alanine and proline clusters underlined.

FIG. 3 is the chromatogram illustrating the modifications of the RB protein. LAN-1 cells were labeled with $^{35}$S-methionine (lanes 1–3) or $^{32}$P-phosphoric acid (0.5 mci/ml) (lanes 4 and 5) for three hours. Cellular lysates were immunoprecipitated with preimmune rabbit IgG (lane 1 and 4) or anti-RB IgG (lanes 2, 3 and 5). Aliquots of $^{35}$S-methionine-labeled RB proteins were digested with endoglycosidase H (ICN ImmunoBiologicals) overnight (Lane 3). These immunoprecipitates were then analyzed by 7.5% SDS-polyacrylamide gel as described in FIG. 1. The RB gene product was found to be phosphorylated but not glycosylated.

FIG. 4 is the chromatogram illustrating a conservation of the RB gene product in different vertebrate species. Cell lines of human neuroblastoma, LAN-5 (Lanes 1 and 2), monkey cos, (Lanes 3 and 4), quail fibroblast, QT6, (Lanes 5 and 6), mouse fibroblast, NIH/3T3), (Lanes 7 and 8), and rat fibroblast, rat-2, (Lanes 9 and 10) were labeled with $^{32}$P-phosphoric acid and immunoprecipitated with preimmune IgG (odd numbered lanes) or anti-RB IgG (even numbered lanes) and analyzed as described in FIG. 1. RB proteins of similar but distinguishable sizes were found among different vertebrate pieces.

FIG. 5A is the chromatogram showing localization of the RB protein. $^{35}$S-methionine labeled LAN-1 cells (Lane 4) were fractionated into membrane (Lane 1), cytoplasm (Lane 2) and nucleus (Lane 3) and protein was immunoprecipitated with anti-pRB$^{110}$ IgG. The immunoprecipitates were then analyzed by SDS-PAGE as described for FIG. 1.

FIG. 5B is the chromatogram showing the results of the immunofluorescence studies of RB protein localization within the osteosarcoma cell line U2OS. Cells reacted with (i) anti-RB IgG and (ii) preimmune rabbit IgG. Most fluorescence was found within the nucleus.

FIG. 6A is the picture of the column chromatography of the RB gene phosphoprotein in single stranded DNA cellulose. Protein lysates of the human neuroblastoma cells LAN-1 were metabolically labeled with $^{32}$P-phosphoric acid and passed through a single stranded DNA columns and eluted with increasing gradient of NaCl (Lane 3=0.05; Lane 4=0.1; Lane 5=0.2; Lane 6=0.3; Lane 7=0.5 and Lane 8=1.0M NaCl). Lane 1 shows the whole cell lysate immunoprecipitated with anti-RB IgG.

FIG. 6B is the picture of the column chromatography of the RB gene phosphoprotein in double stranded DNA cellulose. Protein lysates of the human neuroblastoma cells LAN-1 were metabolically labeled with $^{32}$P-phosphoric acid and passed through a double stranded DNA column and eluted with increasing gradient of NaCl (Line 3=0.05; Line 4=0.1; Line 5=0.2; Line 6=0.3; Line 7=0.5 and Line 8=1.0M NaCl). Line 1 shows the whole cell lysate immunoprecipitated with anti-RB IgG.

FIG. 7A is the drawing illustrating the production of the TRP E-RB fusion protein. EcoR1-EcoR1 cDNA RB fragment (0.7 kb) was fused in-frame into the EcoR1 site of pATH3 vector. Orientation was confirmed by detailed restriction enzyme mapping. The recombinant plasmid was then transformed into E. coli mm294.

FIG. 7B is the picture of the polyacrylamide gel electrophoresis of the recombinant TRP E-RB fusion protein. The recombinant plasmid was then transformed into E. coli mm294, and grown in M9 minimal medium supplemented with 20 mg/ml of tryptophan. The culture was diluted to 1:100 in M9 plus casamino acids and ampicillin. At an optical density at 600 nm of 0.2, a 1:1000 dilution of a 10 mg/ml stock of indoleacrylic acid in 100% ethanol was added to induce the expression of the TRP E promoter. Bacteria cells were pelleted and boiled in Laemmli gel sample buffer for 15 minutes and analyzed by polyacrylamide gel electrophoresis. Gel was then stained with Coomassie blue. A 58 kD protein was found in induction culture (Lane 2) but not in control culture (Lane 1).

FIGS. 8A and 8B show immunoprecipitation of the RB protein from various cell lines.

FIG. 8A is the chromatogram showing immunoprecipitation of RB protein/anti-RB protein IgG from the various human cell lines. $^{35}$S-methionine-labeled cells extracts prepared from a human hepatoma Alexander cell line (Lane 1), human osteosarcoma cell line, U2OS (Lane 2), normal human fibroblast (Lane 3), human neuroblastoma cell line, LAN-5 (Lane 4), and from neuroblastoma lysates precipitated by preimmune rabbit IgG (Lane 5) were immunoprecipitated with purified rabbit anti-RB IgG. Doublet bands with apparent molecular weight about 110–114 kD were observed in Lanes 1–4.

FIG. 8B is the chromatogram showing immunoprecipitation of RB protein/anti-RB protein IgG from the several retinoblastoma cells.

Cell extracts from five different retinoblastoma cell lines were labeled with $^{32}$S-methionine and immunoprecipitated with purified rabbit anti-RB IgG. Doublet bands present in cell lines from hepatoma, osteosarcoma, fibroblastoma and neuroblastoma were absent in all five retinoblastoma cell lines RB 355 (Lane 1), Y79 (Lane 2), WERI-1 (Lane 3), WERI-24 (Lane 4), and WERI-27 (Lane 5), human neuroblastoma cell line LAN-5 (Lane 6) and from neuroblastoma lysates precipitated by preimmune rabbit IgG (Lane 7). The RB protein was identified based on these results.

Figure 9:
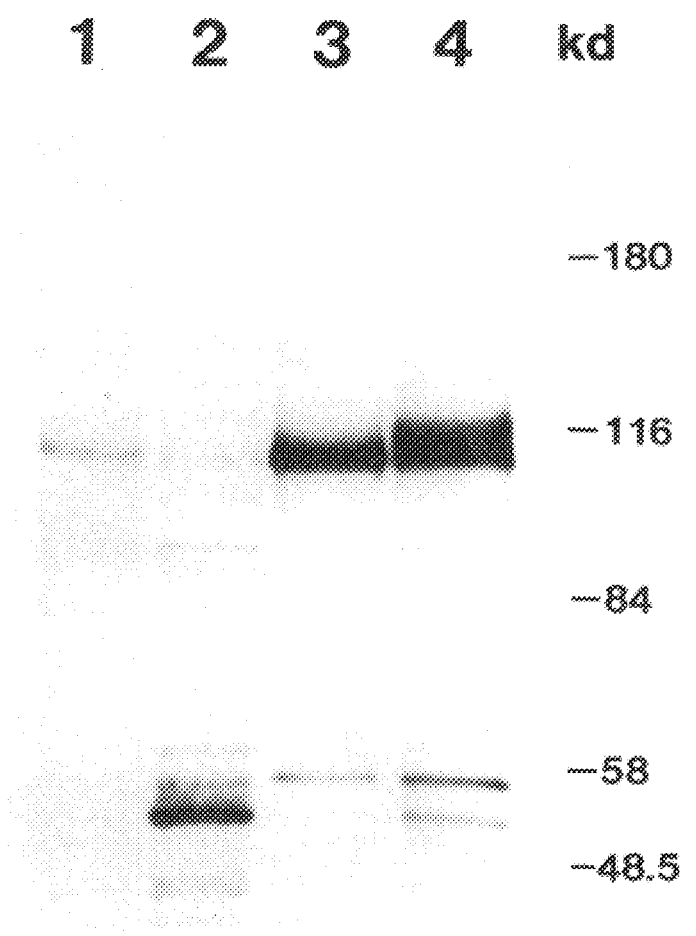

FIG. 9 is the chromatogram showing a biochemical fractionation to demonstrate the localization of the RB protein. $^{35}$S-methionine labeled whole cells of LAN 5 (Lane 4) was fractionated into membrane (Lane 1), cytoplasm (Lane 2) and nucleus (Lane 3) and were subsequently immunoprecipitated with rabbit anti-RB IgG. The majority of the $RB^{110-114}$ protein was found in the nucleus with minor portions in membrane or cytoplasm.

FIG. 10A and 10B depict Southwestern DNA-binding assays. Six μg of purified TRPE-RB fusion proteins, as well as purified baculovirus-expressed pp110$^{RB}$, were applied to 10% SDS-PAGE.

FIG. 10A depicts a Southwestern DNA binding assay of fusion proteins and baculovirus-expressed p110$^{RB}$ applied to 10% SDS-PAGE, Coomassie brilliant blue staining. Coomassie brilliant blue staining was used and incubated with $^{32}$P-labeled DNA fragments and analyzed by autoradiography. The following are shown: lane 1: RB19- 22; lane 2: RB23-27; lane 3: RB19-27.

FIG. 10B is an autoradiograph of a blot from a parallel gel to the gel used to produce FIG. 10A. It has been demonstrated that fusion protein RB19-27, which contains the major domain for interacting with DNA, has a 20-fold higher affinity for DNA than either of two subregions, RB19-22 and RB23-27. In this regard, lane 3 of FIG. 10B can be compared with lanes 1 and 2, while the purified full-length RB protein exhibited (FIG. 10B; lane 4). DNA-binding activity of the purified RB protein from insect cells was also demonstrated by retention of the protein by DNA-cellulose and its subsequent elution from the column, at approximately 400 mM NaCl.

FIG. 11 is a chromatograph showing complex formation of baculovirus-expressed RB protein (p110$^{RB}$) with SV40 T-antigen. The purified full length RB protein was mixed with purified T-antigen in a test tube, i.e., in vitro. Identical aliquots of the mixtures were then immunoprecipitated with PAB419 (lane 2) or anti-RBO.47 (lane 3) and analyzed by western blotting. Lanes 1 and 4 show purified SV40 T-antigen immunoprecipitated with PAB419, and purified baculovirus-expressed RB protein immunoprecipitated with anti-RBO.47 antibody, respectively.

Mixing of RB protein with SV40 T antigen in vitro resulted in the co-immunoprecipitation of the RB protein with PAB419 (lane 2), as well as the co-immunoprecipitation of T with anti-RBO.47 antibody (lane 3).

FIG. 12 is a photograph depicting nuclear translocation of purified protein after microinjection into the cytoplasm of Soas-2 cells. The protein preparations used for microinjection were analyzed by SDS-PAGE. Lane 1: p110$^{RB}$ from insect cells infected with recombinant RB baculovirus; lane 2: biotinylated rabbit anti-goat antibody; lane 3: anti-RB 0.495 antibody; lane 4: anti-RB R2 antibody; lane 5: anti-RB 0.47 antibody; lane 6: histone H1; lane 7: p56$^{RB}$ from E. coli. One microliter of each sample was loaded on a 15% acrylamide gel. The gel was stained with Coomassie brilliant blue. The positions of molecular weight standards, in kiloDaltons, are indicated.

Figure 15:
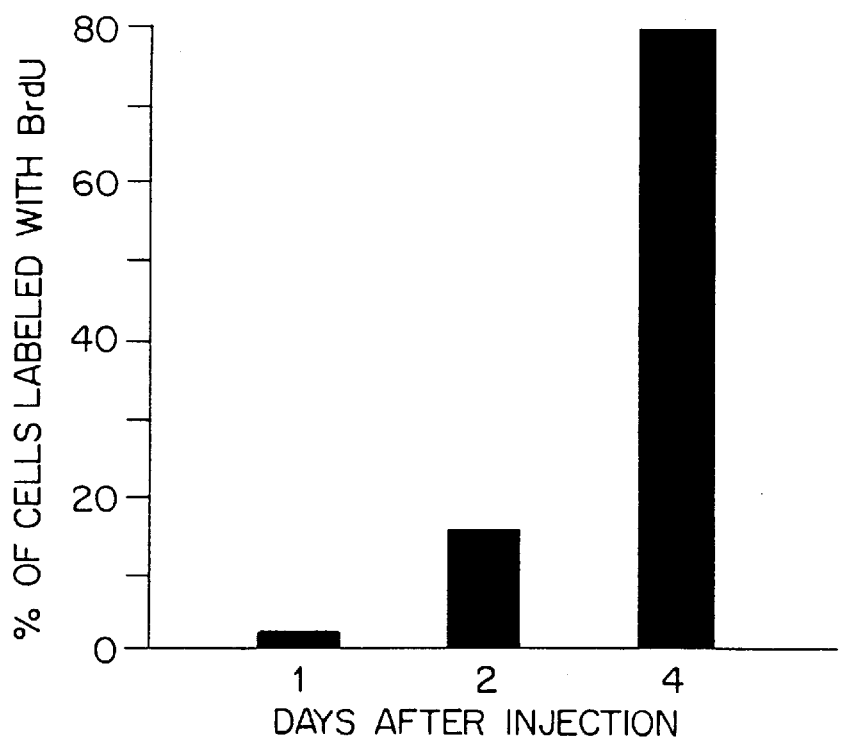

FIG. 15 graphically depicts the percentage of labeled cells up to four days after injection.

Figure 16:
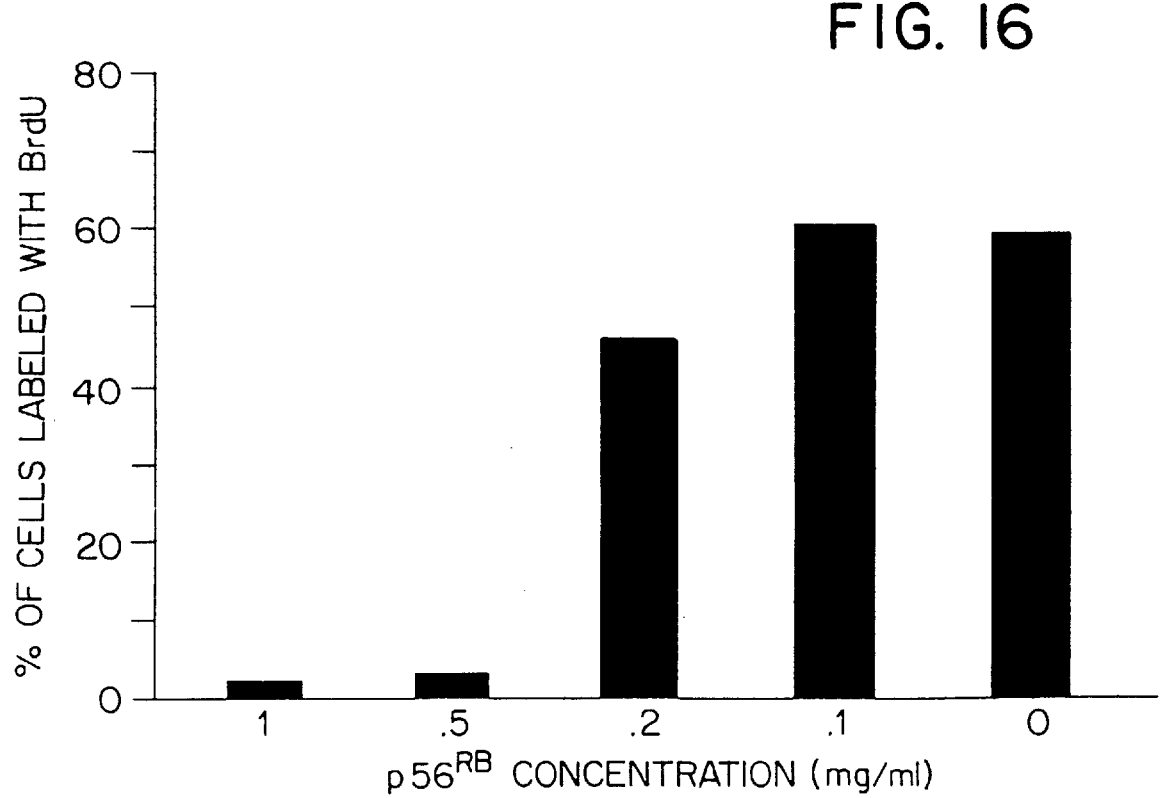

FIG. 16 graphically depicts the percentage of labeled cells as a function of p56 concentration.

FIG. 17 graphically depicts the effect on cells when p56$^{RB}$ is injected in S phase.

Figure 18A:
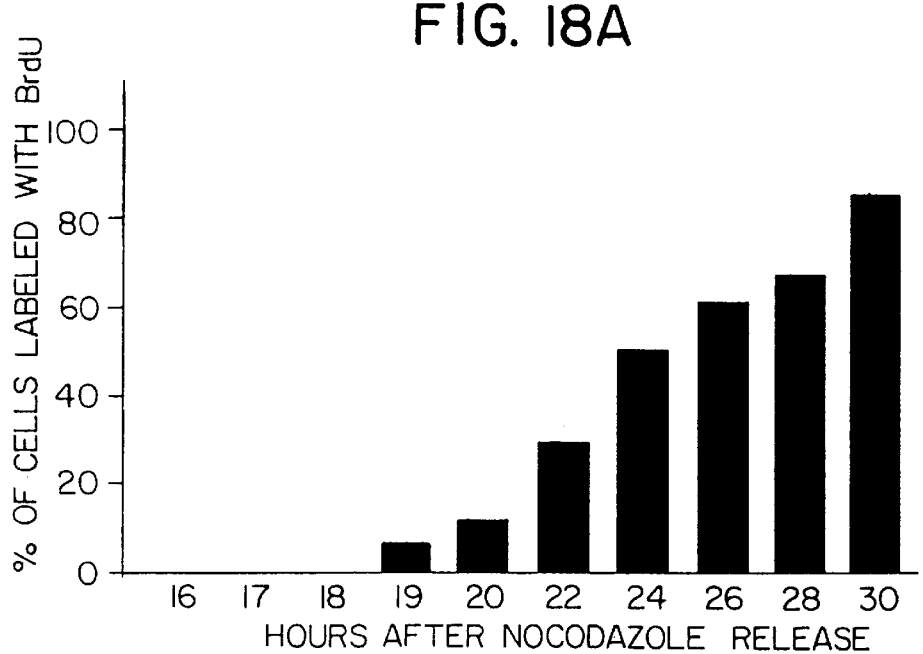
Figure 18B:
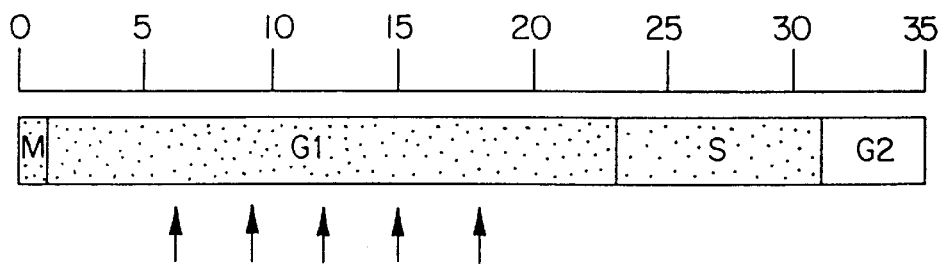
Figure 18C:
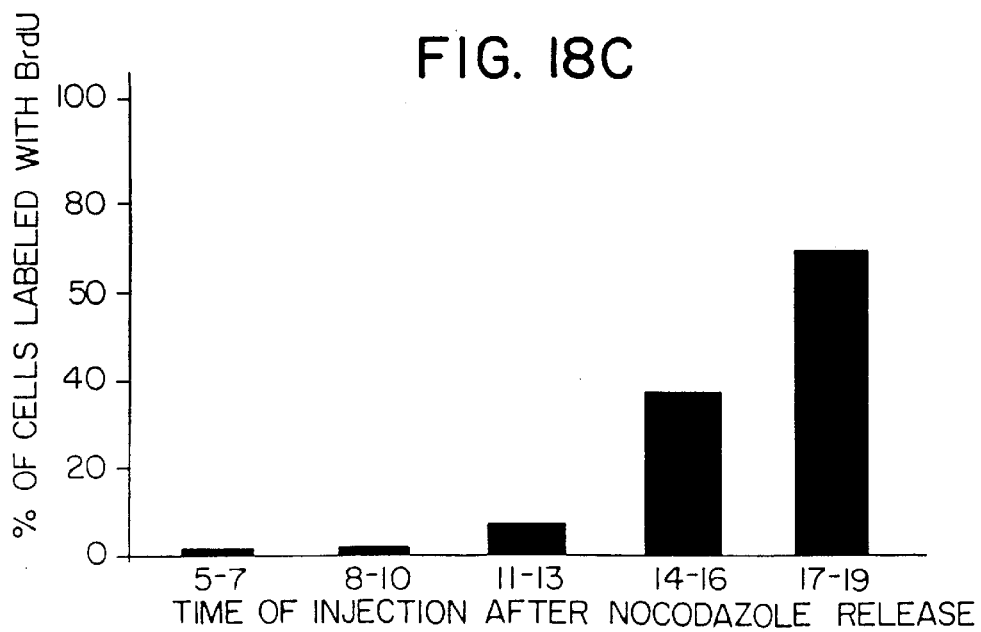

FIGS. 18A through 18C graphically depict the dependence of cell cycle arrest on the time period of injection for the truncated protein.

Figure 19:
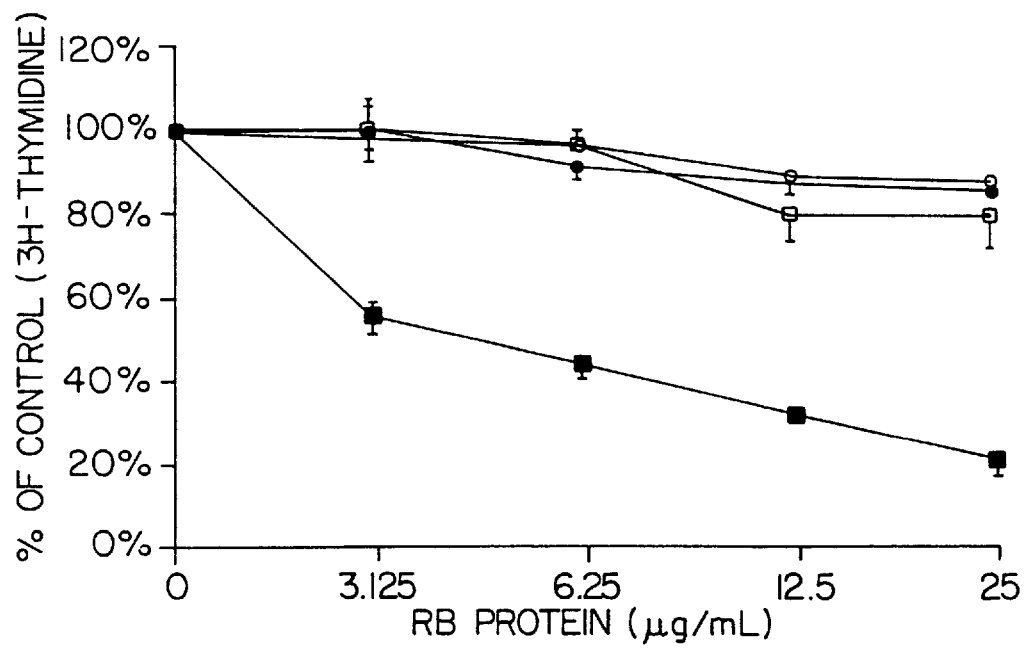

FIG. 19 shows p110$^{RB}$ inhibits the growth of both small cell and non-small cell lung cancer cell lines which are defective in Rb protein expression. The results of this experiment demonstrate that p110$^{RB}$ can inhibit proliferation of NCL-H596 (NSCLC; Rb-negative). p110$^{RB}$ has less activity on the A549 (NSCLC; Rb-positive) tumor cell line. The p110$^{RB}$ used in this experiment was derived from either baculovirus (B-Rb; purified as described in Cell Growth (1990) supra) or from E. coli (E-Rb). The control protein employed was bovine serum albumin (BSA). All proteins were present in the growth media at 25 μg/ml.

Figure 20:
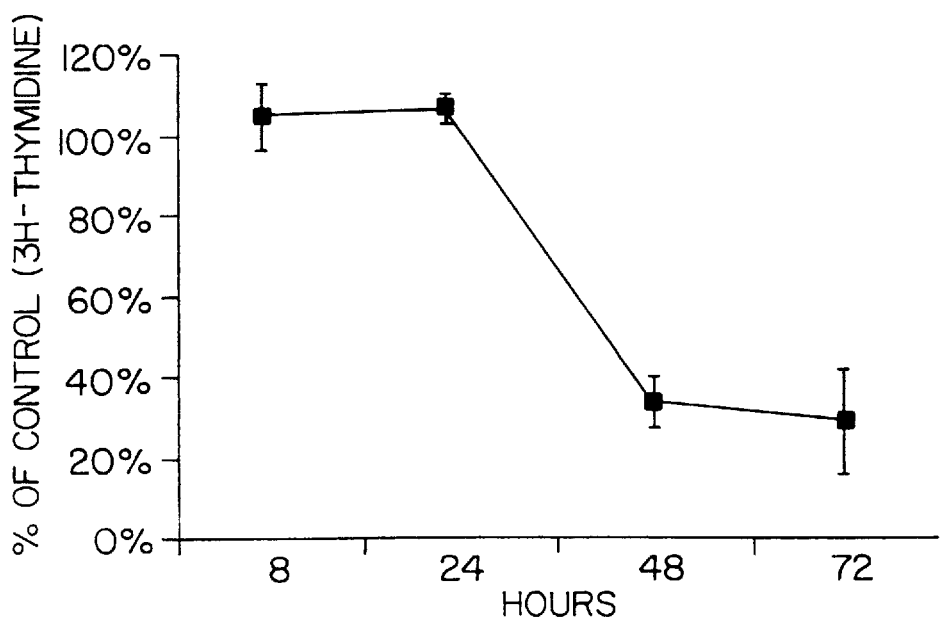

FIG. 20 is the results of a time course study of RB-mediated growth inhibition. $^{3}$H-thymidine incorporation is expressed as the percent of a buffer control±S.D.

FIGS. 21A through 21D show cellular uptake and nuclear localization of $^{125}$I-p110$^{RB}$.

Figure 21A:
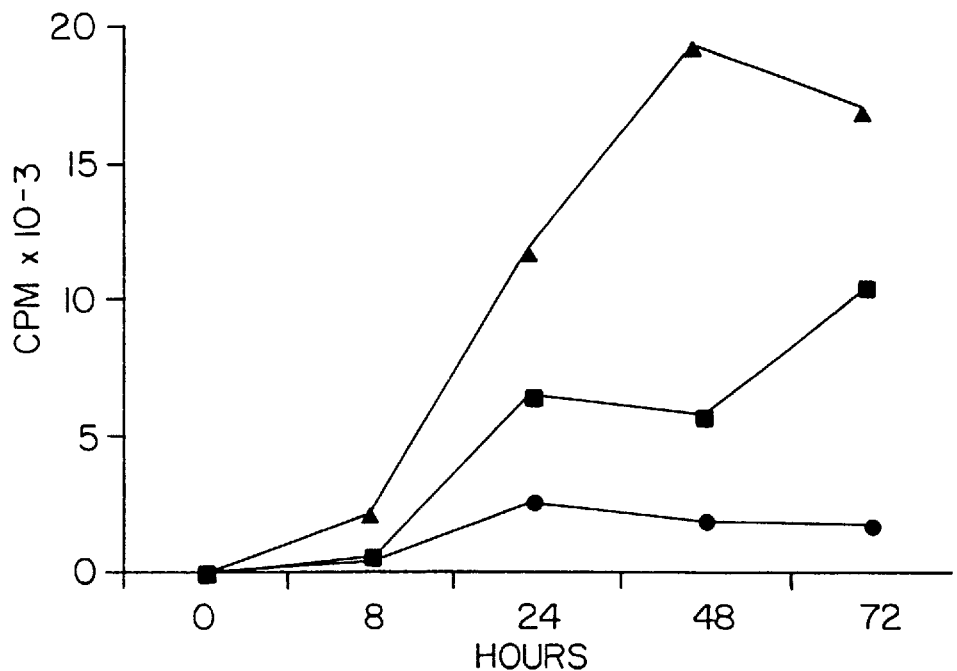

FIG. 21A shows time-dependent localization of $^{125}$I-p110$^{RB}$ to various subcellular fractions.

Figure 21D:
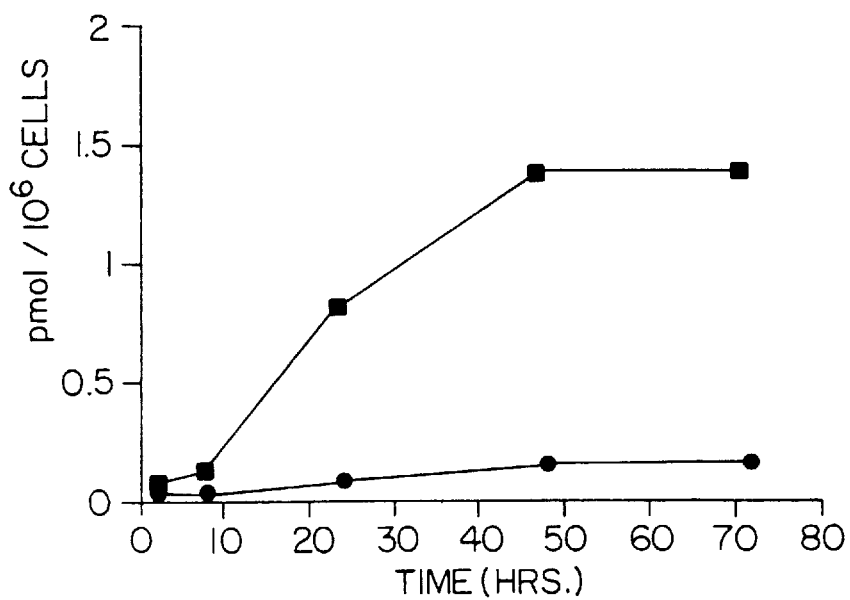
Figure 21B:
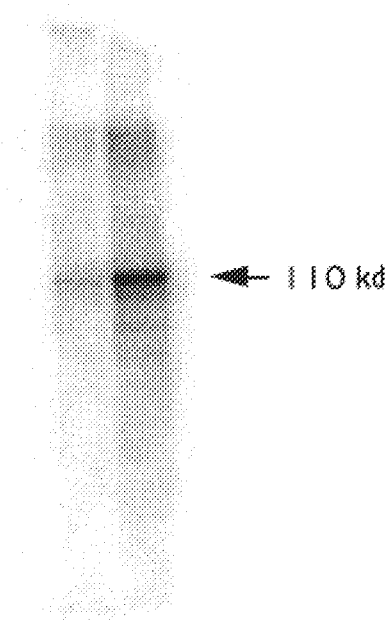

FIG. 21B shows immunoprecipitation and identification of $^{125}$I-p110$^{RB}$ in NCl-H596 nuclear fractions. Molecular size standards are indicated. Lane 1: 0 hours; Lane 2: 1 hour; Lane 3: 48 hours; Lane 4: $^{125}$I-p110$^{RB}$ protein standard.

Figure 21C:
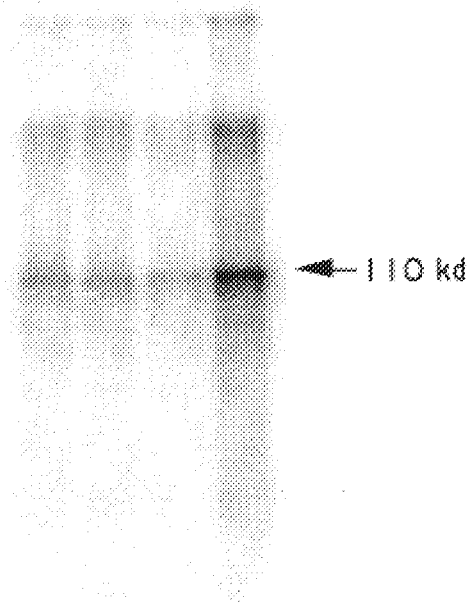

FIG. 21C shows immunoprecipitation and identification of $^{125}$I-p110$^{RB}$ in nuclear fractions of Lung cell lines. Lane 1: NCl-H596 NSCLC (RB$^{neg}$); Lane 2: A549 NSCLC (RB$^{pos}$); Lane 3: MRC-9 normal lung epithelium (RB$^{pos}$); Lane 4: $^{125}$I-p110$^{RB}$ protein standard.

FIG. 21D shows quantification of nucleus-localized $^{125}$I in NCl-H596 NSCLC cells. Cells were harvested at 0, 8, 24, 48 and 72 hours and nuclear $^{125}$I-p110$^{RB}$ (■) or $^{125}$I-p56$^{RB}$ (●) was quantitated.

FIG. 22 shows the effect of peritumoral injection of RB protein on the growth of subcutaneous lung tumors in nude mice.

Figure 22A:
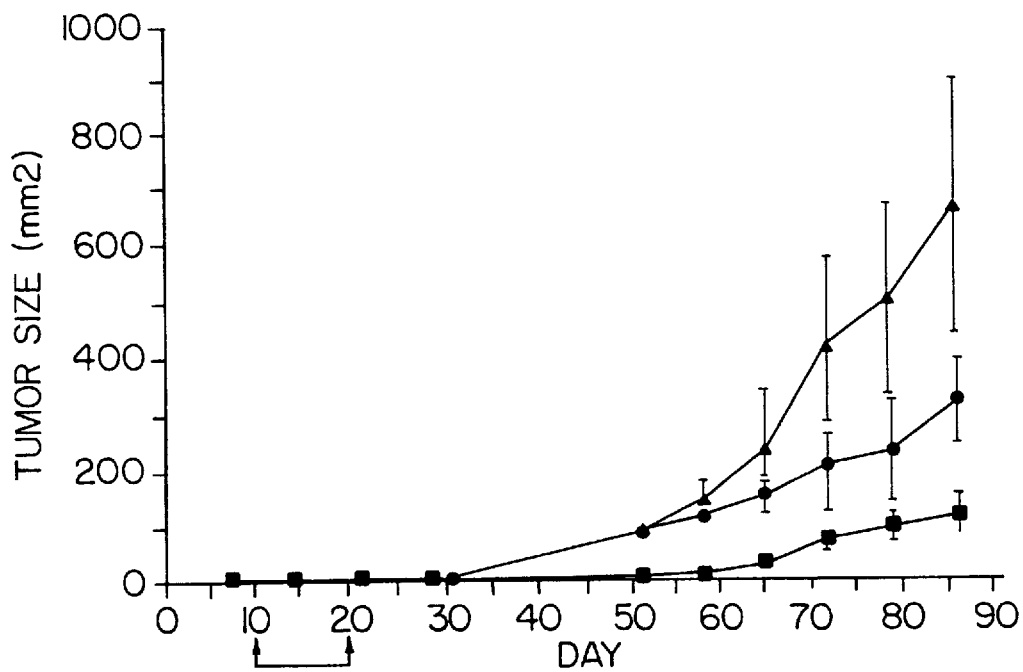

FIG. 22A indicates the NCl-H596 (RB$^{neg}$) tumor sizes shown represent the mean value of each treatment group of 3 animals±S.D. Tumor sizes at day 87 (mm$^{2}$) were: p110$^{RB}$-treated: 169, 130, 100; p56$^{RB}$-treated: 400, 360, 252; buffer treated: 858, 420, 770 (■)-p110$^{RB}$, (●-p56$^{RB}$, (▲)-buffer control.

Figure 22B:
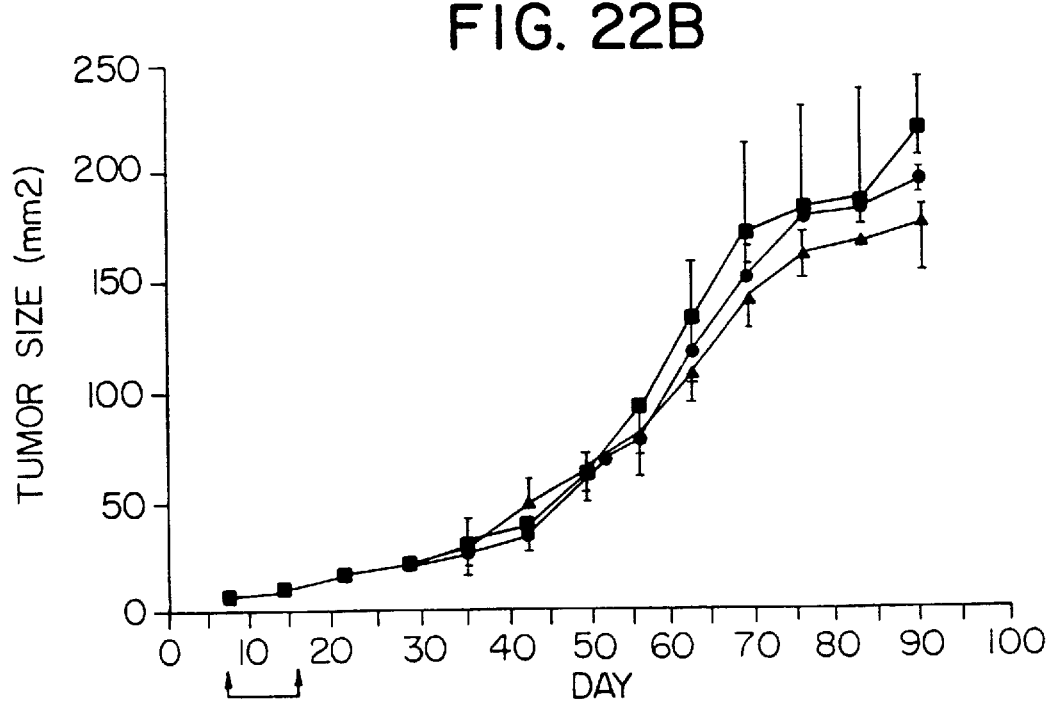

FIG. 22B indicates the A549 (RB$^{pos}$) tumor sizes shown represent the mean value of each treatment group of 3 animals±S.D. Tumor sizes of individual animals at day 87 (mm$^{2}$): p110$^{RB}$ treated: 120, 136, 118; p56$^{RB}$-treated: 118, 132, 121; buffer treated: 110, 139, 126. (■)-p110$^{RB}$, (●-p56$^{RB}$ (▲)-buffer control.

Figure 23:
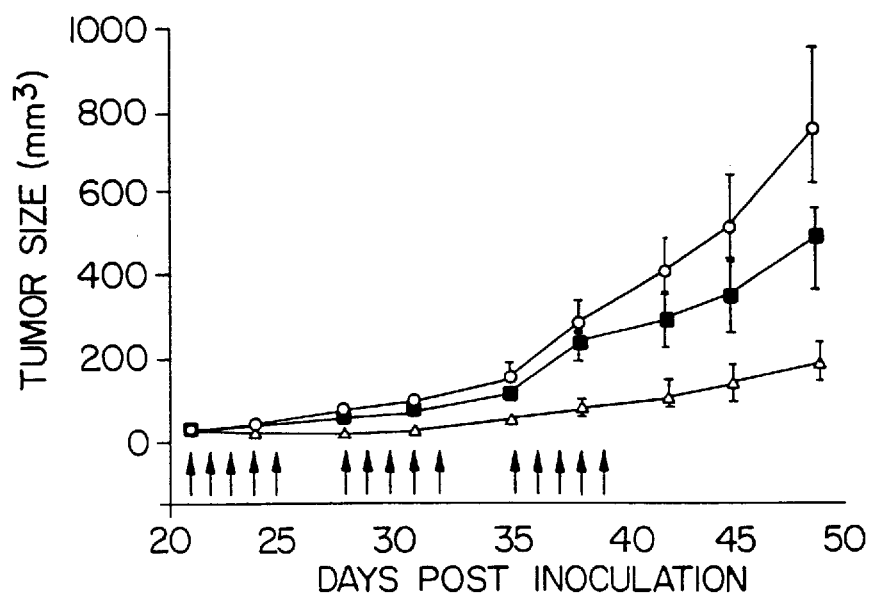

FIG. 23 shows the effect of intravenous administration of p110$^{RB}$ on the growth of human lung tumor cells in nude mice. Active p110$^{RB}$, 50 μg/dose (■); active p110$^{RB}$ 200 μg/dose (△); or inactive p110$^{RB}$ 200 μg/dose (○). Values shown are Mean (±SEM). Arrows indicate days of treatment.

Figure 24:
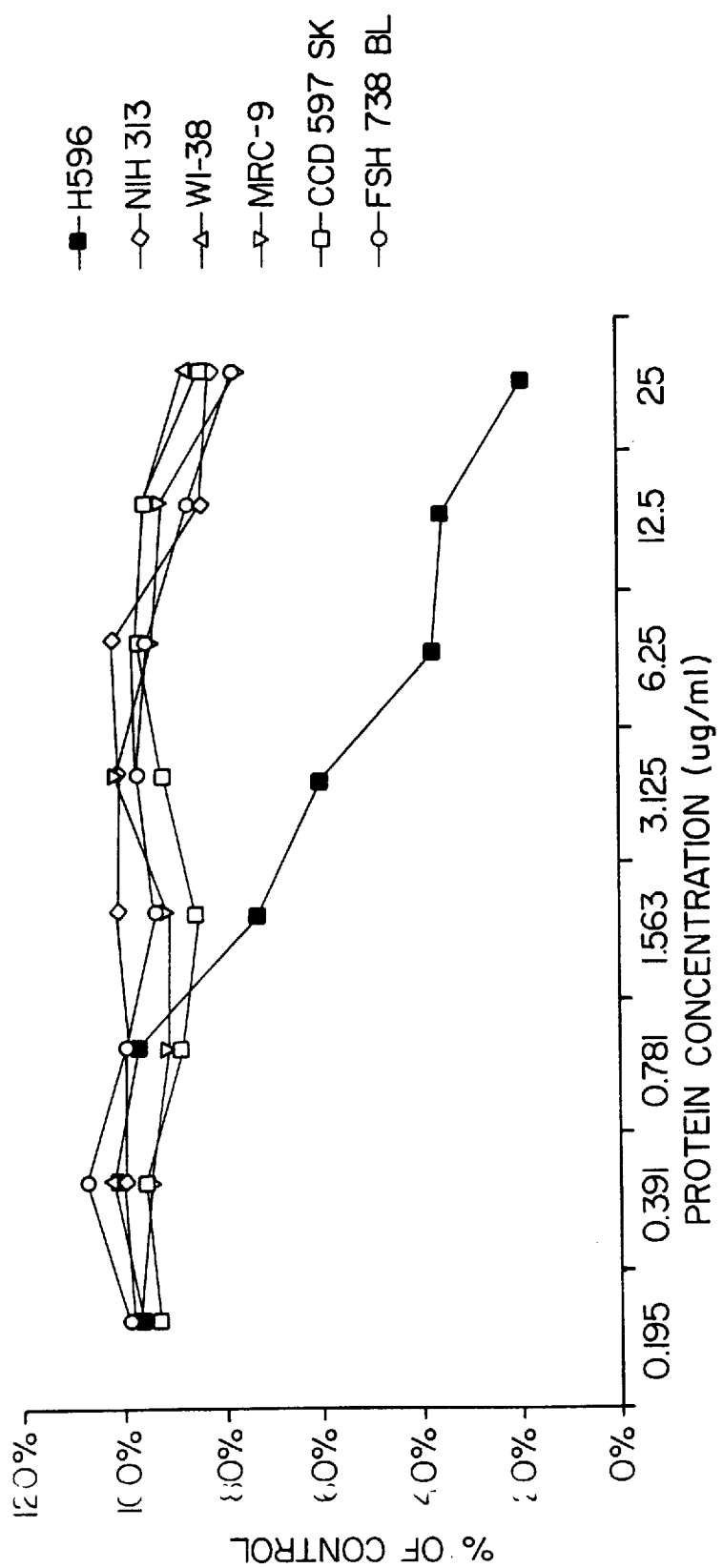

FIG. 24 shows p110$^{RB}$ can inhibit the growth of non-small cell lung cancer cells in vitro while having no effect on the proliferation of normal cell lines. p110$^{RB}$ was prepared from E. coli strain BL21, containing a T7 promoter driving expression of full length p110$^{RB}$ (described in S. Huang et al., infra.). The p110$^{RB}$ was purified according to the protocol described in Cell Growth and Diff. (1990) 1:429–437. For the experiments shown in FIG. 24, cells were incubated with the indicated concentrations of p110$^{RB}$ added every 8 hours for the duration of the experiment. $^3$H-Thymidine was added overnight for the last 8 hours to measure cellular DNA synthesis. Cell types used for these experiments were purchased from the American Type Culture Collection. They include: H596 (Rb-negative; Non-small cell lung cancer), MRC-9 (Rb-positive; normal lung epithelial cell line), WI-38 (Rb-positive; normal lung epithelial cell line), CCD 597 SK (Rb-positive; normal foreskin epithelial cell line), FSH 738 BL (Rb-positive; normal bladder epithelial cell line), NIH 3T3 (Rb-positive; non-transformed murine cell line).

FIG. 25 shows p110$^{RB}$ inhibits the growth of both small cell and non-small cell lung cancer cell lines which are defective in Rb protein expression. The results of this experiment demonstrate that p110$^{RB}$ can inhibit proliferation of H128 and H69 cell lines (both Rb-negative), and H596 (NSCLC; Rb-negative). p110$^{RB}$ has less activity on the A549 (Rb-positive) tumor cell line. The p110$^{RB}$ used in this experiment was derived from either baculovirus (B-Rb; purified as described herein) or from E. coli (E-Rb). The control protein employed was bovine serum albumin (BSA). All proteins were present in the growth media at 25 μg/ml. The assay was otherwise performed as described in the legend to FIG. 24.

FIG. 26 shows that p110$^{RB}$ can enter cells and localize to the nucleus. I$^{125}$-labeled p110$^{RB}$ is shown to enter cells in a time-dependent manner and localize in the nucleus. Cells were fractionated as described in Nature (1987) 329:642–645.

Figure 27:
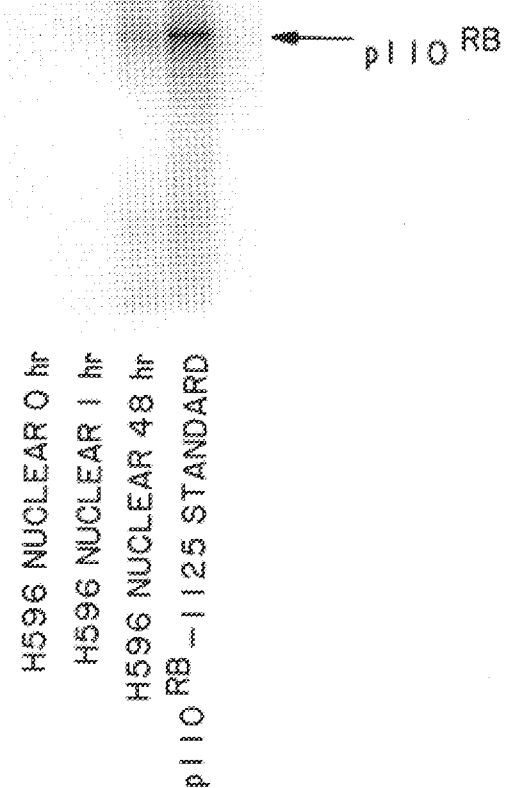

FIG. 27 shows that intact p110$^{RB}$ can be detected in the nuclei of H596 tumor cells treated with I$^{125}$-labeled p110$^{RB}$. This figure shows that when the nuclear fraction (prepared as described (Ibid)), is examined by denaturing SDS gel electrophoresis and autoradiography, that full length p110$^{RB}$ is seen in the nucleus following 48 hours of incubation. An iodinated p110$^{RB}$ was used as marker for the autoradiography.

FIG. 28 shows both p110$^{RB}$ and p56$^{RB}$ have biological activity for subcutaneous therapy of non-small cell lung cancer in an animal model. Both proteins were prepared from E. coli BL21, as described above, using the purification methodology as described by herein, 100 μg of p110$^{RB}$ or p56$^{RB}$ was administered daily/subcutaneously in the region of the tumor. Both proteins had demonstrable biological activity as shown in the Figure. Although p56$^{RB}$ had less activity than p110$^{RB}$, this experiment does demonstrate that fragments of p110$^{RB}$ do have biological activity.

FIG. 29 shows parenteral therapy of lung cancer using p110$^{RB}$ in a relevant animal model. 200 μg of p110$^{RB}$ was injected three times weekly via the tail vein of Balb/c nude mice which had established and rapidly growing subcutaneous H596 human NSCLC tumors. This dose corresponds to a human dose of approximately 1 mg per kg. The experiment was carried out over a 1 month period, as shown. During therapy, the untreated tumors grew rapidly and the treated tumors either did not grow, or grew at a much reduced rate.

FIG. 30 shows the amino acid sequence of retinoblastoma protein produced in E. coli. As compared to FIG. 2, when the protein is produced in E. coli, the second amino acid (proline) is changed to alanine, for cloning convenience.

Figure 31:
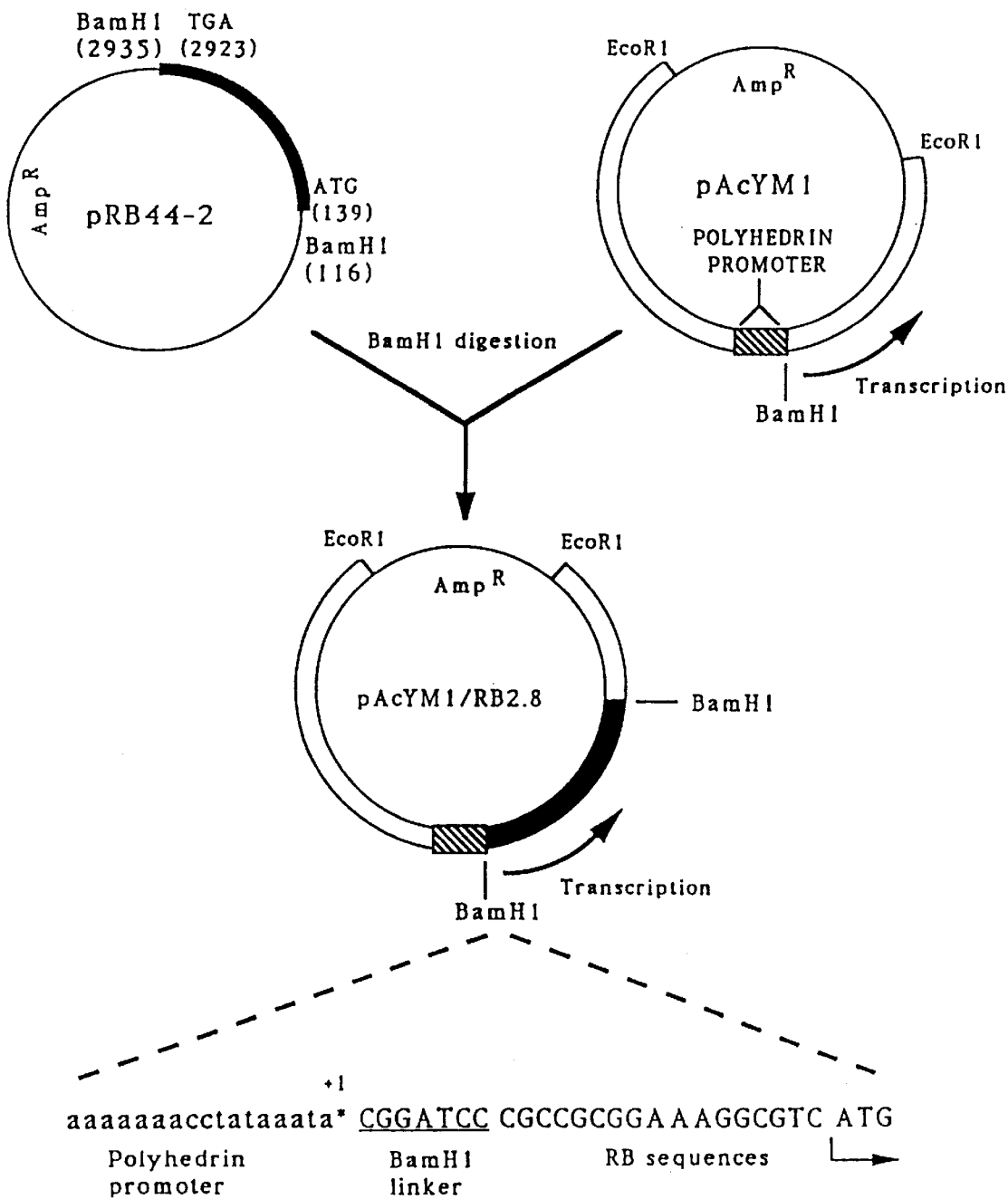

FIG. 31 is a diagrammatic representation of the construction of the baculovirus expression vector for pp110$^{RB}$ synthesis.

Figure 32A:
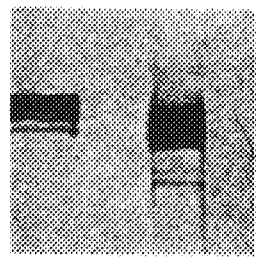
Figure 32B:
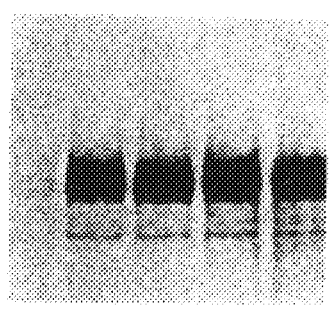

FIGS. 32A and 32B are western blots of ppRB infected insect cells (FIG. 32A) and a blot identifying cellular extracts from infected cells at up to 72 hours post-infection.

Figure 33:
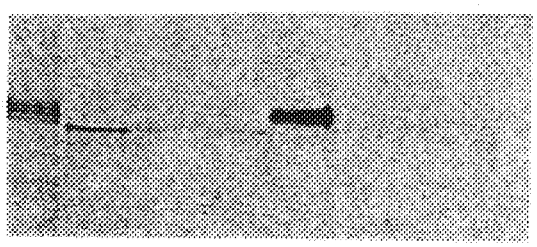

FIG. 33 is an autoradiograph depicting phosphorylation of RB protein in insect cells and the results of dephosphorylation analysis.

GENERAL DESCRIPTION

It is a primary object of this invention to provide generally safe and specific therapeutic methods and products useful for controlling progression of the cell cycle in organisms and controlling cancer suppression.

It is a further object of the present invention to provide a safe and effective method and composition for reversibly arresting cell cycle progression in organisms.

It is still further object of the present invention to provide a technique which may be used in combination with therapeutic methods to arrest tumorigenesis in organisms.

It is a further object of this invention to provide products and methods for controlling cancer suppression which are specific for suppression and eradication of a cancer tumor and which utilize biotechnical methods and products. It is a still further object of the present invention to provide a pharmaceutical composition for therapeutically treating cancer wherein the composition is functional at the cellular and intracellular levels.

It is still another object of this invention to provide a pharmaceutical composition for treating conditions caused by defective, mutant or absence cancer suppressor genes wherein the active ingredient of the composition is a natural or synthetically produced product.

The present invention comprises a method for cell therapy wherein a specific cancer suppressor gene protein product is delivered to the affected cell to accomplish tumor suppression.

The present invention provides a method for treating cancer which reduces the need for conventional radiation and chemotherapy. In addition, the inventive technique may be employed at a very early stage, after a genetic predisposition to cancer has been discovered, but before the onset of tumorigenesis.

A significant advantage of the present invention is that it uses a cancer suppressor gene protein product in a convenient, and relatively inexpensive manner to accomplish cancer suppression at the cellular level.

While there is some uncertainty as to whether inactivation of one or more cancer suppressing genes in a cell is sufficient to cause cancer, the cellular introduction of the gene protein product is a novel and advantageous approach to the treatment of malignancy. A further advantage of the present is that, unlike conventional, cytotoxic cancer therapies, the cell therapy herein disclosed accomplishes beneficial changes at the cellular levels, while minimizing trauma to the organism.

The present invention is a method of cell therapy wherein a specific cancer suppressor gene protein product is delivered to the affected cell to accomplish tumor suppression. A given cell may be defective in that it has a missing or defective gene thereby leading to a deficiency in protein expression in the cell.

The inventive method relates to using a gene protein product related to the defective gene. The purified protein product is delivered to the affected cell to accomplish, for example, tumor suppression. The product is delivered in a pharmacologically suitable carrier, thereby enabling the protein product to function at the cellular, or subcellular level.

As an example of such a method, an RB gene protein has been delivered to cells having a missing or defective RB gene, which is a cancer suppressor gene.

In the preferred example, retinoblastoma, a rare childhood cancer of the developing retina, is the prototypic model for studies of recessive oncogenesis. Based on the localization of the involved genetic element to chromosome 13q14, and evidence of its recessive nature, the putative cancer suppressor gene, retinoblastoma susceptibility gene (RB), was cloned. This gene contains 27 exons dispersed within 200 kilobases of genomic DNA and expresses a 4.7 kilobase mRNA transcript in all normal tissue examined. Sequence analysis of the complementary DNA clones revealed a long open reading frame that could encode a hypothetical protein of 928 amino acids. Using antibodies raised against selected epitopes predicted from the RB cDNA sequence, the RB gene product has been identified as a nuclear phosphoprotein with relative molecular mass (Mr) of 110,000–114,000, and was named $pp110^{RB}$.

In addition to retinoblastoma, the loss of RB gene function has also been implicated in the development of several other tumor types, including breast cancer, osteosarcoma, prostate cancer and small cell lung carcinoma. The recent demonstration that the reintroduction of RB gene, via retrovirus-mediated gene transfer, into retinoblastoma, osteosarcoma or prostate carcinoma cells apparently suppresses several aspects of their neoplastic phenotype, including tumorigenicity in nude mice, provides direct evidence for the tumor suppression function of the RB gene. However, the molecular basis of this biological activity has not been defined to date.

Until the present time, elucidation of the biochemical properties and biological functions of cancer suppressor gene products has been hampered by difficulty in obtaining sufficient quantities of such protein because of its low abundance in cells.

A cell therapy method has been invented for the delivery of specific gene protein product to cells having defective or absent genes. Utilizing the present invention, appropriate amounts of substantially purified, intact and biochemically active gene product proteins can be delivered to defective cells in therapeutically effective dosages.

The cell therapeutic methods of the present invention has broad applications. The protein product has utility, not only in the treatment of defective cells but in the elucidation of gene functions as the genes interact with one another at the cellular level.

A specific example is provided, wherein the retinoblastoma gene protein product, $pp110^{RB}$, has broad application for treatment of eucaryotic cells having a defective, or missing, RB gene.

It was found that the purified protein can bind DNA and form a specific complex with SV40 T antigen in the same way as the authentic human $pp110^{RB}$. The prompt nuclear translocation of the protein after microinjection further suggests the active nature, and therapeutic applications for the purified gene product protein.

It is a further object of the present invention to provide a cell cycle controlling composition and method of using the same for controlling the progression of the cell cycle in living organisms.

It is a further object of the present invention to provide a safe and effective method and composition for reversibly arresting cell cycle progression in organisms.

It is a still further object of the present invention to provide a technique which may be used in combination with therapeutic methods to arrest tumorigenesis in organisms.

Thus, the present invention includes a method and compositions for controlling cell cycle progression, by introducing into a cell to be controlled, during the interphase of the cell, a cycle regulating composition. The composition is selected from the group consisting of a gene protein product and a fragment of the protein, to alter reversibly the cell cycle progression of the cell while maintaining its viability. The protein fragments have been found to have the unexpected and surprising characteristic of being soluble in low concentration of glycerol, thereby enhancing their value in pharmaceutical applications.

An advantage of the present invention is that cell cycle progression can be reversibly arrested in a convenient and safe manner, without insult to the organism. Thus, tumorigenesis may, for example, be controlled.

A further advantage of the present invention is that the composition utilized for cell cycle progression control is relatively inexpensive and readably obtainable.

A still further advantage of the present invention is the fact that the composition therein utilized possesses little or no toxic effects on healthy cells, and may be used in conjunction with other methods of cancer treatment.

An additional advantage of the present invention is the fact that the compositions and techniques are compatible for use with the regulatory regimens and are physiologically compatible with other methods and devices for regulating certain physiological processes of the body such as blood cell production and gamete production.

DETAILED DESCRIPTION OF THE INVENTION

Thus, this invention provides a method of preventing or inhibiting the proliferation of a pathologically proliferating cell, wherein the pathological proliferation of the cell is the result of an absence of a functional retinoblastoma polypeptide or protein in the cell, comprising contacting the cell with an effective amount of retinoblastoma polypeptide or protein, thereby preventing or inhibiting the proliferation of the cell.

As used herein, the term "inhibiting the proliferation of" is intended to be a reduction in the rate of replication of the target cell. In one embodiment, this reduction is characterized by apoptosis or death of the target cell. In a separate embodiment, this reduction is characterized by the target cell being transformed from a malignant phenotype to a differentiated, mature or benign phenotype. The loss of the functional protein or polypeptide can occur by mutation (as defined below) of the retinoblastoma gene or allele or by mutation affecting the expression of the gene, such that a subnecessary concentration is expressed.

As used herein, the term "mutated" is defined as altered forms that are commonly found in nature or the one arbitrarily designated as normal. Genetic mutation can be gross deletions, point deletions, additions, substitutions and translocations. All of these genetic alterations at the 13q14 locus have been implicated in retinoblastoma and pathologies secondary to retinoblastoma.

This invention also provides therapeutic and prophylactic regimens for patients having non-ocular malignancies, cancers, or tumors, whose presence has been associated with a mutated RB protein. For example, individuals with hereditary susceptibility to retinoblastoma who have never contacted the disease or been cured, are at a higher than normal risk of contacting certain other non-ocular primary cancers. These non-ocular primary cancers, for the purposes of this invention are termed "secondary retinoblastoma-linked cancer" or a pathology "secondary to retinoblastoma."

"Secondary retinoblastoma-linked cancer" includes sporadic bilateral cases wherein two independent mutational events occur on each allele of 13q14 resulting in a pathologically mutated RB protein. Examples of secondary retinoblastoma-linked cancers or tumors include, but are not limited to, osteosarcoma, bone cancer, synovial sarcoma, breast cancer, small cell and non-small cell lung carcinomas, bladder carcinoma, renal cell carcinoma, gastric cancer, prostate carcinoma, leukemia, cervical carcinoma, fibrosarcoma, glioblastoma, acoustic neuroma, chronic lymphocytic leukemia, and acute myelogenous leukemia.

At the clinical level, this invention is intended to provide a prophylaxis and/or treatment for cancers, tumors or malignancies, the presence of which is the result of an absent or pathologically mutated RB protein in cells of the tumor or cancerous tissue. As is known to those of skill in the art, cancer is defined as a class of diseases of animals characterized by uncontrolled cellular growth, e.g., leukemia, lymphoma, sarcoma, carcinoma, teratoma, metastasis and neoplasm. A tumor is a clump of cells due to abnormal proliferation. Thus, this invention provides a therapy to stop the uncontrolled cellular growth in the patient thereby alleviating the symptoms of the disease or cachexia present in the patient. The effect of this treatment and/or prophylaxis includes prolonged survival of the patient, reduction in tumor mass or burden or the reduction of the number of circulating tumor cells.

It is also within the scope of this invention to combine the protein therapy with traditional therapies, such as surgery, chemotherapy and radiation treatments to treat tumors and cancers.

For the purpose of this invention, the terms "patient" and "subject" are synonymous and are intended to include human patients as well as vertebrate subjects, such as mammals.

At the cellular level, this invention provides a method of preventing or inhibiting uncontrolled cellular growth related to the absence of a normal or wild-type RB protein in the cell. In other words, the RB protein is pathologically mutated resulting in the loss of functional retinoblastoma protein in the cell.

Thus, this invention provides a method of preventing or inhibiting the proliferation of a pathologically proliferating cell, wherein the pathological proliferation of the cell is the result of an absence of a functional retinoblastoma polypeptide or protein in the cell, by contacting the cell with an effective amount of functional or biologically active retinoblastoma polypeptide or protein, thereby preventing or inhibiting the proliferation of the cell.

When used prophylactically, the method prevents uncontrolled cell growth or pathological proliferation of the cell. Because a tumor or cancer to be treated contains a large number of cells (sometimes of different cell types) at various stages of growth and division, certain cells within a tumor contacted with the RB protein are prevented from uncontrolled growth while simultaneously, others are inhibited from uncontrolled growth.

The term "pathologically proliferating cell" is intended to include but is not limited to cells having the capacity for autonomous growth, i.e., existing and reproducing independently of normal regulatory mechanisms. These cells are pathologic because they deviate from normal cells, whether or not associated with a diseased state. Examples of such cells include, but are not limited to, a retinal cell, a prostate cell, a psoriatic cell, a thyroid cell, a breast cell, a colon cell, a lung cell, a sarcoma cell, a leukemia cell, or a lymphoma cell. Also intended are tumor cells characteristic of cancers such as retinoblastoma, osteosarcoma, fibrosarcoma, glioblastoma, breast cancer, lung cancer, transitional cell carcinoma of bladder, small cell lung carcinoma, non-small cell lung carcinoma, renal cell carcinoma, acoustic neuroma, for example.

The method of this invention requires contacting the cell with an effective amount of functional retinoblastoma protein or polypeptide. The contacting may be in vitro or in vivo. When the contacting is in vitro, it is done by removing a sample of cells from a subject and mixing the retinoblastoma protein or polypeptide with the cells. Alternatively, the RB protein may be microinjected into the cells. A culture of cells of a known type also are useful, especially for screening proteins believed to be a functional equivalent of RB protein, such as an RB protein mimetic. Alternatively, the polypeptide or protein can be added to cell culture medium which in turn is then added to the sample of cells. The in vitro method is useful as an assay to determine if the protein therapy of this invention is useful to treat a subject's uncontrolled cellular growth or tumor. If the cells are inhibited in vitro, the examples provided below show that there is a direct correlation between in vitro efficacy of the method and in vivo efficacy of the method. Alternatively, a sample of the suspected tissue can be administered to a mouse or rat and allowed to form a tumor in the animal. The RB protein or polypeptide can be administered to the animal to determine if this protein therapy will be effective in the patient alone, or in conjunction with traditional anti-cancer therapies. If effective, the same or similar course of treatment can be utilized with the patient. Thus, the successful use of the therapy at the cellular or tissue level is predictive of the therapeutic utility of the method in a patient having hyperproliferative cells present, for example, in a tumor or cancer.

It is generally recognized that, after mitosis of a somatic cell is completed, at the end of telophase, the cell enters into an interphase which, depending on a variety of factors, may be of short duration or last for a long period of time. Thus, for example, after cell differentiation and development of nerve tissue, the nerve cells may have a very long interphase. Conventionally, cellular interphase may be regarded as having three stages: G1 in which cell growth occurs without DNA replication, S phase, in which DNA replication occurs, and G2, in which DNA replication has been completed and the cell prepares for division. As hereinafter described in greater detail, certain gene protein products, or fragments thereof, have the capacity for controlling progression through the cell cycle by stopping reversibly the progression at G1. According to the present invention, cell cycle controlling compositions were introduced into cells during the interphase portion of their cell cycles, to cause a reversible alteration of the cell cycle progression, while maintaining cell viability. After a certain time, when the compositions degraded sufficiently within the cell, the cell cycle has been observed to be reinstated with the cell progressing toward subsequent stages of interphase.

With regard to pathological conditions in an organism, such as tumorigenesis, there is a manifestation of unwanted cell cycle acceleration, in some cells. As more fully discussed below, cancer suppressor gene protein products, such as the RB protein, or a fragment thereof, were utilized to arrest Saos-2 osteosarcoma cells in the G1 stage of interphase. It has been found that the administration of the protein to the cells had no toxic effect on the cells, and was reversible.

It follows then that, the method of this invention is useful for treating a patient having, or susceptible to, a retinoblastoma-related pathology or malignancy by administering an effective amount of the RB protein or polypeptide to the patient. Thus, this method is useful to treat a pathology characterized by a cell's inability to express a functional retinoblastoma polypeptide or protein by contacting the cell with a functional retinoblastoma polypeptide.

Separately, the animal having a retinoblastoma-related pathology can be utilized to test new drugs or therapies (an assay system) to be used in conjunction with the protein therapy described herein.

When the contacting is effected in vivo, the polypeptide or protein is first mixed with a pharmaceutically acceptable carrier for administration. A "pharmaceutically acceptable carrier" is intended to include, but not be limited to any of the standard pharmaceutical carriers, such as phosphate buffered saline, water, glycerol, mannitol, sucrose human serum albumin, Tween 80, Tris, sodium carbonate and emulsions, such as oil/water emulsions and various types of wetting agents.

As used herein, the term "administering" for in vivo purposes means providing the subject with an effective amount of the RB polypeptide or protein, effective to prevent or inhibit proliferation of the target cell or growth of the tumor. Methods of administering pharmaceutical compositions are well known to those of skill in the art and include, but are not limited to, intratumoral injection, oral administration, intravenous administration or parenteral administration. Administration can be effected continuously or intermittently throughout the course of treatment. Methods of determining the most effective means and dosage are well known to those of skill in the art and will vary with the protein or polypeptide used for therapy, the purpose of the therapy, the cell or tumor being treated, and the subject being treated. As an example, a suitable dosage range is from about 0.1 mg/kg/body weight to about 10 mg/kg/body weight.

As used herein, a "functional retinoblastoma protein" is intended to encompass naturally occurring retinoblastoma protein isolated from human cell lines as shown in the examples below or recombinantly produced retinoblastoma protein, for example, encoded by the cDNA shown in FIG. 2. In one embodiment of this invention, the retinoblastoma protein is the protein designated pRB$^{110}$.

The amino acid sequence of pRB$^{110}$ is shown in FIG. 2. Also included within this definition are functional equivalents of purified retinoblastoma protein or recombinantly produced protein pRB$^{110}$. A functional equivalent is a protein having an amino acid sequence different from purified retinoblastoma or pRB$^{110}$ but having the ability to produce the same phenotypic effect. These equivalent proteins can have additions, deletions or substitutions that do not substantially affect the ability of the protein to inhibit cell proliferation. A method of determining equivalent proteins is by the in vitro assay described above. Equivalent proteins or polypeptides include fragments of purified retinoblastoma protein or pRB$^{110}$. Examples of a biologically active fragments include, but are not limited to, p56$^{RB}$, and the fragments depicted in FIG. 2 from amino acids 393–772, 393 to 870 and 871 to 928.

A suitable cell for the practice of this invention is an animal cell; for example, a mammalian cell such as a human or mouse cell. Suitable subjects are mammals, such as mice or humans.

The above method is useful not only to inhibit the proliferation of a pathologically proliferating cell, but also is useful to prevent a cell susceptible to such proliferation. For example, patients with hereditary retinoblastoma are at risk for development of a secondary cancer, as defined above.

As is well known to those of skill in the art, an effective amount or dosage for prophylactic use can differ from a therapeutic amount or dosage, but can be determined by those of skill in the art.

This invention also provides a method for treating a pathology in a subject caused by the absence of a functional retinoblastoma protein or polypeptide, or the absence of or the presence of a mutated retinoblastoma gene. The method requires administering to the subject an effective amount of a functional retinoblastoma protein or polypeptide, as described above.

As is shown in more detail below, the RB gene protein product or the RB protein is an alternatively phosphorylated protein having an apparent molecular weight of about 110 kDa to 116 kDa on SDS-PAGE. It is present in normal, i.e., non-transformed, cells in a variety of vertebrate species.

In some cases, a pathologically or absent RB protein is the result of a mutation at the chromosomal locus of the RB gene. In a normal cell, the RB protein is the transcription product of a gene located at the 13q14 region. In familial cases of retinoblastoma, ("familial bilateral retinoblastoma") a mutation in one allele of this gene in the embryonic retina eventually leads to a retinoblastoma tumor in the developing child. For the unilateral or bilateral form of the disease that has no familial disposition, somatic mutations affecting both alleles must occur in the same retinoblast. See *Proc. Natl. Acad. Sci. USA* (1971) 68:820–823. However, this invention provides therapeutic and prophylactic regimens for unilateral and bilateral retinoblastomas caused by these mutations.

The RB protein is a alternatively phosphorylated protein that can be affinity-purified from cellular extracts. Due to variations in the phosphorylation of the protein, it migrates as a diffuse band of molecular weight 110 to 114 kDa on SDS-PAGE. Phosphorylation of the RB protein occurs on serine and threonine. (*Cell* (1989) 56:57–65 and *Oncogene Res.* 1:205–214); this property oscillates during the cell division cycle. The underphosphorylated forms predominate in the $G_o$ and $G_1$ phases of the cell cycle while the more highly phosphorylated forms predominate in the $G_2$, M, and S phases. For a general review of the biological properties of the RB protein see *Biochemica Biophysica Acta* (1993) 1155:43–61. Phosphorylation of the RB protein oscillates during the cell division cycle. As used herein, the term "RB protein" is intended to encompass all variously or alternatively phosphorylated forms of the protein. In certain embodiments, more than one form will be used in the methods of this invention and alternative forms can be administered simultaneously.

As used herein, a "functional retinoblastoma protein", "RB protein" or "RB polypeptide" also is intended to encompass naturally occurring retinoblastoma protein isolated from human or vertebrate cell lines as shown in the examples below or recombinantly produced retinoblastoma protein, for example, encoded by the cDNA shown in FIG. 2 in procaryotic and eucaryotic expression systems. In one embodiment of this invention, the retinoblastoma protein is the protein designated ppRB$^{110}$. The amino acid sequence of ppRB$^{110}$ is shown in FIGS. 2 and 30. As used herein, the term "purified" or "substantially purified" refers to the approximate level of purity obtained by the experimental procedures described below. Purity can be measured by any known method in the art, such as by gel imaging or using a densitometer.

Also included within this definition are functional equivalents of purified retinoblastoma protein (ppRB$^{110}$) or recombinantly produced protein pRB$^{110}$. As used herein, a functional equivalent is a protein having an amino acid sequence different from purified retinoblastoma (ppRB$^{110}$) but having the ability to produce the same phenotypic effect. These equivalent proteins can have additions, deletions or substitutions that do not substantially affect the ability of the protein to inhibit uncontrolled cell proliferation. A method of determining equivalent proteins is by the in vitro assay described above. Equivalent proteins or polypeptides include fragments of purified retinoblastoma protein or p110$^{RB}$. Several examples of these fragments were described above.

As used herein, the term "recombinant RB protein or polypeptide" is defined as the product of recombinant expression of a cDNA (as shown in FIG. 2) or fragment thereof, in recombinant expression system. A recombinant expression system is a recombinant expression vector stably transformed into a suitable host cell for the recombinant production of RB protein.

"Recombinant expression vector" includes vectors which are capable of expressing DNA sequences contained therein, where such sequences are operatively linked to other sequences capable of effecting their expression. Exemplified below are several expression vectors. It is implied, although not always explicitly stated, that these expression vectors must be replicable in the host organisms either as episomes, as an integral part of the chromosomal DNA, or as a separate chromosome. In sum, "vector" is given a functional definition, and any DNA sequence which is capable of effecting expression of a specified DNA sequence disposed therein is included in this term as it is applied to the specified sequence.

"Host-vector system" refers to host cells which have been transfected with vectors constructed using recombinant DNA techniques. Insertion of the vector or DNA can be accomplished by microcell transfer, retrovirus- mediated gene transfer, transfection, cell fusion, etc. The vectors and methods disclosed herein are suitable for use in host cells over a wide range of procaryotic and eucaryotic organisms.

Reference is made to standard textbooks of molecular biology that contain definitions and methods and means for carrying out basic techniques, encompassed by the present invention. See, for example, Maniatis et al., *Molecular Cloning: A Laboratory Manual*, Cold Spring Harbor Laboratory, New York (1982) and Sambrook et al., *Molecular Cloning: A Laboratory Manual*, Cold Spring Harbor Laboratory, New York (1989) and the various references cited therein.

In addition, recombinant DNA methods currently used by those skilled in the art include the polymerase chain reaction (PCR) which, combined with the synthesis of oligonucleotides, allows easy reproduction of DNA sequences. A DNA segment of up to approximately 6000 base pairs in length can be amplified exponentially starting from as little as a single gene copy by means of PCR. In this technique, a denatured DNA sample is incubated with two oligonucleotide primers that direct the DNA polymerase-dependent synthesis each afford an approximate doubling of the amount of target sequence. Each cycle is controlled by varying the temperature to permit denaturation of the DNA strands, annealing the primers, and synthesizing new DNA strands. The use of a thermostable DNA polymerase eliminates the necessity of adding new enzyme for each cycle, thus permitting fully automated DNA amplification. Twenty-five amplification cycles increase the amount of target sequence by approximately 10$^6$-fold. The PCR technology is the subject matter of U.S. Pat. Nos. 4,683,195, 4,800,159, 4,754,065, and 4,683,202.

Thus, the nucleic acid molecule (shown in FIG. 2) or a fragment thereof, can be inserted into an expression vector and utilized for the recombinant expression of RB protein. The recombinant protein is purified and used in the methods of this invention.

A suitable cell for the practice of this invention is an animal cell; for example, a mammalian cell such as a human, rat, or mouse cell. Suitable subjects are therefore animals and mammals, such as rats, simian, mice or humans.

The above method is useful not only to inhibit the proliferation of a pathologically proliferating cell, but also is useful to prevent a cell susceptible to such proliferation from uncontrolled cellular growth. For example, patients with hereditary retinoblastoma are at risk for development of a secondary cancer, as defined above. This method is particularly applicable to use in these patients.

As is well known to those of skill in the art, an effective amount or dosage for prophylactic use can differ from a therapeutic amount or dosage, but it easily can be determined by those of skill in the art.

This invention also provides a method for treating a pathology in a subject caused by the absence of a functional retinoblastoma protein or polypeptide, or the absence of or the presence of a mutated retinoblastoma gene. The method requires administering to the subject an effective amount of a functional retinoblastoma protein or polypeptide, as described above.

The following examples are intended to illustrate, but not limit the invention.

I. ANTI-RB ANTIBODIES AND RB PROTEIN PURIFICATION

Using the method of chromosomal walking from other chromosome 13 markers, retinoblastoma gene and encoding of the amino acid sequence was identified at 13 chromosome, 13q14:11 region. By using esterase D cDNA clones and by screening the genomic and cDNA libraries, several clones were obtained. From these clones, two cDNA overlapping clones RB-1 (about nucleotide 100 to about nucleotide 1,700 as shown in FIG. 2) and RB-2 (about nucleotide 100 to about nucleotide 1,000 as shown in FIG. 2) of 1.6 kb and 0.9 kb, respectively, were identified in human cDNA libraries. Later on, another clone RB-5 (about nucleotide 1,250 to about nucleotide 4,757 as shown in FIG. 2) also was identified.

The RB-1 clone was hybridized with 4.8 kb mRNA transcript in human fetal retina and placenta. In retinoblastoma samples, RB-1 clone either detected an abnormal mRNA transcript or the mRNA transcripts were not observed at all. Subsequently identified RB-5 clone, with a 3.5 kb insert, gave identical results as RB-1 in mRNA hybridization. Restriction enzyme analysis suggested that RB-5 and RB-1 clones overlapped in a 0.4 kb region and both together defined a DNA segment of about 4.6 kb, a size close to that of the normal RB mRNA transcript.

Nucleotide sequence analysis of clones RB-1 and RB-5 was performed by the dideoxy-terminator method described in *Proc. Natl. Acad. Sci.* (1977) 74:5463–5467 and yielded the reconstructed complete cDNA sequence. Different deletion templates were generated by the "cyclone" method (Ibid) in single stranded M13 phage clones, which yielded greater than 95% of the sequence. The remaining gaps were sequenced by primer extension in both strands. The complete sequence identified in this way contained 4,523 nucleotides.

An open reading frame was present from the 5' end to base 2688, with numerous additional in-frame stop condons further downstream. Translation from the first methionine codon (base 241) yielded a hypothetical protein of 816 amino acids (94,000 daltons in size). The second in-frame methionine was at base 346. Since the nucleotide sequence surrounding the first ATG is not typical of other known mRNA (*Nucleic Acid Res.* (1984) 12:857–863), the start condon assignment was regarded as tentative. A computer search of the National Biological Research Foundation protein sequence database detected no strong homology with any of more than 4000 published amino acid sequences. However, a number of nucleic acid-binding proteins and viral proteins showed weak sequence homology, with a yeast DNA-directed RNA polymerase (*Cell* (1985) 42:599–610) having the highest homology score.

The predicted protein sequence included ten potential glycosylation sites (*CRC Crit. Rev. Biochem.* (1981) 10:307–366) but a candidate transmembrane domain (at least 20 consecutive hydrophobic residues) was not found. The amino acid hydropathy plot showed a mildly hydrophobic region near the putative amino terminus and a hydrophilic region at the carboxyl terminus. Two pairs of short amino acid sequences were identified that were bracketed by cysteine and histidine residues in the manner of a metal-binding domains found in nucleic acid-binding proteins (*Science* (1986) 232:485–487). A region of 54 amino acids from position 663 to 716 contains 14 proline residues or about 26% such proline-rich regions had also been observed in nuclear oncogene proteins myc and myb (*RNA Tumor Viruses* (1985) Cold Spring Harbor Laboratory, Cold Spring Harbor).

While the early significance of these observations is not well established, they suggested that the RB gene product may be a nucleic acid-binding protein. Taking into consideration the previous findings, and the fact that the nucleotide sequence analysis of RB cDNA clones demonstrated a long-open reading frame encoding a hypothetical protein with features suggestive of a DNA binding function, it was an initial object of this work to identify and characterize the RB protein to be used as an antigen for obtaining specific antibody and to determine its predicted DNA binding.

RB protein antigen was prepared by expressing the fusion protein in *E. coli*. For that purpose, a 20 kb polypeptide fragment of the RB gene was fused with TRP E protein and the fusion protein has been expressed in *E. coli*.

From the hypothetical RB protein sequence data with 816 amino acids and molecular weight of approximately 98 kD, three pATH plasmids that express TRP E fusion protein were constructed. The complete cDNA clone was divided into three portions, namely into fragments 0.7 kb, 0.9 kb and 1.8 kb. These three fragments contained the coding sequence of RB cDNA. Plasmid pATH3–0.9 RB was constructed from the fragment 5' 0.9 kb inserted into EcoRI-EcoRI site of pATH3. Plasmid pATH3-0.7 RB was constructed by inserting middle 0.7 kb fragment of RB-1 clone into EcoRI-EcoRI site of pATH3, and the plasmid pATH3-1.8 RB was constructed by inserting 3' 1.8 kb fragment into Bg1II-Bg1II site of pATH3 vector. Orientation was confirmed by detail mapping of the restriction enzyme sites.

The recombinant plasmids pATH3-0.9RB, pATH3-0.7RB and pATH3-1.8RB were then transformed into *E. coli* mm 294 and grown in M9 minimal medium which was supplemented with tryptophan preferably of concentration of about 20 mg/ml. The culture mixture was diluted from 1:10 to 1:150, preferably 1:100, with M9 medium, with casamino acids and ampicillin added. The procedure for recombinant plasmid construction is described in *J. Virol.* (1984) 49:132–141. The fusion of the fragments into pATH vector frames at the site of restriction enzymes is described in *Proc. Natl. Acad. Sci.* (1986) 83:4685–4689.

Only one of the three pATH3 constructs, namely pATH3–0.7RB expressed the fusion protein. The obtained fusion protein had a molecular weight of 57 kD. Since the molecular weight of TRYP E is known to be 37 kD, 20 kD protein portion of the fusion protein was derived from the RB.

The other two plasmid constructs produced no protein at all, not even TRYP E itself. Since RB clones contain many hypothetical protease cleavage sites, the inability to produce protein in *E. coli* was not surprising and was probably due to instability of the fusion protein.

Using the above described procedure for fusing pATH3 with RB fragment, large quantities of the fusion protein were prepared and purified by preparative SDS polyacrylamide gel electrophoresis according to procedure described in *Nature* (1970) 227:680–685. The fusion protein was eluted by overnight extraction and SDS and soluble acrylamide were removed by dialysis. The proteins were then concentrated.

Purified fusion protein was used as an antigen in generating specific anti-RB protein antibody.

The specific rabbit polyclonal antibody against RB protein were prepared by the procedure described generally in *Proc. Natl. Acad. Sci.* (1986) 83:6790–6794.

Rabbits were repeatedly injected, preferably at 14 day intervals with 1–2 μg, preferable 10 μg, of purified fusion protein mixed with complete Freund's adjuvant (initial injection) and then given booster injections of the same amount of the fusion protein in incomplete Freund's adjuvant (repeated injections). Complete Freund's adjuvant generally consists of an emulsion of the antigen, in this case the fusion protein, in saline and a mixture of an emulsifying agent, such as for example, Arlacel A, in mineral oil and killed mycobacteria. Incomplete Freund's adjuvant is the same except that it does not have the mycobacteria.

The injections were repeated until sufficiently high titer of anti-fusion protein was detected, approximately for two months, to react with both TRP E and the fusion protein. To enrich for antibodies recognizing only RB determinants, two or more affinity columns were prepared using a methods generally described in *Proc. Natl. Acad. Sci* (1951) 37:575–578, and in *Immunoadsorbents in Protein Purification, Scand, J. Immunol.* (1976) Suppl. 3. At least one column was loaded with TRP E protein and at least one column was loaded with the fusion protein. Both columns were appropriately precycled. Antibody was passed first through the fusion protein-Sepharose column and eluted with glycine buffer of pH 2.3. The eluate was neutralized and passed through the TRP E column several times to remove antibody specifically directed against TRP E. The purified anti-RB IgG antibody was used for immunoprecipitation or immunostaining, for localization of RB protein and will be equally useful for diagnostic identification of RB protein in human tissue samples.

To identify the RB protein, several human cell lines known to have either normal or altered RB gene expression were selected. LAN-1 neuroblastoma cell line, normal human fibroblasts, human hepatoma Alexander cell line and osteosarcoma U2OS cell line were used as positive controls containing normal RB mRNA. All these cells were obtained from the American Type Culture Collection (ATCC) depository. Cell lines with expected shortened or absent RB mRNA, such as retinoblastomas cell lines Y79 (ATCC), RB355 (gifted from Robert Philips, Toronto, Canada), WERI-1, WERI-24, and WERI-27 (gifted from T. Sery Wills' Eye Hospital, Philadelphia) were used as negative controls.

All normal human cell lines as described above and all cells from five retinoblastomas were labeled with $^{35}$S-methionine and immunoprecipitated with preimmune rabbit antibody IgG or rabbit anti-RB IgG.

Cells from all human cell lines were metabolically labeled with $^{35}$S-methionine according to procedure described in *J. Virol.* (1981) 38:1064–1076. Labeled cell mixtures were immunoprecipitated with 1–20 $\mu$l, preferably 10 $\mu$l, of from 50 $\mu$g/ml–200 $\mu$g/ml, preferably 100 $\mu$g/ml of anti-RB antibody IgG using the procedure described in *J. Virol.* (1981) 38:1064–1076.

In all control cell lines a protein doublet with apparent molecular weight of 110–114 kD was detected. In retinoblastoma cell lines, or in cells immunoprecipitated with preimmune serum the protein doublet was not detected.

Figure 1:
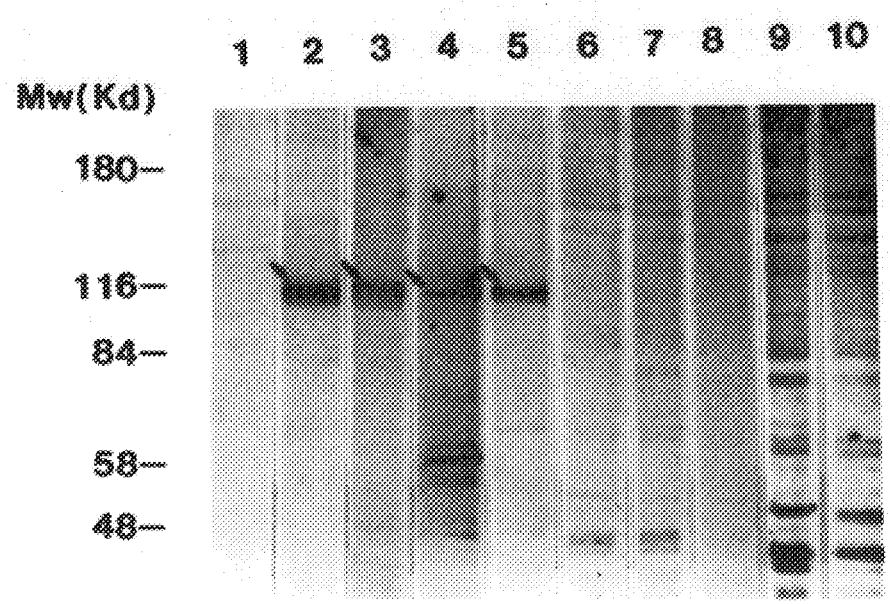

The RB proteins immunoprecipitated with rabbit anti-RB IgG were analyzed by SDS/polyacrylamide gel electrophoresis and into auto-radiographed. The results are shown in FIG. 1. The RB protein presence is visible at approximately 110 kD region in lanes 2–5 which illustrate the immunoprecipitation of the normal positive, i.e., RB protein containing cell lines labeled with $^{35}$S-methionine. Lane 1 is the control line of neuroblastoma cell immunnoprecipitated with the preimmune, hence without anti-RB protein antibody, rabbit IgG. Lanes 6–10 are obtained by immunoprecipitation of labeled $^{35}$S-methionine cell lines from five retinoblastomas. There is no RB protein present in any of these cell lines.

The absence of antigenically detectable RB protein in retinoblastoma cells supports the notion that oncogenicity by mutant RB genes is achieved through complete loss of gene product function even in those cell lines containing shortened RB mRNAs.

The hypothetical protein predicted from the nucleotide sequence was expected to have MW about 98 kD. The immunoprecipitated protein has a MW about 110–114 kD. Complete RB amino acid sequence is illustrated in FIG. 2. This complete sequence is obtained from the newly reconstructed clone which contains the most 5' end stretch missing in the original cDNA clone (*Science* (1987) 235:1394–1399). The first and second initiation methionines are boxed and alanine and proline clusters are underlined. The amino acid sequence (FIG. 2) is written in the single-letter abbreviation code recognized in the art.

The RB cDNA sequence (*Science* (1987) 235:1394–1399) contained a long open reading frame from nucleotide 1 through 2688, which is translated from the first methionine condon yields a hypothetical protein of 816 amino acids and molecular weight 98 kD. Another RB cDNA clone was isolated which contains an additional 234 base pairs on the 5' end. The revised RB cDNA sequence (FIG. 2) still maintains the same open reading frame as in the original clones, and an additional methionine condon was found at nucleotide 139. When this methionine was used as an initiation condon, the predicted RB protein had 928 amino acids and a molecular weight of 110 kD—identical to the apparent M.W. determined by SDS-PAGE. The additional 5' sequence contains a GC-rich region that translation into an unusual cluster of alanine and proline residues (FIG. 2).

Discrepancies between actual and apparent molecular weights on SDS-PAGE may be explained by secondary protein modifications. Several potential N-linked glycosylation sites are present in the predicted amino acid sequence seen in FIG. 2. However, when LAN-1 cells were grown in medium supplemented with $^{14}$C-galactose or $^{3}$H-glucosamine, labeled RB protein was not detected despite prolonged autoradiography. In addition, digestion of $^{35}$S-labeled RB protein by Endoglycosidase H according to method described in *J. Biol. Chem.* (1975) 250:8569–8579, did not result in a reduction of apparent molecular weight.

Figure 3:

When the neuroblastoma cells LAN-1 were metabolically labeled with $^{32}$P-phosphoric acid and immunoprecipitated, the immunoprecipitated protein ran as a single band with molecular weight identical to the 35S-labeled RB protein. The results, illustrated in FIG. 3, shows lanes 2 and 3 showing a $^{35}$S-labeled band at 110–114 kD and lane 5, showing a $^{32}$P-labeled band at 110–114 kD. Lanes 1 ($^{35}$S) and 4 ($^{32}$P) are immunoprecipitated with preimmune rabbit IgG. When the aliquots of RB samples labeled with $^{35}$S-methionine were digested overnight with Endoglycosidase H, there was no detectable reduction of molecular weight 110–114 kD. The above findings prove that the purified retinoblastoma is a phosphoprotein of MW 110–114 kD. The phosphoprotein was therefore named ppRB$^{110}$.

Figure 4:
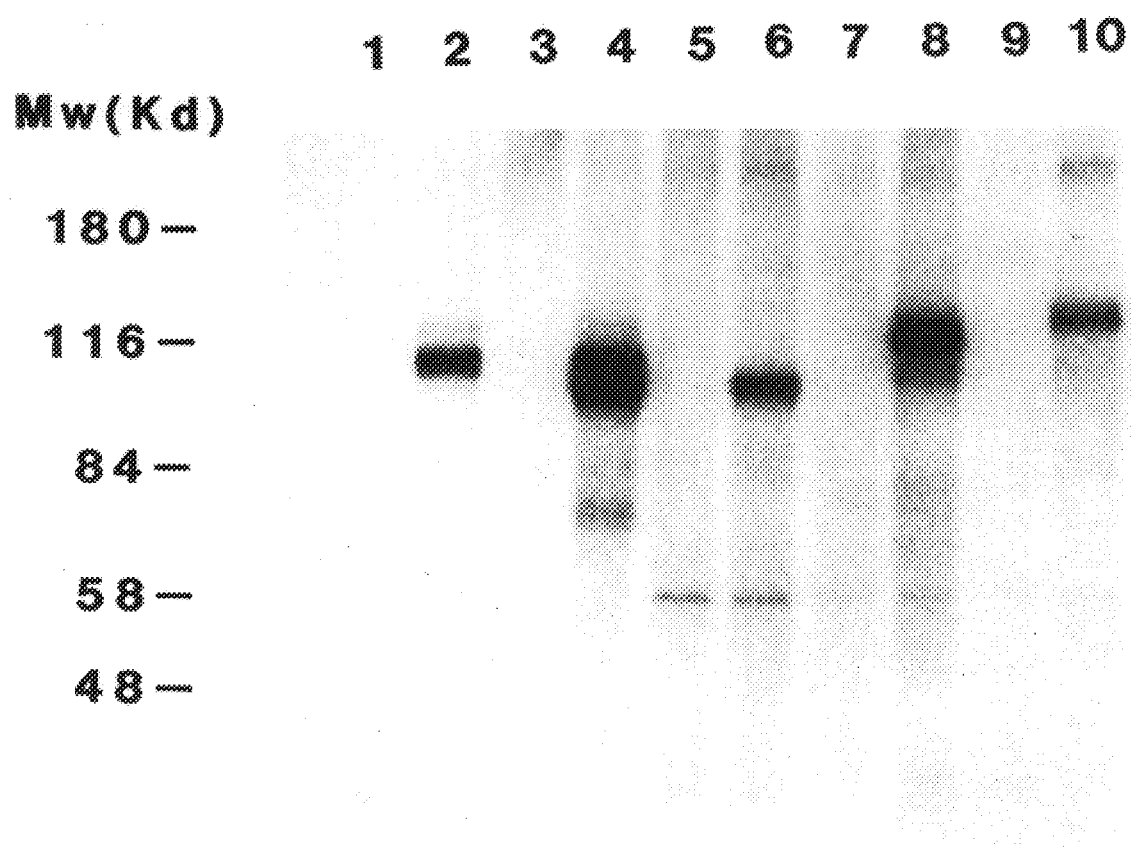

The RB gene was detected in other vertebrates at the DNA level (also described in *Science* (1987) 235:1394–1399 and FIG. 4) suggesting that the RB gene is present in many species during the evolution and further suggesting an important physiological role. The cells from several vertebrate species, such as QT6 (quail), NIH/3T3 (mouse), Rat-2 (Rat) and cos (monkey) were labeled with 32P-phosphoric acid as described previously and proteins were immunoprecipitated with anti-RB IgG using the same procedure as used for human cells. As shown in FIG. 4, antigenically related proteins were detected in all cells with apparent similar molecular weights of 108 kD in quail, 120 kD in mouse, 128 kD in rat and 108–110 kD in monkey, as compared to 110–114 kD in human cells.

Antigenically related proteins with varied molecular weights observed in different vertebrate species such as quails, mice, rats and monkeys suggest that the RB protein is conserved through the evaluation, most probably in proportion to evolutionary relatedness. Since both antigens and molecular weights are simultaneously conserved in these vertebrate species, it is likely that the RB gene product is present and functionally similar in other species as well.

The predicted whole amino acid sequence of the ppRB$^{110}$ protein has several characteristics similar to those appearing in other oncogenes. Therefore, the subcellular localization of the ppRB$^{110}$ was investigated by cellular fractionization.

Two methods were essentially employed to find out the distribution of ppRB$^{110}$ between the nuclear, cytoplasmic, or cell membrane fractions.

In agreement with the chemical characterization the ppRB$^{110}$ sequence suggesting possible DNA binding, it was determined that 85% of ppRB$^{110}$ was found in the nuclear fraction, with proportionally small amounts (less than 10%) of the ppRB[110] was located in membrane. There was no detectable presence in the cytoplasmic fraction.

Figure 5A:
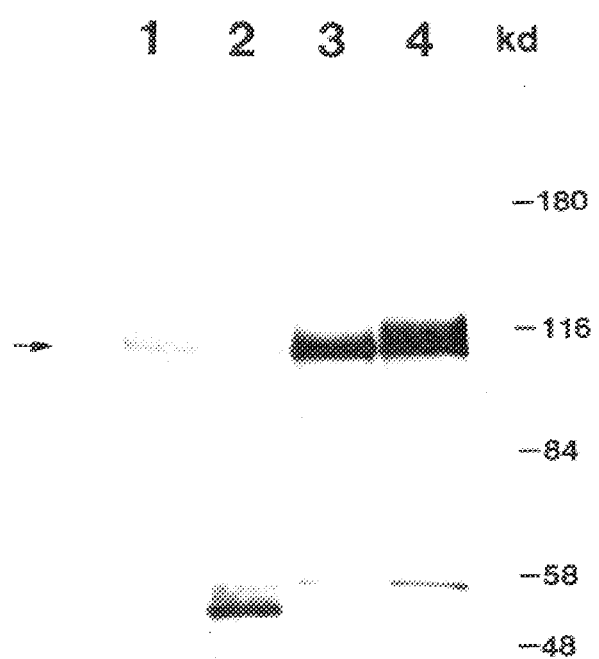
Figure 5B:
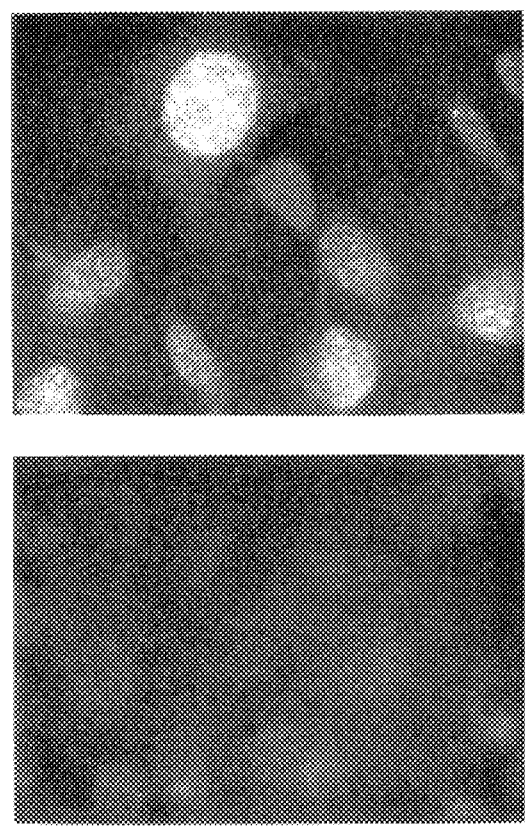

To further substantiate that the ppRB[110] is localized primarily in the nucleus, the osteosarcoma cell line U2OS known to have an advantageous cell morphology for immunohistochemical staining were used. As an experimental group, the U2OS cells were immunoprecipitated with anti-ppRB[110] IgG. As a control group, the U2OS cells were immunoprecipitated with preimmune IgG. Both groups were then incubated with rhodamine conjugated goat anti-rabbit IgG obtained commercially from Sigma. Immunofluorescence was observed in cells reacted with anti-ppRB[110] IgG, namely in the cell nucleus (FIG. 5B). Cells reacted with preimmune control did not show any fluorescence (FIG. 5Bii).

The subcellular localization of ppRB[110] in the nuclear fraction suggests that the RB protein plays an important regulatory function in regulating other genes and has a DNA—binding activity.

Certain cell lines, particularly those from tumors other than retinoblastoma, such as neuroblastoma LAN-1 cells were radioactively labeled with $^{32}$P-phosphoric acid. Cellular lysates of these labeled cell mixtures were separated by single or double stranded calf thymus DNA—cellulose columns according to the method described in *Mol. Cell. Biol.* (1986) 6:4450–4457.

The results obtained suggest that the ppRB[110] binds only to a limited number of DNA sites that are easily saturated. It has been previously shown that other proto-oncogenes such as c-myc, n-myc, c-myb and c-fos are nuclear phosphoproteins with DNA binding activity (*Mol. Cell. Biol.* (1986) 6:4450–4457; *Nature* (1982) 296:262–266). Oncogenic activation of these proto-oncogenes occurs by deregulation of gene expression or by structural modification, and the gene product is essential for oncogenicity.

The ppRB[110] absence, and not the presence, appears to be oncogenic due to the partial or complete inactivation of the RB gene. Therefore, the presence of the ppRB110 somehow suppresses the oncogenic activity of other genes and disallows the malignant cell growth. The ppRB[110] is therefore an important regulatory protein which can prevent and inhibit, by its presence, and trigger, by its absence, the malignant growth. Thus, the ppRB[110]'s importance is in regulating other genes. The absence or loss of ppRB[110] mediates oncogenicity.

The utility of the RB protein is several fold. First, the presence or absence of the ppRB[110] shall serve as a diagnostic tool in determination of presence or predisposition to retinoblastoma and other retinoblastoma-related non-ocular pathologies or tumors of the human and animal fetus, embryo or newborn babies. Such early diagnosis will allow an early warning and treatment of retinoblastoma and other tumors with the possibility of preventing development of the secondary tumor.

The diagnostic method disclosed also is particularly for useful screening families with the history of hereditary retinoblastoma. The diagnostic method, however, is also intended to be used for prophylactic prenatal and postnatal screening. Moreover, the diagnostic method also will be used for prediction of the development of secondary cancer, for example, osteosarcoma, fibrosarcoma, glioblastoma, breast cancer, etc., whether or not occurring in a patient who previously had a retinoblastoma tumor.

II. PREPARATION OF A RECOMBINANT RB FUSION PROTEIN AND ITS CHARACTERIZATION

Recombinant fusion protein was prepared for use as an antigen for immunization.

The conserved 5' 0.9 kb, middle 0.7 kb and 3' 1.8 kb regions of RB cDNA were subcloned into an inducible, high-level TRP E expression vector, pATH-3 (University of California, San Diego) using a standard procedure described in Maniatis et al. *Molecular Cloning: A Laboratory Manual* (1982) Cold Spring Harbor Laboratory, Cold Spring Harbor, N.Y.

Three RB cDNA subfragments containing the coding sequence, namely 5' 0.9 kb (EcoRI-EcoRI), middle 0.7 kb (EcoRI-EcoRI of RB-1) and 3' 1.8 kb (BglII-BglII) were fused in frame with pATH3 vectors, respectively. The TRP E-RB gene product of pATH3–0.7 plasmid was expressed in *E. coli* using a method described in *J. Virol.* (1984) 49:132–141. pATH3-0.7RB was constructed as illustrated in drawing 7A. cDNA RB fragment was inserted in-frame into the EcoRI endonuclease site of pATH-3 plasmid. Orientation was confirmed by detail restriction enzyme mapping. The recombinant plasmid was transformed into *E. coli* mm294 and grown in M9 minimal medium supplemented with 20 mg/ml of tryptophan. The culture was diluted to 1:100 in M9 plus casamino acids and ampicillin. At an optical density at 600 nm of 0.2, a 1:1000 dilution of a 10 mg/ml stock of indoleacrylic acid in 100% ethanol was added to induce the expression of the TRP E promoter.

Bacteria cells were pelleted and boiled in Laemmli gel sample buffer for 15 minutes and analyzed by polyacrylamide gel electrophoresis. Gel was then stained with Coomassie blue. Large quantities of fusion protein were prepared and purified through preparative polyacrylamide gel electrophoresis and eluted by overnight extraction. SDS and soluble acrylamide were removed by dialysis. The proteins were then concentrated and mixed with adjuvant for immunization of rabbits. About 6 mg protein was recovered which was subsequently used for immunization of rabbits.

Only one of the three pATH3 constructs, namely pATH3-0.7RB expressed the fusion protein. The obtained fusion protein had a molecular weight of 57 kD. Since the molecular weight of TRP E is known to be. 37 kD, 20 kD protein portion of the fusion protein was derived from the RB.

The other two plasmid constructs produced no protein at all, not even TRP E itself. Since RB clones contain many hypothetical protease cleavage sites, the inability to produce protein in *E. coli* was not surprising and was probably due to instability of the fusion protein.

The expression of *E. coli* produced, after induction, a 57 kD fusion protein comprising 20% of total *E. coli* protein. pATH-0.7 expressed a fusion protein with MW of 57 kD, of which 37 kD was TRP E and 20 kD was RB-derived.

Figure 7A:
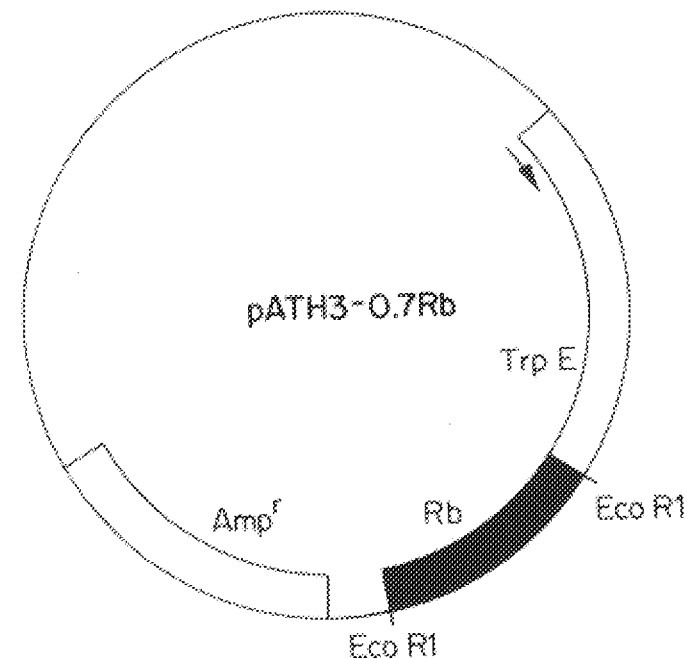
Figure 7B:
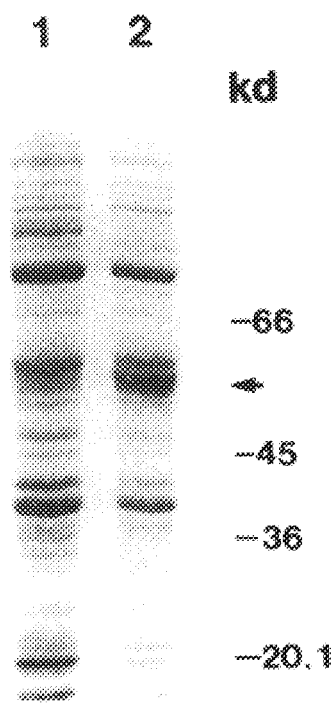
Figure 7C:
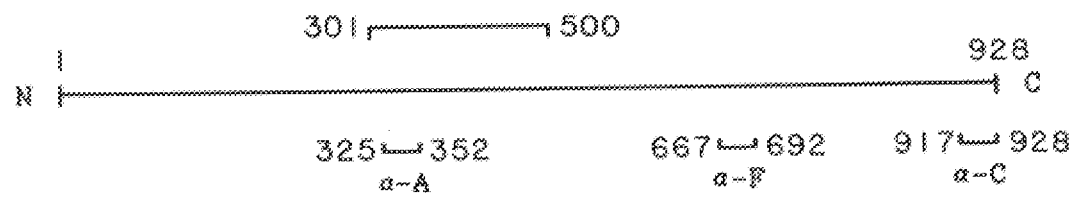
Figure 8B:
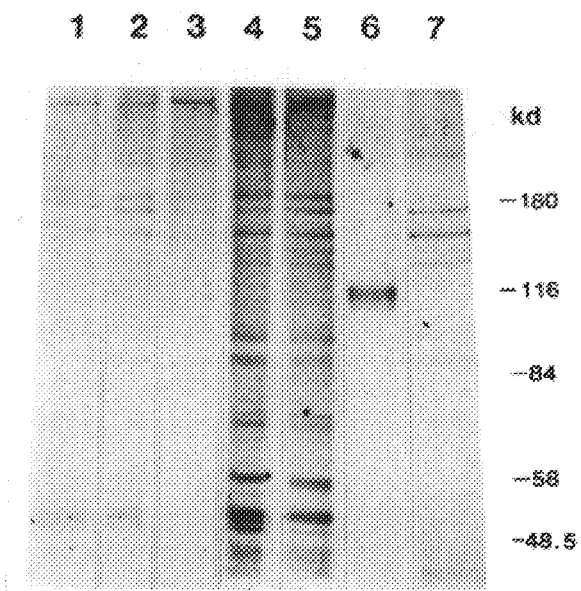
Figure 8A:
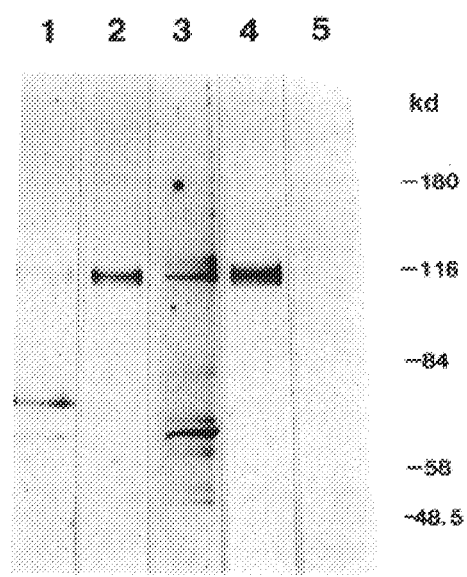

Production of the TRP E-RB fusion protein can be seen in FIG. 7A and the results of the PAGE/gel electrophoresis in 7B. A 58 kD protein was found in induction culture (Lane 2) but not control culture (Lane 2).

Using the above described procedure for fusing pATH3 with RB fragment, large quantities of the fusion protein were prepared and purified by preparative SDS polyacrylamide gel electrophoresis according to procedure described in *Nature* (1970) 227:680–685. The fusion protein was eluted by overnight extraction; SDS and soluble acrylamide was removed by dialysis. The proteins were then concentrated.

Purified fusion protein was used as an antigen in generating specific anti-RB protein antibody.

Anti$^{RB}$—Specific Antibody

The specific rabbit polyclonal antibody against RB protein were prepared by the procedure described generally in *Proc. Natl. Acad. Sci.* (1986) 83:6790–6794.

New Zealand Red rabbits were immunized with the TRP E-RB fusion protein obtained, as described above, following a standard protocol. Specifically, rabbits were repeatedly injected, preferably at 14 day intervals with 1–20 μg, preferable 10 μg, of purified fusion protein mixed with complete Freund's adjuvant (initial injection) and then given booster injections of the same amount of the fusion protein in incomplete Freund's adjuvant (repeated injections). Complete Freund's adjuvant generally consists of an emulsion of the antigen, in this case the fusion protein, in saline and a mixture of an emulsifying agent, such as for example, Arlacel A, in mineral oil and killed mycobacteria. Incomplete Freund's adjuvant is the same except that it does not have the mycobacteria.

Two months later, both rabbits produced high titers of antibodies that reacted with both TRP E and the fusion protein. The rabbits were bled and the blood was collected into plastic containers and clotted. The serum was obtained by centrifugation at 1000 g for 10 minutes. Rabbit anti-ppRB$^{110}$ immunoglobulin (IgG) was purified by passing the antisera through the two affinity columns. To enrich for antibodies recognizing only RB determinants, two affinity columns were prepared, one with TRP E protein and the other with the fusion protein. The antisera was passed through the fusion protein-Sepharose column and eluted with 0.1M glycine HCl buffer (pH 2.3). The eluate was passed through the TRP E column several times to remove antibody directed against TRP E using the same buffer. The elution was repeated several times. Antibody prepared through the above steps was serially diluted and the dilution sufficient for immunoprecipitation of RB protein in $1.5 \times 10^6$ cells were determined. This purified anti-RB antibody was used in all subsequent experiments for immunoprecipitation or immunostaining and to immunoprecipitate RB protein in several cell lines which were previously demonstrated to contain intact RB mRNA according to procedures set forth above.

Immunoprecipitation Identification of RB Protein With Anti-RB Antibody

A standard protocol was followed as described in *J. Virol.* (1981) 38:1064–1076.

LAN-1 neuroblastoma cell line, normal human fibroblasts, human hepatoma Alexander cell line and osteosarcoma (U20S) cell line which all contain normal RB mRNA were used as positive controls. All these cells were obtained from the American Type Culture Collection (ATCC) depository. Cell lines with expected shortened or absent RB mRNA, such as retinoblastomas cell lines Y79, RB355, WERI-1, WERI-24, and WERI-27 were used as negative controls. These cell lines were obtained as described above.

To label cellular proteins with $^{35}$S-methionine, about $1.5 \times 10^6$ cells in 60-mm petri dishes were starved by incubation at 37° C. for 30 minutes in methionine-free medium and then incubated in 3 ml of methionine-free medium supplemented with $^{35}$S-methionine (150 μCi/ml) for three hours. All subsequent operations were at 4° C. Cell extracts were prepared in lysis buffer containing 25 mM Tris-hydrochloride (pH 7.4), 50 mM NaCl, 0.2% Nonidet P-40, 0.5% deoxycholate and 200 units/ml of Aprotinin inactivator. 0.02% SDS was also added at the beginning of lysis. The lysates were clarified by centrifugation at 4° C. at 20,000×g for 15 minutes.

Immunoprecipitation was carried out with 5 μl of preimmune rabbit antisera, followed by absorption to formalin-fixed Staphylococcus aureus obtained from the Enzyme Center, Inc. To supernatant of each experimental sample was added 10 μl of 100 μg/ml of anti-ppRB$^{110}$ IgG and to supernatant of each control sample was added 10 μl of the preimmune sera for control. Protein A sepharose beads (Sigma) were then added. Immunoprecipitates were subsequently washed with 1) lysis buffer, 2) 1M NaCl in lysis buffer, 3) 0.15M NaCl in lysis buffer, and 4) lysis buffer to remove nonspecifically bound proteins. The immunoprecipitated proteins were analyzed by 7.5% SDS-polyacrylamide gel electrophoresis and autoradiographed. Gels of $^{35}$S-labeled proteins were fluorographed at −70° C. after impregnation with acetic acid-based 2.5-diphenyloxazole.

The results are illustrated in FIG. 1. The protein with MW 110–114 kD was found to be immuno-precipitated with anti-ppRB$^{110}$ IgG.

Characterization of the RB Gene Product

To further characterize the RB protein purified from cellular extract, the cells were labeled with $^{32}$P-phosphoric acid or with $^{14}$C or $^{3}$H-glucosamine and subsequently digested with Endoglycosidase H.

To test for protein phosphorylation, LAN-1 cells were metabolically labeled with $^{32}$P-phosphoric acid. To label LAN-1 cells with $^{32}$P, around $1.5 \times 10^6$ cells in 60-mm petri dishes were starved by incubation at 37° C. for 80 minutes in phosphate-free medium and then incubated for 1 to 2 hours in 2 ml of phosphate-free medium supplemented with 32PO$_4^3$-(1 m Ci/ml) medium. Cell extracts were prepared in lysis buffer containing 25 mM Tris-hydrochloride of pH 7.4, 50 mM NaCl, 0.2% Nonideb P-40, 0.5% deoxycholate and 200 units/ml of kallikrein inactivator obtained from Calbiochem. The lysate was clarified at 4° C. at 20,000×g for 20 minutes.

Immunoprecipitation was carried out with anti-ppRB$^{110}$ IgG according to standard procedure. Immunoprecipitate was absorbed to formalin-fixed Staphylococcus aureus obtained from the Enzyme Center and subsequently washed with 1) lysis buffer; 2) 1M NaCl, 10 mM Tris-hydrochloride (pH 7.4) and 0.1% Nonidet P-40; 3) 0.15 mM NaCl, 10 mM Tris-hydrochloride (pH 7.4), 0.1 Nonidet P-40; and 4) lysis buffer.

The immunoprecipitated proteins were prepared for electrophoresis following the procedure described in *J. Virol.* (1980) 36:617–621. Immunoprecipitated protein ran as a single band with molecular weight identical to that of $^{35}$S-labeled ppRB$^{10}$ protein indicating that the RB protein is a phosphoprotein.

Subcellular Localization of the Full Length RB Protein

Human neuroblastoma cells LAN-1 were labeled with $^{32}$S-methionine as described above, and fractionated into membrane, cytoplasm and nucleus. The labeled protein was subsequently immunoprecipitated with anti-RB IgG.

Cell fractionation protocol is essentially adapted from that described in *J. Cell. Biol.* (1983) 97:1601–1611. Two to five 100-mm plates containing a total of $2.0 \times 10^7$ to $7.5 \times 10^7$ LAN-1 cells were metabolically labeled with $^{35}$S-methionine for 2–3 hours prior to use. All subsequent procedures were performed at 4° C. Cells were rinsed twice with phosphate-buffered saline (PBS), scraped into PBS, and pelleted for 5 minutes at 375×g in a table top centrifuge. Half the cells were resuspended in lysis buffer for the whole cell lysate. The remaining cells were rinsed once in hypotonic RSB buffer (10 mM HEPES pH 6.2, 10 mM NaCl, 1.5 mM MgCl$_2$, 200 units/ml Aprotinin) and then resuspended in RSB. The cell suspension was homogenized by 20 strokes in a tight fitting Dounce homogenizer, and volume was adjusted to exactly 3 ml with RSB buffer. The homogenate was centrifuged at 1,500 rpm in a Sorvall HB4 rotor at 375×g for 10 minutes, and the pellet was resuspended in lysis buffer to generate the nuclear fraction. The supernatant was centrifuged in thick-walled polyallomer tubes in a Beckman SW50.1 rotor at 35,000 rpm (150,000×g) for 90 minutes. The pellet was resuspended in lysis buffer to generate the membrane fraction, while the supernatant was adjusted to 1×lysis buffer concentration to produce the cytoplasmic fraction. All four fractions were then assayed for RB protein content as illustrated above.

The immunoprecipitates were analyzed by 7.5% SDS-polyacrylamide gel electrophoresis and autoadiographed. The results are summarized and illustrated in FIG. 5A.

The following fractionation method also can be used. All procedures were performed at 0° to 4° C. Two to five 100-mm plates containing a total of 2.0×10$^7$ to 7.5×10$^7$ LAN-1 cells were rinsed twice with phosphate-buffered saline (PBS), scraped into PBS, and pelleted for 1 minute at 1,000×g in a clinical centrifuge. After the pellet was rinsed once with hypotonic TKM buffer (20 mm Tris pH 7.1, 5 mM KCl, 1 mM MgCl$_2$, 1% Aprotinin), the cells were dispersed and swollen in TKM for 15 minutes. The cell suspension was homogenized by 20 strokes in a tight fitting Dounce homogenizer. The volume was adjusted to exactly 3 ml with TKM buffer, and samples were removed for analysis by immunoprecipitation.

Nuclear pellet was generated by low-speed centrifugation, and the supernatant from this initial centrifugation was subjected to high-speed centrifugation to obtain a precipitate and a soluble fraction. To obtain a nuclear pellet, the homogenate was centrifuged at 1,500 rpm in a Sorvall HB4 rotor (375×g) for 10 minutes at 0° C., and the crude nuclear pellet was suspended in 1 ml of TKM. This pellet was then homogenized five times in the Dounce homogenizer and aspirated three times through a 1 ml syringe fitted with a 25-gauge needle. The suspension was then pelleted as described above, suspended in TKM buffer and aspirated again five times through the same syringe. After a final centrifugation, the nuclear pellet was suspended in TKM buffer and analyzed for RB protein content and for subcellular markers. The original postnuclear supernatant (PNS) and the supernatants from the nuclear pellet washes were pooled and centrifuged in thick-walled polyallomer tubes in a Beckman SW50.1 rotor at 38,000 rpm (150,000×g) for 90 minutes at 0° C. to generate particulate (P$_{150}$) and soluble (S$_{150}$) fractions. The fractions were then adjusted to equal volumes with TKM buffer and assayed directly for RB protein and subcellular markers.

Plasma membrane content was determined by measuring 5' nucleotidase. The samples were taken up in TKM buffer and incubated in an assay mixture containing 10 mM MgCl$_2$, 0.1 mM AMP, 100 mM glycine (pH 9.0), and 2 μCi of $^3$H-adenosine in the supernatant determined by liquid scintillation counting (Ibid). The soluble protein in each fraction was determined assaying for lactate dehydrogenase activity according to *Proc. Natl. Acad. Sci.* (1962) 48:2123–2130 and the endoplasmic reticulum content was measured with an assay for NADH diaphorase according to procedure described in *Biochem. Biophys. Acta.* (1971) 20 233:334–347.

The results are illustrated in FIG. 5B. Using methods of biochemical fractionation and immunofluorescence (described in the previous example), the RB protein was determined to be localized primarily in the nucleus. (The fluorescence was present mainly within the nucleus and the preimmune control was negative.)

A majority (about 85%) of $^{35}$S-labeled protein was located in the nuclear fraction while a minor portion (less than 10%) was associated with membrane. There was no detectable RB protein within the cytoplasmic fraction, or secreted into the medium.

Subcellular Localization of RB Protein Measured by Immunofluorescence

The human osteosarcoma cell line U20S, obtained from American Type Culture Collection, was used for immunofluorescent staining. About 10$^4$ U20S cells were seeded onto 12-mm glass cover slips and used 18 hours later for immunofluorescent staining. The cells were washed once with PBS buffer and fixed with cold acetone for 10 minutes at room temperature. Fixed and permeabilized cells were hydrated in PBS for 1 to 2 minutes. Each cover slip was incubated with 200 μl of rabbit anti-RB IgG (1:20 dilution) or preimmune serum in a moist chamber for 45 minutes at room temperature. After three washes in PBS, the cover slips were incubated with 200 μl or rhodamine-conjugated goat anti-rabbit IgG (25 μg/ml) obtained from Sigma for 45 minutes at room temperature. The cover slips were again washed extensively in PBS and viewed with the Zeiss photomicroscope III.

Alternatively, immunofluorescent staining of LAN-1 neuroblastoma cell lines was carried out as follows. 10$^4$ LAN-1 cells were seeded onto 12-mm glass cover slips and used 18 hours later for immunofluorescent staining. The cells were washed once with PHEM buffer consisting of 0.06M Pipes, 0.025M HEPES, 0.01M EGTA, 0.002M MgCl$_2$, pH 6.9 and fixed with 2% paraformaldehyde in PHEM buffer for 20 minutes at room temperature. Fixed and permeabilized cells were washed once in PHEM buffer and three times in PBS. Each cover slip was incubated with 12 μl of a 1:80 dilution of a rabbit anti-RB IgG, or preimmune serum in a moist chamber for 45 minutes at room temperature. After three washes in PBS, the cover slips were incubated with 12 μl (25 μg/ml) of fluorescein isothiocyanate conjugated goat and anti-rabbit immunoglobulin G obtained from Sigma Chemical Co., for 45 minutes at room temperature. The cover slips were again washed extensively in PBS and incubated at room temperature for 45 minutes with rhodamine-conjugated phalloidin (20 μg/ml) The stained preparation was mounted in PBS-glycerol (1:9) containing the antibleaching agent p-phenylenediamine and viewed with a Zeiss photomicroscope III.

The results are illustrated in FIG. 5B and are similar to those obtained by biochemical fractionation described in the previous example. The fluorescence was present mainly within the nucleus and the preimmune control was negative.

DNA Binding Activity Assay

Two DNA binding assays, DNA-Sepharose column chromatography and filter binding, can be used. These two methods have been previously used in studies of myc (*Nature* (1982) 296:262–266; n-myc (*EMBO J.* (1985) 4:2627–2633; and myb proteins (*Cell* (1985) 40:983–990). Only DNA-Sepharose column chromatography is described below.

Sepharose Column Chromatography

To test DNA binding activity of the RB protein, double-stranded and single-stranded calf thymus DNA coupled onto Sepharose 2B obtained from Pharmacia was employed.

Figures 6A, 6B:
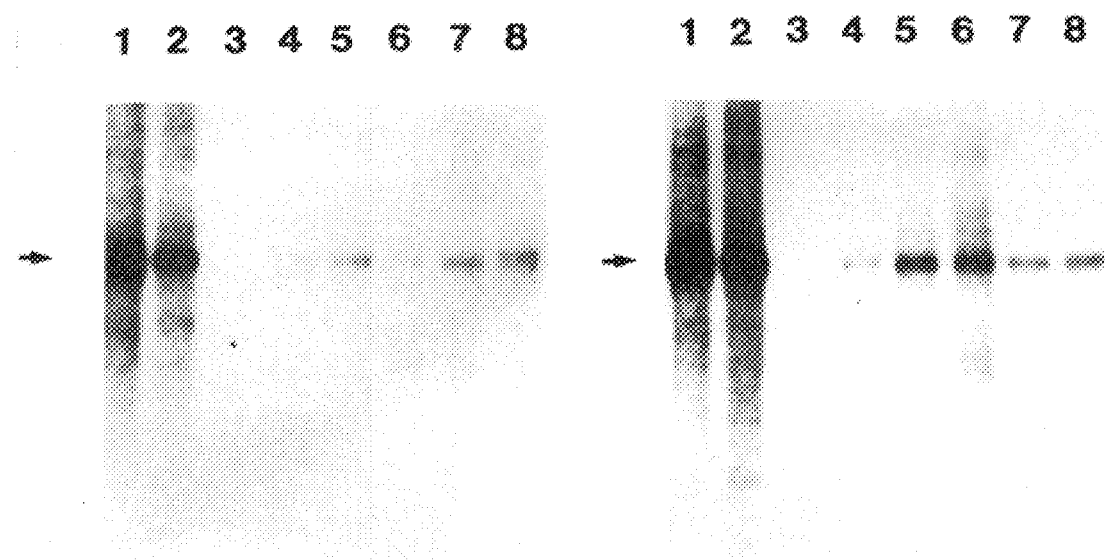

Protein lysates of the human neuroblastoma LAN-1 cells were metabolically labeled with $^{32}$P-phosphoric acid and separated on single-stranded (A) and double-stranded (B) DNA cellulose columns namely with 0.05, 0.1, 0.2, 0.3, 0.5 and 1.0M NaCl. Column chromatography separation of the RB gene protein product on single stranded and double stranded DNA cellulose is illustrated in FIG. 6. LAN-1 cells labeled with $^{32}$P-phosphoric acid for three hours were lysed in lysis buffer and clarified as described previously. The supernatant was diluted 10-fold with loading buffer (1 mM DTT, 0.5% NP40, 10 mM potassium phosphate, 10% glycerol pH 6.2, Aprotinin 200 units/ml). The diluted extract was then applied to calf-thymus DNA-cellulose columns (Pharmacia) *Mol. Cell Biol.* (1986) 6:4450–4457, equilibrated with loading buffer containing 50 mM NaCl. After allowing binding to occur for 40 minutes, the column was washed with 5 ml of loading buffer and then eluted with buffer containing 1 mM DTT, 10 mM Tris-HCl, pH 8.0 with increasing NaCl concentration from 0.05 to 1.0M . The eluates were then immunoprecipitated with rabbit anti-RB IgG. The whole cell lysates and flow-through immunoprecipitated with anti-RB IgG, respectively, served as the controls. Fractions were then analyzed by immunoprecipitation as above. The results are illustrated in FIGS. 6A (single) and 6B (double).

Diagnostic Determination of the RB Protein in the Tissue

Human tumor cells disassociated from biopsy tissue taken from a patient was labeled with $^{35}$S methionine or $^{32}$P-phosphoric acid and immunoprecipitated with anti-ppRB$^{110}$ IgG according to the procedure set forth above. Alternatively, protein lysates extracted from bioptic tissue can be directly diagnosed using the western blotting analysis probed with either radioactive labeled or non-radioactive labeled anti-RB specific antibody. The presence or absence of immunoprecipitated proteins serves as a diagnostic tool in determination of retinoblastoma or other diseases controlled by the retinoblastoma gene.

III. DNA-BINDING ACTIVITY AND SPECIFIC COMPLEX FORMATION WITH SV40 T ANTIGEN

Wild-type or normal RB protein is known to possess two biochemical properties of DNA binding proteins. One is the ability to bind DNA intrinsically (*Nature* (1987) 329:642–645) and the second is the ability to form specific complexes with oncoproteins of several DNA tumor viruses (*Cell* (1988) 54:275–283; *Science* (1989) 243:934–937; *Nature* (1988) 334:124–129). Full-length, recombinantly produced RB protein purified from a baculovirus-infected insect cell system and RB truncated proteins purified from an *E. coli* expression system were tested for these two known biochemical properties.

Production of the RB Proteins and Assay Reagents

TRP E-RB fusion proteins described above also were used in this assay.

A baculovirus expression system was utilized for the recombinant production of a full-length RB protein. The protein was designated p110$^{RB}$. The expression vector was constructed as described in *Cell Growth and Diff.* (1990) 1:429–437.

Recombinant Baculovirus Construction

The baculovirus *Autograph californica* nuclear polyhedrosis virus (AcNPV) is known to be suitable as a helper-independent viral expression vector for the high-level production of recombinant proteins in cultured insect cells. This virus propagates in cultured Fall Army worm *Spodoptera frugiperda* (Sf9) cells and has a strong temporally regulated promoter of the polyhedrin gene, whose product represents 50% or more of total cellular proteins during a lytic infection. By in vivo recombination, the coding sequence of a foreign gene can be placed under the transcriptional control of the polyhedrin promoter, resulting in a high level of protein expression. In addition, such proteins may be correctly folded and contain appropriate post-translational modifications like those proteins in the original higher eucaryotes.

To test the feasibility of expressing functional RB protein by the baculovirus system, cloned human RB cDNA, containing the complete coding sequence of the RB gene, was introduced into the AcNPV expression vector and the recombinant viruses were propagated in insect cells. Successful expression of human p110$^{RB}$, at high level, by the host-vector system was achieved. The protein produced is phosphorylated and correctly targeted to the nuclei of infected cells. In addition, methods for the purification of RB protein were developed. It was found that the purified protein can bind DNA and form a specific complex with SV40 T antigen in the same way as the authentic human pp110$^{RB}$. The prompt nuclear translocation of the protein after microinjection further suggests the active nature of the purified RB protein.

In order to achieve maximal production of the RB protein in the baculovirus expression system, recombinant transfer vectors were constructed with deletion of most of the 5' non-coding sequence of the RB gene. By site-specific mutagenesis, two BamHI sites were introduced into the RB cDNA at nucleotides 116 and 2935 to facilitate construction of the recombinant transfer vector. The resulting vector, encodes an mRNA that contains the entire (60 base pairs) polyhedrin 5' non-coding sequence fused to 23 base pairs of the 5' untranslated region of the RB cDNA, followed by the complete coding sequence. This recombinant gene contains no ATG codons upstream of the authentic RB initiation site at nucleotide 139. Thus, the recombinant gene encodes a non-fusion, full-length RB protein.

Referring to FIG. 31, there is depicted the transfer vector pAcYM1, which has all the upstream sequences of the polyhedrin gene, including the A of the initiating codon, followed by a unique BamH1 site. The transfer vector was designated pAcYM1, which has all the upstream sequences of the polyhedrin gene, including the A of the initiating ATG codon, followed by a unique BamHI site. The transfer vector has been described by Matsura et al. *J. Gen. Virol.* (1987) 68:1233–1250. pRB44-2 contains the complete RB cDNA coding sequence from nucleotides 116 to 2935 subcloned into the BamHI site of plasmic pGEM1 (Promega). The recombinant baculovirus vector, pAcYM1/RB2.8, was constructed by inserting the 2.8 kb BamHI fragment from pRB44-2 into the BamHI site of pAcYM1 in a proper orientation so that the transcription of the RB gene would be under the direct control of the polyhedrin promoter.

In the construction of the baculovirus expression vector for RB synthesis, the following matters were considered. p$^{RB}$44-2 consists of the complete RB cDNA coding sequence from nucleotide 116 to 2935 subcloned into the BamHI site of pGEM1. pAcYM1 contains the approximately 7 kb EcoRI fragment of the viral DNA sequence flanking the polyhedrin gene in which the leader sequence remains intact, but all of the polyhedrin coding sequences except the first A of the ATG are replaced by a BamHI linker.

The recombinant baculovirus vector, pAcYM1/RB2.8, containing polyhedrin promoter-RB cDNA fusion, was constructed by inserting the RB2.8 BamHI fragment into the BamHI site of pAcYM1 so that the transcription of the RB gene would be under the direct control of the polyhedrin promoter. The sequence at the junction of the fusion is shown at the bottom of FIG. 31 with the lower case symbol representing the polyhedrin promoter, and the upper case representing the RB cDNA sequence, while the BamH1 linker is underlined. The translation of the fusion gene utilizing the ATG of the RB (nucleotide 139) is indicated by the arrow, whereas a* (+1) of FIG. 31 represents the first A of the translation start codon ATG of the polyhedrin gene.

Transfer of RB cDNA from the recombinant plasmid to the viral genome was achieved by cotransforming pAcYM1/RB2.8 DNA with wild-type *Autographa californica* nuclear polyhedrosis virus DNA by lipofection (BRL). The recombinant viruses, in which the polyhedrin gene had been inactivated by allelic replacement with the RB gene through homologous recombination, were identified by their distinct plaque morphology as they showed no polyhedrin occlusion bodies in infected cells. The viruses were subjected to three rounds of plaque purification to obtain a pure stock of RB-containing baculovirus, which was designated as AcNPV-Y4 RB.

Expression of Exogenous RB Protein in Infected Insect Cells

Prior to determining whether the AcNPV polyhedrin promoter could drive the expression of human RB gene in heterologous invertebrate cells, Sf9 cells were prepared. Sf9, a clonal isolate of *Spodoptera frugiperda* IPLB-Sf21-AE In vitro, 13:213–217 (1977) was grown as a monolayer or suspension cultures at 27° C. in Grace's insect medium supplemented with 3.33 gm/l of yeastolate, lactalbumin hydrolysate (GIBCO), and 10% heat-inactivated fetal bovine serum (GIMINI) *Bull.* 1555 (1987), (Texas Agricultural Experiment Station, College Station, Tex.). In large-scale preparation of cellular lysates, spinner cultures of Sf9 cells were grown in EX-CELL 400 serum-free defined medium (J.R. Scientific). Molt-4 cells, a human T cell leukemia line, were cultured in suspension in RPMI 1640 supplemented with 20% calf serum. Saos-2 cells, an osteosarcoma cell line, were grown in Dulbecco's modified Eagle's medium supplemented with 7.5% fetal bovine serum.

In determining whether the AcNPV polyhedrin promoter could drive the expression of human RB gene in heterologous invertebrate cells, Sf9 cells were infected with plaque-purified AcNPV-Y4 RB. Forty hours after infection, lysates of the infected cells were collected and immunoprecipitated with anti-RBO.47 antibody. Samples were then subjected to SDS-PAGE, followed by Western blot analysis.

As shown in FIG. 32A, immunoblotting with pMG3-245 monoclonal antibody revealed the appearance of full-length RB protein similar to that of the mammalian cells (lane 1) in extracts of cells infected with AcNPV-Y4 (lane 3), but not in the mock or wild-type AcNPV infected cells (lanes 2 and 4). With regard to FIG. 32B, cellular extracts from AcNPV-Y4 RB infected cells were prepared at different times post-infection, in order to determine the optimal timing for RB protein production. The lysates were immunoprecipitated with anti-RB0.47 antibody and immunoblotted with pMG3-245 monoclonal antibody. In FIG. 32B, p110$^{RB}$ represent unphosphorylated and phosphorylated RB proteins, respectively. The production of the RB protein was monitored during the post-infection period to determine the optimal timing for harvesting the cells. As shown in FIG. 32B, RB protein production can be detected at 24 hours after infection and it is significantly increase during the following 12 hours. The level of protein production was maintained through about 72 hours of infection, at which time significant viral lysis of the cells began. To minimize protein degradation associated with cell lysis, infected cells were routinely harvested around 40 hours post-infection.

In detecting the expression of the RB protein, AcNPV-Y4 RB was used to infect Sf9 cells at a MOI of 0.5. At 24, 36, 48, 60 and 72 hours post-infection, $5\times10^4$ cells were lysed in 1 ml lysis buffer (50 mM Tris-HCl, pH 7.4; 0.2% Nonidet P-40; 1 mM EDTA; 100 mM NaCl; 50 mM NaF and 1 mM PMSF), and the lysates were clarified by centrifugation (4° C., 20,000×g) for 5 minutes. Lysates were then incubated with anti-RBO.47 antibody, and immunoprecipitates were separated by 7.5% SDS-PAGE. Proteins were then transferred to nitrocellulose paper, following conventional techniques. After overnight blocking, the nitrocellulose paper was incubated with pMG3-245 anti-fRB monoclonal antibody for 3 hours, followed by alkaline phosphatase-conjugated goat anti-mouse IgG and colorigenic substrates, as described in *Cell* (1988) 54:275–283.

Nuclear Localization and Post-translational Phosphorylation of Exogenous RB Protein The RB gene encodes a nuclear phosphoprotein of about Mr 110,000. To determine whether RB protein produced in insect cells with the baculovirus was targeted to the nucleus, AcNPV-Y4 RB-infected Sf9 cells were immunostained with anti-RBP.47 antibody 40 hours after infection. Such a condition is characteristic of the cytopathic effect of baculovirus infection.

In performing the immunostaining analysis, the following steps were performed. After 40 hours of either mock, wild-type AcNPV, or AcNPV-Y4 infection, Sf9 cells were seeded on poly-L-lysine (Sigma) coated chamber slides (Miles Scientific) and incubated overnight. Slides were washed with phosphate-buffered saline between each of the following steps: cells were first fixed with 4% formaldehyde in 0.04M phosphate buffer (pH 7.4) for 20 minutes or with acetone (−20° C.) for 10 minutes, and immersed in 1% $H_2O_2$ in methanol for 10 minutes. Fixed cells were preincubated with 2% normal goat serum in PBS for 10 minutes and then incubated overnight with rabbit anti-RBO.47 antibody diluted in 0.02% Triton X-100. After washing, biotinylated goat anti-rabbit IgG (TAGO, Burlingame, Calif.) was added. One hour later, cells were incubated with AB complex conjugated with horseradish peroxidase (Vector Labs, Burlingame, Calif.) for 45 minutes and then incubated with substrate. The substrate comprised 0.05% with 3,3'-diaminobenzidine tetrahydrochloride and 0.01% $H_2O_2$ in 0.05M Tris-HCl, pH 7.6 (Sigma). Reactions were stopped 3 to 5 minutes later by washing cells with PBS. Subsequently, the cells were photographed with a Nikon diaphotomicroscope.

Phosphorylation of RB protein occurs at multiple serine and threonine residues and accounts for the molecular weight heterogeneity of RB protein in the SDS-PAGE see FIG. 33 and *Oncogene Res.* (1989) 1:205–214 and *Cell* (1989) 56:57–65. To determine whether RB protein produced in the insect cells undergoes phosphorylation post-translationally, AcNPV-Y4 RB-infected Sf9 cells were metabolically labeled with $^{35}$S-methionine or $^{32}$P-orthophosphate for 3 hours at 40 hours after infection. Cell extracts were subjected to immunoprecipitation and analyzed by SDS-PAGE followed by autoradiography. In parallel, immunoprecipitable RB protein from the same extracts was treated with potato acid phosphatase (PAP) to test the effect of dephosphorylation on RB protein mobility in SDS-PAGE. After dephosphorylation, the $^{35}$S-labeled RB protein was reduced from a doublet to a single band of Mr 110,000 and radioactivity was almost completely released from $^{32}$P-labeled RB protein. Dephosphorylation analysis by Western blotting of lysates from unlabeled cells infected with AcNPV-Y4 RB also showed the same band reduction pattern after PAP treatment. These observations indicated that RB protein produced in insect cells was phosphorylated, and the modification also accounted for the molecular weight heterogeneity of this RB protein observed in the SDS-PAGE.

In performing the radiolabeling of Sf9 insect cells and dephosphorylation analysis, the following steps were performed. At 40 hours post-infection, Sf9 cells ($3 \times 10^6$) in 60 mm dishes were incubated with DME medium lacking either methionine or phosphate and supplemented with 10% fetal calf serum for 30 minutes. The cells were then metabolically radiolabeled by supplementing with 0.25 mCi/ml $^{35}$S-methionine (1134 Ci/mmole, NEN) or with 0.25 mCi/ml $^{32}$P-orthophosphate (carrier-free, ICN) for 3 hours. Cell extracts were then prepared in lysis buffer (50 mM Tris-HCl, pH 7.4; 0.2% Nonidet P-40; 1 mM EDTA; 100 mM NaCl; 50 mM NaF and 1 mM PMSF), and immunoprecipitation with anti-RBO.47 antibody was performed.

Two-thirds of the immunoprecipitated RB protein, from 35S- or $^{32}$P-labeled as well as unlabeled cell lysates, were subjected to potato acid phosphatase (PAP, Boehringer) dephosphorylation analysis *Oncogene Res.* (1989) 1:205–214. Immune complexes containing the RB protein were incubated with 1.5 units of PAP in reaction buffer (20 mM MES, pH 5.5; 100 mM NaCl; 1 mM $MgCl_2$; 50 $\mu$M leupeptin) for 60 minutes at 37° C. After the reaction, RB protein was analyzed by 7.5% SDS-PAGE, followed by either autoradiography or Western blotting.

The following procedures were followed for purifying the protein from infected insect cells. Sf9 cells were infected with AcNPV-Y4 RB at a MOI of 1.0, and cultured in suspension ($1 \times 16^6$ cells/ml, 1000 ml). Forty (40) hours after infection, cellular lysates were prepared by pelletting by low-speed centrifugation. Under this condition the total level of RB protein expressed in the baculovirus system was approximately 17–18 mg per liter of infected insect cell culture (approximately $10^9$ cells). In this regard, see the table below.

Purification of recombinant RB protein from baculovirus infected insect cells

| Step | Total protein (mg) | RB protein (mg) | Yield (%) | Purification fold | Purity (%) |
|---|---|---|---|---|---|
| Cellular Extract | 670[a] | 16[b] | 90[c] | 1.0 | 2.3 |
| pMG3-245 Immuno-affinity Column | 13.5[b] | 12.8[d] | 72[c,d] | 41.3 | 95 |

[a]Protein quantitation by the method of Bradford (Bio-RAD).
[b]Protein quantitation by Micro BCA (PIERCE) and spectrophotometry.
[c]Protein quantitation by Western blot and densitometry
[d]Protein quantitation by Coomassie brilliant blue staining and densitometry.

As shown above, 90% (16 mg) of the RB protein expressed were found in the supernatant after cell disruption, while 10% remained in the insoluble fraction. The RB protein could readily be detected in the cellular lysate as it represented 2.3% of the total cellular protein. Following the one-step immunoaffinity chromatographic purification, approximately 13.5 mg of proteins could be recovered from the alkaline eluates of the column. To estimate the purity of the eluted RB protein, an aliquot of the eluates corresponding to $2.5 \times 10^5$ cells were analyzed by SDS-PAGE and Coomassie brilliant blue staining.

Providing more detail for the purification procedure, the cellular lysate washed, and resuspended in an extraction buffer containing 50 mM Tris-HCl, pH 7.4; 0.2% NP-40; 1 mM EDTA; 100 mM NaCl; 10% (v/v) glycerol; 1 mM DTT; 1 mM PMSF; 25 $\mu$g/ml leupeptin and 50 units/ml aprotinin. After a 15-minute incubation on ice, the sample was clarified by centrifugation (10,000×g, 4° C. for 10 minutes), and the RB-containing supernatant was collected. Immunoaffinity chromatography of the RB protein was carried out on a two milliliter volume column containing an anti-fRB monoclonal antibody (pMG3–245) linked to protein G-Agarose.

After passing the supernatant through the column four times, the column was washed sequentially with 200 bed-volumes of each of the following: lysis buffer, lysis buffer containing 500 mM NaCl, and washing solution (200 mM NaCl; 1 mM EDTA; 1 mM DTT; 1 mM PMSF; 10% glycerol). Bound proteins were then eluted from the column by alkaline elution buffer containing 20 mM triethylamine, pH 10.8; 200 mM NaCl; 1 mM EDTA; 1 mM DTT; 1 mM PMSF and 10% glycerol. One-ml fractions were collected, immediately neutralized with one-twentieth volume of 1M Tris-HCl (pH 7.5) and stored at –70° C. in 10% glycerol.

In purifying the RB protein from the infected insect cells, the amount of total protein was determined and subsequently, Southwestern DNA-binding assays and SV40 T-antigen binding assays were performed as described below.

The amount of total protein in the elution fraction of the immunoaffinity column was determined by Micro-BCA assay (PIERCE). The total eluted protein sample was then analyzed by SDS-PAGE, and the amount of RB protein in the eluate was estimated by Coomassie brilliant blue staining followed by densitometry.

The amount of total protein in the cellular extract was measured by the method of Bradford (Bio-Rad) *Anal. Biochem.* (1976) 72:248–254. To quantitate RB protein in cellular lysates, western blotting was performed using serially diluted purified RB protein as standard followed by densitometric comparison of the band intensity.

Conventional techniques were used for protein blotting such as incubation of blots with radiolabeled DNA following the protocols described in *Nucleic Acids Res.* (1980) 8:1–21. This procedure was carried out at room temperature. Blots were rinsed briefly with water and then washed three times with 6M urea; 0.2% NP-40 (20 min. each), followed by four washes (30 min. each) with DNA-binding buffer (10 mM Tris-HCl, pH 7.0; 1 mM EDTA; 50 mM NaCl; 0.2% BSA; 0.2% Ficoll 400 and 0.2% polyvinyl pyrolidone). The blots were then incubated for 30 minutes in DNA-binding buffer containing $^{32}$P-labeled DNA. pGEM1 DNA linearlized by EcoR1 was labeled with $\alpha^{32}$P deoxynucleotides (Amersham, >3000 Ci/mmol) by random priming and was used as the probe. After hybridization, blots were washed three times (10 min. each) with DNA-binding buffer, air-dried, and analyzed by autoradiography. TRP E-RB fusion proteins were included as controls. Each TRP E-RB fusion protein was named according to the exons of the RB gene that the protein contains. Thus, RB19-22, RB23-27, and RB19-27 spanned the regions of the recombinant protein from exon 19 to 22 (amino acids 612–775), exon 23 to 27 (amino acid 776–928) and exon 19 to 27 (amino acid 612–928), respectively.

SV40 T-antigen was purified by immunoaffinity chromatography from Ad-SV X1-infected 293 cells, see *J. Virol.* (1985) 53:1001–1004 and "Eucaryotic Viral Vectors" *Cold Spring Harbor Press.* (1982) Cold Spring Harbor, N.Y. pp. 187–192, and an anti-T monoclonal antibody (PAB419 antibody) was obtained from Oncogene Inc. A known complex formation assay was performed as described in *Cell* (1988) 54:275–283, with minor modification. Briefly, 800 ng of baculovirus-expressed RB protein were mixed with 1 ml of EBC buffer (50 mM Tris-HCL, pH 8.0; 120 mM NaCl; 0.5% Non-idet P-40) containing 1 mM PMSF 25 µg/ml leupeptid 50 units/aprotinin. Eight hundred (800) ng of purified T antigen was added to the mix; it was incubated on ice for 90 minutes. Aliquots of the mixture were immunoprecipitated with either anti-RBO.47 or PAB419 monoclonal antibody and subjected to western blotting analysis. Blots were sequentially reacted with pMG3-245 followed by PAB419. After incubating with alkaline phosphatase-conjugated goat anti-mouse IgG, the blots were developed with colorigenic substrates.

DNA and Protein Binding Assays

Figure 10A:
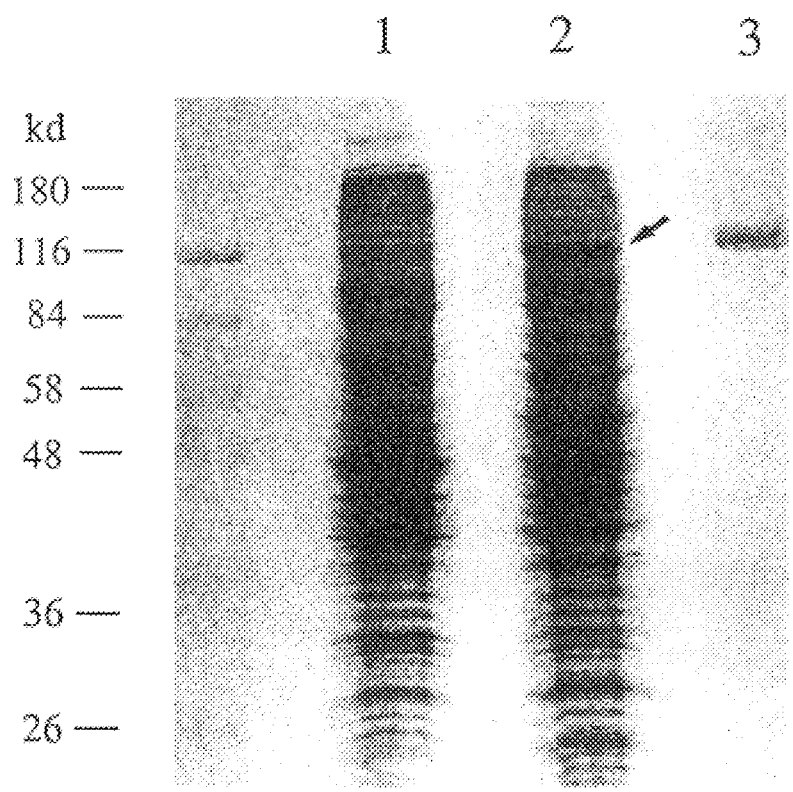
Figure 10B:
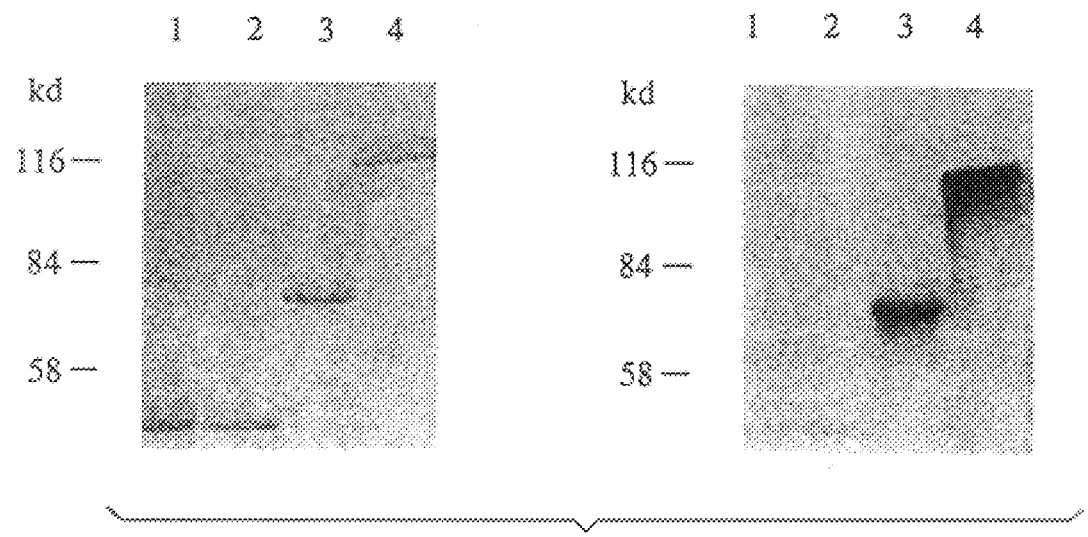

FIGS. 10A and 10B depict Southwestern DNA-binding assays. Six (6) µg of purified TRP E-RB fusion proteins (truncated RB protein) and full length recombinant RB protein produced from the baculovirus system described above, were applied to 10% SDS-PAGE. In the assay depicted in FIG. 10A, Coomassie brilliant blue staining was utilized while in the assay of FIG. 10B, a parallel gel was electrotransferred onto nitrocellulose paper; it was then incubated with $^{32}$P-labeled DNA fragments and analyzed by autoradiography.

In FIG. 10B, DNA bound to the protein was then analyzed by autoradiography. It has been determined that fusion protein, RB19-27, which contains the major domain for interacting with DNA, has a 20-fold higher affinity for DNA than either of two subregions, RB19-22 and RB23-27. In this regard, lane 3 of FIG. 10B can be compared with lanes 1 and 2, while the purified full-length RB protein exhibited a strong DNA-binding activity similar to that of RB 19-27 (FIG. 10, lane 4). DNA-binding activity of the recombinant RB protein isolated from the baculovirus system also was demonstrated by retention of the protein by DNA-cellulose and its subsequent elution from the column, at approximately 400 mM NaCl.

As noted previously, Sf9 cells were infected with AcNPV-Y4 at a MOI of 1.0, and cultured in suspension (1×16$^6$ cells/ml, 1000 ml). After 40 hours of infection, the cells were pelleted by low-speed centrifugation, washed, and resuspended in an extraction buffer containing 50 mM Tris-HCl, pH 7.4; 0.2% NP-40; 1 mM EDTA; 100 mM NaCl; 10% (v/v) glycerol; 1 mM DTT; 1 mM PMSF; 25 µg/ml leupeptin and 50 units/ml aprotinin. After a 15-minute incubation on ice, the sample was clarified by centrifugation (10,000×g, 4° C. for 10 minutes), and the RB-containing supernatant was collected. Immunoaffinity chromatography of the RB protein was carried out on a two milliliter volume column containing an anti-fRB monoclonal antibody (pMG3-245) linked to protein G-Agarose as described herein.

After passing the supernatant through the column four times, the column was washed sequentially with 200 bed-volumes of each of the following: lysis buffer, lysis buffer containing 500 mM NaCl, and washing solution (200 mM NaCl; 1 mM EDTA; 1 mM DTT; 1 mM PMSF; 10% glycerol). Bound proteins were then eluted from the column by alkaline elution buffer containing 20 mM triethylamine, pH 10.8; 200 mM NaCl; 1 mM EDTA; 1 mM DTT; 1 mM PMSF and 10% glycerol. One-ml fractions were collected, immediately neutralized with one-twentieth volume of 1M Tris-HCl (pH 7.5) and stored at −70° C. in 10% glycerol.

In purifying the pp110$^{RB}$ from the infected insect cells, the amount of total protein was determined and, subsequently Southwestern DNA-binding assays and SV40 T antigen binding assays were performed. The amount of total protein in the elution fraction of the immunoaffinity column was determined by Micro-BCA Assay (PIERCE). The eluted protein sample was then analyzed by SDS-PAGE, and the amount of RB protein in the eluates was estimated by Coomassie brillian blue staining followed by densitometry. The amount of total protein in the cellular extract was measured by the method of Bradford (Bio-Rad) *Anal. Biochem.* (1976) 72:248–254. To quantitate RB protein in cellular lystates, Western blotting was performed using serially diluted purified RB protein as standard followed by densitometric comparison of the band intensity. In this regard, see the Table above.

Protein blotting was performed, utilizing conventional techniques. Incubation of blots with radiolabeled DNA followed the protocols described by *Nucleic Acids Res.* (1980) 1–21. The procedure was carried out at room temperature. Blots were rinsed briefly with water and then washed three times with 6M urea; 0.2% NP-40 (20 minutes each), followed by four washes (30 minutes each) with DNA-binding buffer (10 mM Tris-HCl, pH 7.0; 1 mM EDTA; 50 mM NaCl; 0.2% BSA; 0.2% Ficoll 400 and 0.2% polyvinyl pyrolidone). The blots were then incubated for 30 minutes in DNA-binding buffer containing $^{32}$P-labeled DNA. pGEM1 DNA linearized by EcoR1 was labeled with α-$^{32}$P deoxynucleotides (Amersham, greater than 3000 Ci/mmol) by random priming and was used as the probe. After hybridization, blots were washed three times (10 minutes each) with DNA-binding buffer, air dried, and analyzed by autoradiography. TRPE-RB fusion proteins were included as controls. Each TRPE-RB fusion protein was named according to the exons that the protein contains. Thus, RB19-22, RB23-27, and RB19-27 spanned the regions of pp110$^{RB}$ from exon 19 to 22 (amino acids 612–775), exon 23 to 27 (amino acid 776–928) and exon 19 to 27 (amino acid 612–928), respectively.

SV40 T antigen was purified by immunoaffinity chromatography from Ad-SV X1-infected 293 cells *J. Vir.* (1985) 53:1001–1004; *Cold Spring Harbor Press.* Cold Spring Harbor, N.Y. pp. 187–192 (1982) and anti-T monoclonal PAB419 antibody was obtained from Oncogene Inc. A known complex formation assay was performed, with minor modification, in which 800 ng of baculovirus expressed RB protein was mixed with 1 ml of EBC buffer (50 mM Tris-HCl, pH 8.0, 120 mM NaCl and 0.5% Nonidet P-40) containing 1 mM PMSF, 25 µg/ml leupeptid and 50 units/ml aprotinin. 800 ng of purified T was added to the mix and mixture was incubated on ice for 90 minutes. Aliquots of the mixture were immunoprecipitate with either anti-RBO.47 or PAB 419 antibody and subjected to western blotting analysis. Blots were sequentially reacted with pMG3–245 followed by PAB419. After incubating with alkaline phosphatase-conjugated goat anti-mouse IgG, the blots were developed with colorigenic substrates.

To test the ability of the purified RB protein to form a specific complex with SV40 T-antigen, equal amounts of the full length RB protein and SV T-antigen were mixed, and aliquots of the mixture were immunoprecipitated with either anti-RBO.47 antibody or anti-T antibody PAB419.

Figure 11:
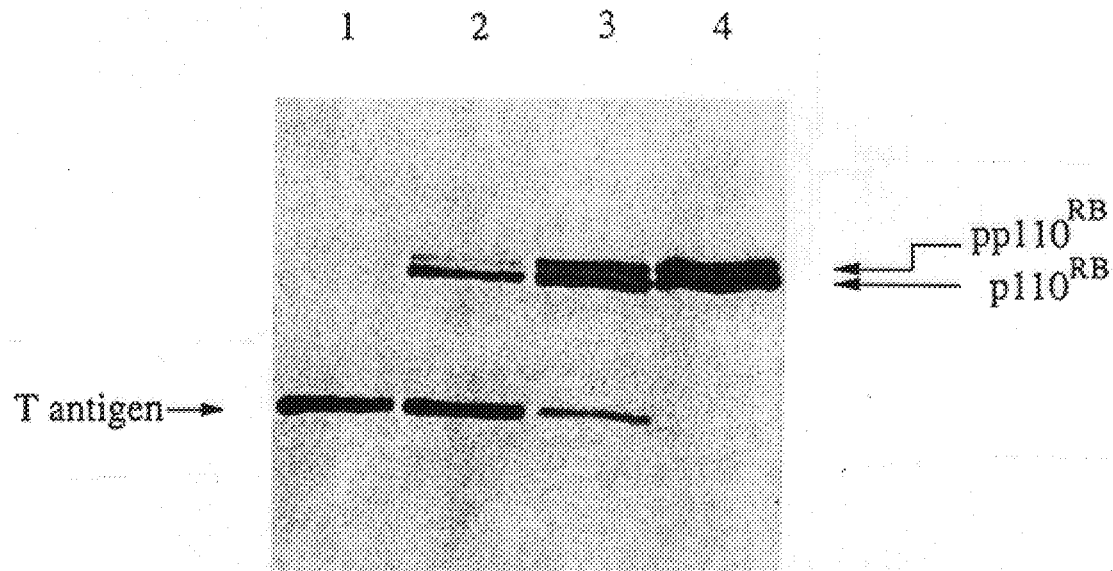

FIG. 11 depicts complex formation of baculovirus-expressed RB protein (p110$^{RB}$) with SV40 T-antigen. The purified full length RB protein was mixed with purified T-antigen in a test tube, i.e., in vitro. Identical aliquots of the mixtures were then immunoprecipitated with PAB419 (lane 2) or anti-RBO.47 (lane 3) and analyzed by western blotting. Lanes 1 and 4 show purified SV40 T-antigen immunoprecipitated with PAB419, and purified baculovirus-expressed RB protein immunoprecipitated with anti-RBO.47 antibody, respectively.

Mixing of RB protein with SV40 T antigen in vitro resulted in the co-immunoprecipitation of the RB protein with PAB419 (lane 2), as well as the co-immunoprecipitation of T with anti-RBO.47 antibody (lane 3). These data demonstrated that purified, full length RB protein isolated from a baculovirus expression system is capable of forming a specific complex with SV40 T antigen.

Nuclear Translocation of Purified RB Protein

After determining that the purified RB protein retained the two known biochemical activities of wild-type RB in vitro, the behavior of the purified protein was investigated in vivo.

Purified RB protein, p110$^{RB}$, was injected into the cytoplasm of Saos-2 cells, an osteosarcoma cell line which contains a defective RB gene with deletion of exons 21–27 and encodes a C-terminal truncated RB protein (p95), *Proc. Natl. Acad. Sci. USA* (1990) 87:6–10. The p95 protein is located in the cytoplasm in such minute amounts that it is not recognized by the anti-RBO.47 antibody used herein, even though the antibody is directed against the C-terminus of RB protein. Immediately after injection, cells were fixed and subjected to immunostaining analysis.

For microinjection, purified RB protein was dialyzed into injection buffer containing 20 mM Tris-HCl, pH 7.4; 10 mM KCl; 0.1 mM EDTA; 0.1 mM DTT and 2% glycerol to a final concentration of 0.5 mg/ml. Saos-2 cells, growing on glass chamber slides were microinjected according to conventional techniques, using glass capillary needles (Eppendorf). An Eppendorf micromanipulator, equipped with a vacuum and pressure device, and an inverted phase-contrast microscope (Nikon) were employed for micromanipulation of the capillary and visualization of the microinjection process. After microinjection, the cells were immediately fixed by 4% formaldehyde in 0.04M phosphate buffer (pH 7.4) and subjected to immunostaining analysis.

Figure 12:
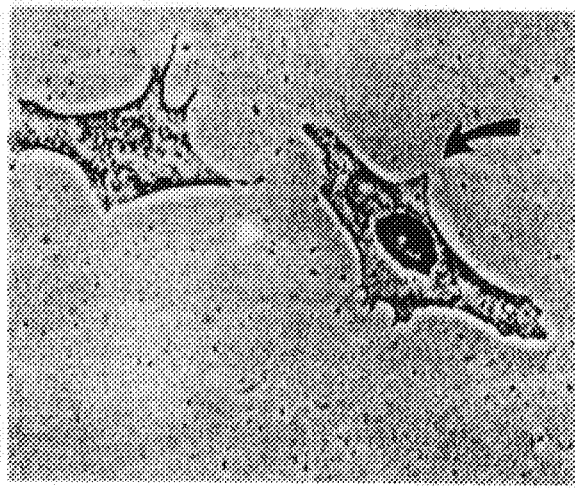
Figure 13:
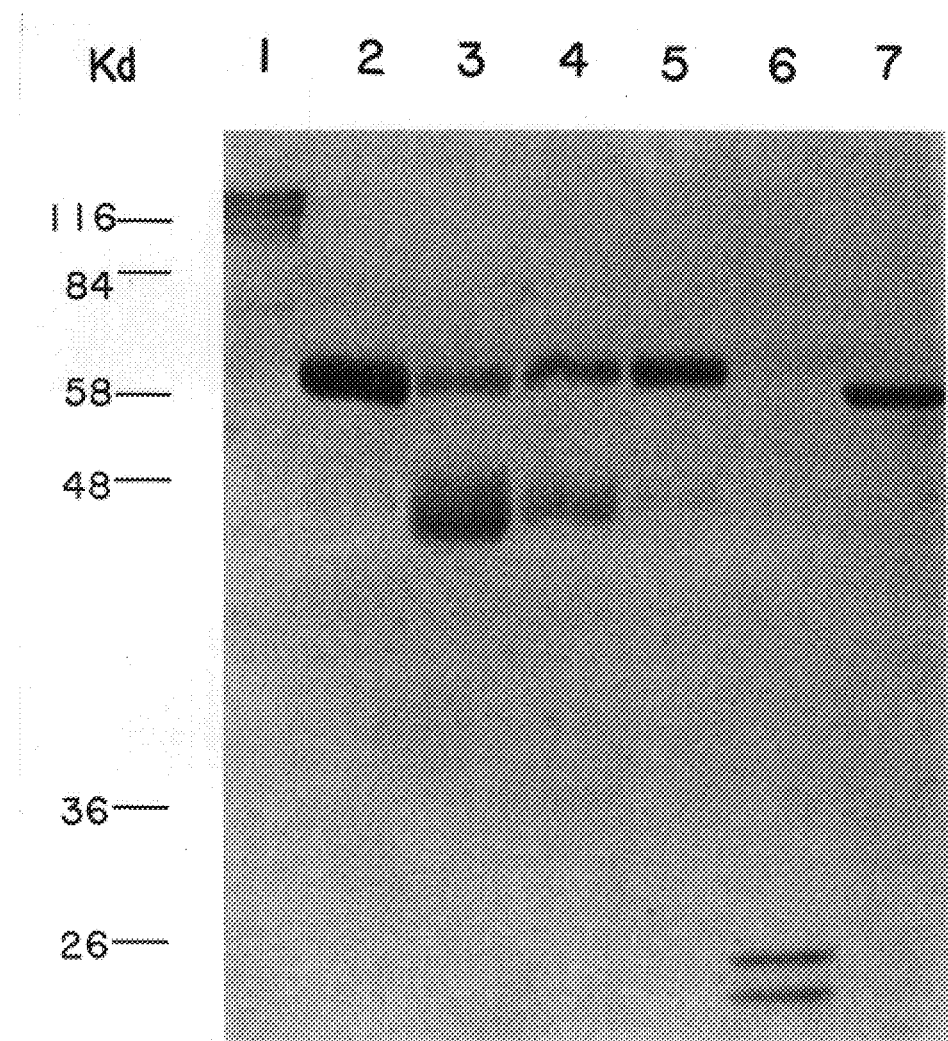
FIG. 13 depicts SDS-PAGE analysis of the concentration and purity of protein preparations used for microinjection.

FIG. 12 shows nuclear translocation of the recombinant RB protein p110$^{RB}$ after microinjection into the cytoplasm of Saos-2 cells. The cells were injected with purified RB protein and subjected to immunostaining analysis. The arrow in FIG. 12 indicates the intense staining of the nucleus after microinjection, as compared to that of uninfected cells. The intense staining of the nucleus of the injected cell as compared to that of the uninfected control, indicates the rapid transport of the injected protein into the nuclei. Since RB protein has been known as a nuclear protein, the prompt and accurate nuclear translocation of purified protein across the nuclear membrane after microinjection, further suggests that the recombinant RB protein is active in vivo.

The above results demonstrate that a human retinoblastoma gene product can be expressed efficiently in a baculovirus expression system. The attempt to express RB protein at high levels has long been regarded as difficult since it was suspected that RB protein might hinder or even be "toxic" to the growth of cells. The transcription of foreign genes from the polyhedrin promoter occurs late in infection, following production of extracellular viral particles and the shut-off of cellular and most viral genes. The baculovirus-insect cell system is therefore advantageous for the synthesis of proteins, such as the RB protein which may be detrimental to cell growth when overproduced. Another advantage of this system is the similarity in protein processing pathways of insect and mammalian cells.

RB protein produced in a baculovirus expression system has been shown to be accurately targeted to the nuclei of insect cells implying that mammalian nuclear translocation signals are also recognized by insect cells. Although glycosylation of recombinant proteins in the baculovirus expression system seems limited to the O-linked and N-linked oligosaccharides of the high mannose-type, appropriate phosphorylation of foreign proteins has been reported for the expression of c-myc and HTLV-I p40$^x$. RB protein has previously been shown to be phosphorylated but not glycosylated, making the baculovirus expression system suitable for the production of functional protein.

The RB p110$^{RB}$ protein produced in infected insect cells is post-translationally phosphorylated, and multiple bands can be differentiated by western blotting analysis, just as in the case of authentic mammalian RB protein. However, as judged by band intensity, un- and hypophosphorylated forms are predominant when compared to the hyperphosphorylated RB protein. It is not known whether this phenomenon is a reflection of the cell cycle status of the population during a viral lytic infection, or is simply due to the insufficient phosphorylation of the protein by insect kinases because of the massive amount of exogenous RB present in the cells. Precise mapping of phosphorylation sites in the RB protein will determine whether the phosphorylation patterns are truly identical to that of mammalian protein.

The total level of recombinant RB protein expressed in the baculovirus system is about 17–18 mg per liter of infected insect cell culture (~10$^9$ cells). This level of expression is comparable to other mammalian proteins produced by this system, such as 10–20 mg/l for interleukin 2 *The Banbury Report*. Fields, B., et al. (ed.) (1985) 22:319–328 Cold Spring Harbor Laboratory Press, Cold Spring Harbor, and 4–5 mg/l for P210 BCR-ABL, *Oncogene* (1989) 4:759–766. The high level of expression of RB protein may be enhanced by using a recombinant transfer vector containing the intact polyhedrin 5' untranslated region, fused with the RB cDNA deprived of most of its 5' non-coding region. This sequence of the RB mRNA is highly G+C rich, a factor which may favor the formation of stable secondary structures. These structures, when present in front of an initiation codon, are thought to decrease the translational efficiency of the corresponding mRNA. Five- to ten-fold enhancement of the in vitro translation of RB mRNA has been demonstrated by the replacement of RB 5' untranslated sequence with that of the alfalfa mosaic virus (AMV) RNA4, or β-globin mRNA, further suggesting the potential adverse effect, on the translation, *EMBO J.* (1990) 9:1815–1822 of RB 5' non-coding sequence. The presence of long 5' untranslated sequences of the foreign genes has also been shown to affect the recombinant protein expression in the baculovirus system. Since the polyhedrin promoter is very A+T-rich, it has been concluded that the long and G+C-rich 5' non-coding sequence be trimmed from the RB cDNA, prior to the insertion into the transfer vector, for optimal expression of the RB DNA sequence.

Several different protocols for the elution of RB protein from affinity columns have been tested in an attempt to minimize the denaturation of protein during the purification process. Since not much is known of the biological and biochemical properties of RB protein, the only two parameters that can be used as measures of the integrity of purified protein are the activities of DNA-binding and complex formation with SV40 T antigen. It was found that the present elution condition, using 20 mM triethylamine at pH 10.8 was effective in preserving the biochemical properties of the protein. Rapid nuclear translocation of the purified protein from the cytoplasm after microinjection further demonstrated that the protein was active under this elution condition. Elution of the protein at extreme pH (200 mM glycine, pH 2.3 or 100 mM triethylamine, pH 11.5) tended to denature the protein in that the aforementioned two activities were greatly diminished. This also was evident by the formation of insoluble aggregates, after long term storage.

While it has been previously reported that only the unphosphorylated RB protein can bind SV40 T antigen in D2C2 cells, a stable transformed of monkey kidney cell line CV1-P by SV40 T antigen (*Cell* (1989) 56:57–65), it was found that certain hypophosphorylated forms of the RB protein were able to form complexes with the SV40 T antigen. This was reproducibly demonstrated with the in vitro mixing of T antigen with purified RB protein from AcNPV-Y4 RB infected-insect cells, or with Molt-4 lysates. The same phenomenon has been observed when Cos cells for in vivo complex formation were used. Since phosphorylation of the RB protein oscillated during the cell cycle in a phase-specific manner and the complex formation between RB and viral oncoproteins has been implicated in the transforming activity between hypophosphorylated RB protein and SV40 T antigen awaits future elucidation.

The availability of significant amounts of soluble, intact and presumably active RB protein, utilizing the baculovirus-insect cell system represents a major advance for future studies of the biochemical and biophysical properties of the RB gene product. Possible applications include analysis of associated cellular proteins, isolation of the specific DNA sequence with which they interact, and three-dimensional structural studies of the RB protein utilizing X-ray crystallography. The elucidation of the biological function of the retinoblastoma gene in cancer suppression can also be facilitated. The possible involvement of RB in cell growth and differentiation, directly tested by microinjection, are now under investigation.

IV. RECOMBINANTLY PRODUCED RB PROTEIN STOPS GROWTH OF CELLS

Preparation of Cells

An osteosarcoma cell line, Saos-2, was used for these studies. It was obtained from the American Type Culture Collection. This cell line lacks expression of wild-type RB protein, but contains a cytoplasmic, carboxy-truncated 95 kDa protein which cannot bind SV40 T-antigen. Saos 2 cells respond to expression of exogenously added gene encoding RB, introduced by retrovirus mediated gene transfer, by an initial enlargement of cell size and loss of tumorigenicity of cells transferred to nude mice. Hence, it was determined that these cells might be particularly sensitive to injection of RB protein.

The cell line SR-40, which stably expresses exogenous RB gene to RB protein, was derived from Saos-2 by single cell cloning after infection with a retrovirus carrying the RB gene as described in *Science* (1988) 242:1563–1566. African Green monkey kidney cell lines CV-1 and COS-7 were also obtained from American Type Culture Collection. COS-7 was derived from CV-1 by transformation with an origin-defective SV-40 as described in *Cell* (1981) 23:175–182. All the cells were cultured in Dulbecco's modified Eagle's medium plus 10% fetal calf serum as recommended.

Cells were synchronized at the G1/S boundary by isoleucine starvation for 36 hours and then incubated in complete medium supplemented with either aphidocolin or hydroxyurea (both from Sigma) for an additional 12 or 16 hours respectively using the method in *Proc. Natl. Acad. Sci. USA*. (1982) 79:4083–4087. Cells were released from G1/S block by washing three times with phosphate buffered saline (PBS) and re-feeding with complete media. Metaphase arrested cells were collected after an 8 to 12 hour treatment with 0.04 μg/ml nocodazole (Sigma) as described in *Exp. Cell Res.* (1980) 126:397–405. To increase the yield of mitotic cells, cells were first arrested at the G1/S boundary by a 12-hour treatment with aphidicolin. Six hours after the removal of aphidocolin, nocodazole was added to the medium. Mitotic cells were collected by gentle washing and shaking and were then replated onto 35 mm dishes. Six hours after seeding, the unattached cells were washed away and cells were injected at various times thereafter.

Preparation of RB Proteins

Two forms of RB protein were prepared for the microinjection experiments. Recombinant full length RB protein, (p110$^{RB}$ both hypophosphorylated and unphosphorylated forms) was purified to near homogeneity from baculovirus infected insect cells. At concentrations approaching 1 mg/ml however, the protein aggregated into a form which could not be injected. To partially alleviate this problem, RB protein was purified, stored, and injected in buffers containing 10% glycerol. An unphosphorylated, amino-truncated 56 kDa RB protein (p56$^{RB}$ or truncated RB protein), containing an intact T-antigen binding domain, was expressed in *E. coli* and purified to near homogeneity. Since the truncated protein could be concentrated to 1 mg/ml and injected in a standard buffer containing 2% glycerol, it was used in most of the following experiments.

p56$^{RB}$ ("RB truncated protein") is the C-terminal half of the RB protein and contains both regions essential for SV40 T-antigen binding. It is produced in *E. coli* from a T7 RNA polymerase expression system as disclosed in *Nature* (1991) 350:160–162. p110$^{RB}$ is produced in insect cells by recombinant means as disclosed above and in *Cell Growth and Diff.* (1990) 1:429–437.

Both p110$^{RB}$ and p56$^{RB}$ proteins were purified to homogeneity by conventional chromatography. Histone H1 and rabbit anti-goat IgG were purchased from Boehringer Mannheim and Vector laboratories, respectively. Antibodies 0.495 (against the TRP E-RB fusion protein consisting of sequences from exons 19–22), 0.47 (against the TRP E-RB fusion protein containing sequences from exons 23–27 of RB) and R2 were concentrated in microinjection buffer to an approximate concentration of 1 mg/ml. The T peptide and p53 peptides were the gift of Nicholas Lin. These antibodies are described in *EMBO J*. (1990) 9:1815–1822. The T peptide comprises amino acids 101–118 and was dissolved in microinjection buffer at 1 mM or 5 mM as described in *Cell* (1989) 56:57–65. The mutant T peptide contains a lysine to aspartic acid substitution and was used at 5 mM, *Cell* (1989) supra. The p53 peptide was dissolved in microinjection buffer at 5 mM.

Protein preparations, except the full-length RB protein, were concentrated in an injection buffer containing 20 mM Tris, pH 7.4; 0.1 mM EDTA; 10 mM KCl; 1 mM 2-mercaptoethanol and 2% glycerol using the Centricon 30 micro-concentrator (Amicon). $p110^{RB}$ was kept in a buffer containing 10% glycerol to reduce aggregation.

For the experiments described in this section (III.), when the retinoblastoma gene is referred to, it is intended to mean the gene having the nucleotide sequence depicted in FIG. 2. When reference is made to the RB protein ($pRB^{110}$) the protein having the amino acid sequence also depicted in FIG. 2 is also intended. With reference to FIG. 2, the truncated protein fragment, $p56^{RB}$ is illustrated. In addition, the $p56^{RB}k$, fragment is depicted in FIG. 2 as commencing at arrow A and terminating at arrow B. With further reference to FIG. 2, the C terminal peptide is illustrated, commencing at amino acid 917 (arrow C) and terminating at amino acid 928 (arrow B).

Protein preparations were analyzed by SDS-PAGE using standard techniques. FIG. 12 shows the concentration and purity of protein preparations used in the microinjection techniques discussed below. The protein preparations used for microinjection were analyzed by SDS-PAGE. Lane 1: $p110^{RB}$ from insect cells infected with recombinant RB baculovirus; lane 2: biotinylated rabbit anti-goat antibody; lane 3: anti-RB 0.495 antibody; lane 4: anti-RB R2 antibody; lane 5: anti-RB 0.47 antibody; lane 6: histone H1; lane 7: $p56^{RB}$ from *E. coli*. One microliter of each sample was loaded on a 15% acrylamide gel. The gel was stained with Coomassie brilliant blue. The positions of molecular weight standards, in kiloDaltons, are indicated.

Injections into cells were performed directly on cells growing on 35 mm culture dishes using an Eppendorf micromanipulator and microinjector with femtotip capillary micropipets. Injection pressure was typically set between 50–100 hPa with an injection time of 0.3–0.5 seconds. It was estimated that the protein preparations were diluted approximately 20 to 50-fold upon injection. Assuming a typical cell volume of 50–100 picoliters and concentration of the RB truncate at 0.5–1 milligram per milliliter, about 5–50 million molecules were injected per cell.

After injection, the growth media was supplemented with BrdU (Amersham) according to manufacturer's recommendations. Following the appropriate labeling period, media was removed and cells were washed 3× with PBS. Cells were then fixed by incubation with ice-cold, absolute methanol for 30 minutes. After re-hydration by washing with PBS, specimens were incubated with a mouse monoclonal antibody directed against BrdU (Amersham) for one hour at room temperature. After washing 3× with PBS, a fluorescein conjugated anti-mouse antibody (Amersham) was added and incubation was continued for an additional hour at room temperature. The anti-mouse antibody was removed by washing 3× with PBS, and the specimens were incubated with Texas Red conjugated streptavidin (Amersham). The streptavidin bound to the biotinylated RαG co-injected with all protein preparations and thus served as a cytoplasmic marker for injected cells. After a final wash, a solution composed of equal volumes of glycerol and PBS was added and the specimens were covered with a glass coverslip. Specimens were examined under a fluorescent microscope with Texas Red and Fluorescein filters.

The following examples demonstrate the experimental results achieved after introduction of RB proteins into tumor cell lines. Specifically, the examples show the capacity of the RB proteins, or fragments thereof, to arrest progression of a cell infected with exogenously added RB protein, through the cell cycle. In addition, the examples demonstrate that the effect of the blocking can be relieved by SV40 T antigen.

In certain specific examples, the RB gene product was used to arrest the cell cycle progression of an osteosarcoma cell line, Saos-2, treated with full length RB protein or a fragment thereof. It was discovered that cell cycle progression was arrested in G1 and that this progression is reversible.

Figure 14A:
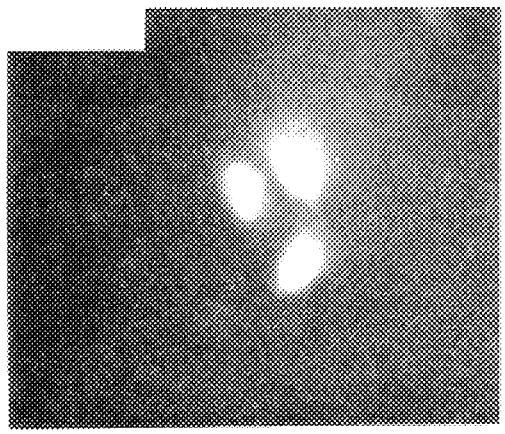
FIGS. 14A through 14F are photomicrographs depicting microinjection and immunostaining of labeled Saos-2 cells.
Figure 14B:
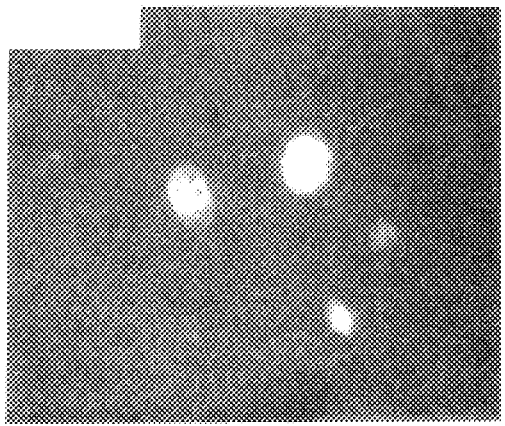
Figure 14C:
Figure 14D:
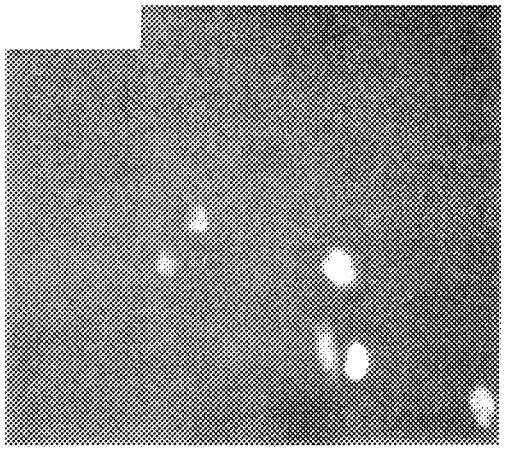
Figure 14E:
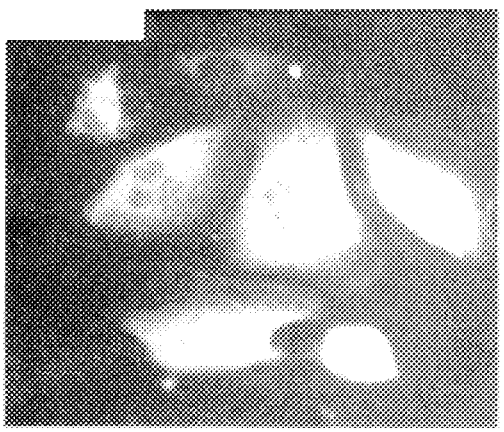
Figure 14F:
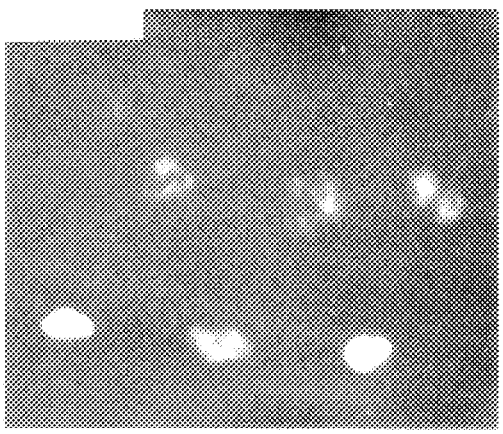

In FIGS. 14A through 14F, there is depicted the results of microinjection and immunostaining of Saos-2 cells labeled with BrdU. Saos-2 cells were injected as described herein. FIG. 14A shows cells injected with $p56^{RB}$, immediately fixed, and indirectly immunostained for RB protein with Texas Red. FIG. 14B contains uninfected cells labeled with BrdU for 4 hours, and then fixed and immunostained with fluorescein conjugated anti-BrdU antibody. FIGS. 14C and 14D are a single field of synchronized cells co-injected in early G1 with $p56^{RB}$ and RαG, incubated with BrdU for 24 hours, then fixed and stained. The cells stained with Texas Red mark injected cells, while the cells stained with fluorescein indicate cells which have incorporated BrdU. FIGS. 14E and 14F are a single field of cells also injected in early GI with RαG alone.

To determine if the proteins could cross the nuclear membrane and be translocated into the nucleus, subconfluent, asynchronously growing Saos-2 cells were cytoplasmically microinjected with $p56^{RB}$ or $p110^{RB}$ and fixed 5 to 15 minutes later. The cells were then immunostained with rabbit anti-RB antibody 0.47 and a Texas Red conjugated anti-rabbit antibody. Staining was mainly observed in the nucleus (FIG. 14), although there was some staining observed in the cytoplasm of some injected cells. Both $p110^{RB}$ and $p56^{RB}$ proteins were capable of being transported to the nucleus within 15 minutes.

For subsequent experiments, cells were typically coinjected with an RB protein and a biotinylated, polyclonal rabbit anti-goat antibody (RαG) that served as a cytoplasmic marker for injected cells. It was estimated that 5–50 million molecules of RB protein were injected per cell. The number of endogenous RB protein molecules per cell was estimated to be approximately 1 million. Hence the injected protein represented at least a 5 to 50-fold excess over endogenous levels. Following injection, the cells were incubated in growth media containing bromodeoxyuridine (BrdU). Cells progressing through S phase during the labeling period will incorporate BrdU into their DNA. After fixation, cells were immunostained for BrdU with a fluorescein-conjugated antibody and for RαG with Texas Red conjugated streptavidin (FIG. 14). The percentage of injected cells that incorporated BrdU could be determined under a fluorescence microscope as the fraction of Texas red-positive cells that were also fluorescein-positive.

BrdU incorporation in RB-injected, asynchronously growing cells was only slightly less than that of uninfected cells or cells injected with RαG alone over a four hour labeling period (Table 1). These results indicated that the RB protein preparations used were not generally toxic to cells as determined by their continued viability, DNA incorporation, and cell adherence.

TABLE 1

Microinjection of Asynchronously Growing Cells

| Protein Sample | Total Number of Injected Cells[a] | Total Number of BrdU Stained Cells[b] | % Injected Cells Entering S Phase |
|---|---|---|---|
| pp110$^{RB}$ | 1094 | 416 | 38 |
| p56$^{RB}$ | 1315 | 408 | 31 |
| RαG | 1725 | 707 | 41 |
| Histone | 106 | 42 | 40 |
| Uninfected | | | 41 |

[a]The total number of injected cells (Texas Red positive) counted from at least five independent experiments, except for the Histone injection which represents one experiment.
[b]The number of injected cell which incorporated BrdU as evidenced by uniform staining with a fluorescein linked anti-BrdU antibody. Cells were incubated in growth media with BrdU for 4 hours prior to staining.

Since only a small effect on BrdU incorporation was observed upon injection of RB protein, the cells might only be sensitive to RB protein at a particular point in the cell cycle. To test this hypothesis, RB was injected into synchronized cells. Cells were synchronized by treatment with nocodazole, which arrest cells in mitosis, and were then released and incubated for an additional 6 hours at which time non-adherent cells were removed and the remaining cells injected. Following a 24 hour incubation in the presence of BrdU, cells were fixed and stained for BrdU and RαG. At least 80–90% of uninfected cells could be stained for BrdU. Cells injected with the 56 kD truncated protein, however, were almost completely inhibited from progressing through Gi and into S phase over the labeling period. In this regard, please see Table 2 and FIGS. 14C and 14D. Similar inhibition was observed upon injection with full length RB protein. In contrast, 60–70% of cells injected with histone and RαG, or RαG alone were able to enter S phase during the labeling period (FIGS. 14E and 14F). Although full length RB protein inhibited BrdU incorporation under these conditions, results were somewhat variable. Over time, the RB protein preparations tended to aggregate which led to difficulty in injection. Relative to preparations of full length and truncated RB protein activity was very consistent.

To extend this observation to cells which already expressed wild-type full length, truncated RB protein was injected into cell line SR-40 which was derived from Saos-2; it stably expresses full length RB protein. The effect of RB protein injection at early G1 phase on synchronized SR-40 cells was identical to the effect on Saos-2 cells (Table 2); very few cells injected with the RB truncated protein entered S phase over the 24 hour labeling period. Thus, the presence of endogenous wild-type full length RB protein did not interfere with the effect of the RB truncated protein on cell cycle progression.

To determine how long the RB truncate blocked entry to S phase lasted, the labeling period in the presence of BrdU was extended from one day to 2 or 4 days. FIG. 15 graphically shows the number of injected Saos-2 cells which incorporated BrdU during the labeling period. Saos-2 cells were co-injected with 56 kD RB protein and RαG 6–7 hours after release from nocodazole treatment. After injection, cells were incubated in media supplemented with BrdU for the indicated number of days before fixing and staining. The percentage value indicates the number of injected cells which had incorporated BrdU during the labeling period. The values represent at least 100 injected cells. Inhibition of cell cycle progression was still observed after 2 days of incubation with BrdU prior to fixing and staining. Four days after injection, 80% of cells injected with the RB truncated protein were able to incorporate BrdU. These observations indicated that the block of cell cycle progression by this RB protein was reversible, and lasted between 2 and 4 days.

The dose dependence of the truncated RB protein effect was also measured. Diluted aliquots of the protein were injected into synchronously growing cells in early G1 phase. FIG. 16 graphically shows the dependence of cell cycle arrest on the dose of p56$^{RB}$. Saos-2 cells were co-injected 6–8 hours after release from nocodazole treatment with the indicated concentrations of the truncated protein and 1 mg/ml of RαG. After 24 hours of incubation in growth medium with BrdU, cells were fixed and stained for BrdU and RαG. The histogram indicates the percentage of injected cells which incorporated BrdU. Each value represents at least 150 injected cells. As shown in FIG. 14, 5-fold dilution of the truncated RB protein from the original concentration diminished the inhibitory activity while aliquots diluted by up to 2-fold still retained the inhibitory effect. Therefore, the block of entry into S phase by p56$^{RB}$ was dependent on the amount of protein injected. The threshold for block of BrdU incorporation was between 0.2 and 0.5 mg/ml of injected RB protein.

To demonstrate that the inhibition of entry into S phase was caused by RB protein, the block was alleviated with reagents that bound specifically to the truncated protein. The RB protein (p56$^{RB}$) was mixed with 1 mg/ml solutions of rabbit polyclonal antibodies 0.495, 0.47, or R2. These antibodies were raised against unique RB fusion proteins, and recognized the RB truncated protein on Western blots. Injection of the mixture of the RB truncated protein and 0.495 resulted in BrdU incorporation in about 30% of injected cells, compared to an almost total lack of incorporation in cells injected with this protein alone (Table 2). Cells co-injected with this RB protein and antibody 0.47 incorporated BrdU about 16% of the time. Co-injection of the truncated RB protein and antibody R2 also exhibited a lessened inhibitory activity although the effect was not as dramatic as with antibodies 0.47 or 0.495. Because antibodies that bind RB protein diminished the inhibitory effect of this protein, the block to BrdU incorporation was due specifically to RB protein.

TABLE 2

Microinjection of Synchronously Growing Cells in Early G1.

| Cell Line | Protein | Number of Injected Cells[a] | Number of BrdU Stained Cells[b] | % of Injected Cells Entering S Phase |
|---|---|---|---|---|
| Saos-2 | p110$^{RBc}$ | 256 | 8 | 3 |
| | RαG$^c$ | 270 | 173 | 64 |
| | p56$^{RB}$ | 388 | 12 | 3 |
| | RαG | 295 | 202 | 68 |
| | Histone | 595 | 333 | 56 |
| | Uninfected | | | 84 |
| | p56$^{RB\ d}$ | 247 | 10 | 4 |
| | p56$^{RS\ d}$ + .495 | 80 | 24 | 30 |
| | p56$^{RB\ d}$ + 596 | 95 | 16 | |
| | p56$^{RB\ d}$ + R2 | 712 | 43 | 6 |

TABLE 2-continued

Microinjection of Synchronously Growing Cells in Early G1.

| Cell Line | Protein | Number of Injected Cells[a] | Number of BrdU Stained Cells[b] | % of Injected Cells Entering S Phase |
|---|---|---|---|---|
| SR-40 | p56$^{RB}$ | 89 | 3 | 3 |
| | Histone | 201 | 105 | 52 |
| | RαG | 134 | 74 | 55 |

[a]The total number of injected cells (Texas Red positive) counted from at least three independent experiments.
[b]The number of injected cells which incorporated BrdU as evidenced by uniform staining with a fluorescein linked anti-BrdU antibody. Cells were incubated in growth media with BrdU for 24 hours after injection and prior to staining.
[c]Injections were performed in a buffer containing 10% glycerol.
[d]The truncated RB protein was injected at a concentration of about .3–.5 mg/ml, rather than 1 mg/ml, in these experiments.

BrdU Incorporation is not Inhibited by the Truncated RB Protein if Injected in S Phase The lack of BrdU incorporation observed after injection of RB protein in early G1 phase could be explained by inhibition of DNA synthesis. To test this, Saos-2 cells were arrested in early S phase by treatment with aphidicolin and then injected with the truncated RB protein. As shown graphically in FIG. 17, BrdU incorporation is not inhibited by this RB protein if it is injected in the S phase. Saos-2 cells were arrested at G1/S by treatment with hydroxyurea or aphidocolin and were then injected.

After injection, cells were released from arrest and incubated with BrdU for 6–8 hours (hydroxyurea) or 4–6 hours (aphidicolin) at which time the cells were fixed and stained. Cells were also arrested in mitosis by treatment with nocodazole. After release, cells were collected and injected about 6 hours later. Following injection, cells were incubated with BrdU for 24 hours and then fixed and stained.

The protein preparations used for injection are indicated. The percentage of injected cells that stained for BrdU after the respective labeling period is shown. After injection, cells were released from aphidicolin treatment and incubated with BrdU for 4–6 hours, fixed, and immunostained for BrdU and RαG as described. In contrast to cells injected in early G1, approximately 60% of injected, truncated RB protein, aphidicolin arrested cells stained positively for BrdU incorporation. The percentage of cells entering S phase and the intensity of BrdU staining was similar to cells injected with histone and RαG, or RαG alone. To control for any possible lag period of the function of RB protein after injection, aphidicolin arrested cells injected with the RB protein were incubated for an additional 6 hours prior to release and labeling with BrdU. Despite a somewhat lower intensity of BrdU staining, which was probably caused by the prolonged incubation with aphidicolin itself, the percentage comparable to that of cells injected with RαG alone.

Similar experiments were performed by arresting cells with hydroxyurea rather than aphidicolin. Hydroxyurea arrests cells near the G1/S boundary at a point distinct from aphidicolin arrest. Saos-2 cells were arrested near G1/S by treatment with hydroxyurea and then were injected with the truncated RB protein. After injection, cells were released from hydroxyurea treatment and labeled for 6 to 8 hours with BrdU. Again, injection of the truncated protein had no detectable inhibitory effect on BrdU incorporation (FIG. 17). The percentage of cells synthesizing DNA was the same whether injecting with RB protein and RαG, histone and RαG, or RαG alone.

The results were consistent with observations of asynchronously growing cells injected with RB protein, and implied that DNA synthesis, per se, was not blocked significantly by the RB truncate. Therefore, inhibition of DNA synthesis could not explain the complete lack of BrdU incorporation seen upon injection of the protein into synchronized cells in early G1 phase.

RB Protein Blocks Progression through the G1 Phase at a Specific Point

Given the results of the above experiments, the inhibitory effect of the truncated RB protein must have been due to a block in progression through the G1 phase. To define the position of this arrest within the G1 phase, a careful calibration of the time of onset of S phase in the cell cycle of Saos-2 cells was first determined. FIGS. 18A through 18C graphically depict the dependence of cell cycle arrest on the time period of injection for the truncated protein. With regard to FIG. 18A, Saos-2 cells were arrested in mitosis by treatment with nocodazole. After release from arrest, the cells were incubated for the indicated number of hours in the presence of BrdU, then fixed and stained with an anti-BrdU antibody. The histogram indicates the percentage of counted cells that stained for BrdU. Each value represents at least 200 cells.

As shown in FIG. 18A, uninfected cells began to stain for BrdU at approximately 20 hours after the release. By 30 hours, virtually 80 to 90 percent of cells had incorporated BrdU.

Based on this, a time-course experiment in which nocodazole treated cells were injected with the p56$^{RB}$ protein at various times after release from arrest was then performed. FIG. 18B depicts the time of onset of S phase in Saos-2 cells, in hours, after release from nocodazole arrest in mitosis. The length of G1 phase is about 22 to 24 hours. The length of S phase is about 7 to 8 hours. The length of the G2 phase has not been precisely determined. The arrows indicate the time points of injection that are used for the experiment described in the legend to FIG. 18C.

With regard to FIG. 18C, Saos-2 cells were co-injected with 1 mg/ml the truncated RB protein and RαG at the indicated times, in hours, after release from nocodazole treatment. Incubation was continued after injection in growth medium with BrdU until 30 hours after the original release from nocodazole. After BrdU labeling, cells were fixed and stained for BrdU and RαG. The histogram shows the percentage of the protein injected cells which incorporated BrdU. Each value represents at least 200 injected cells.

Very few cells entered S phase at 30 hours after release if injected with the protein 5–10 hours after release from nocodazole (FIG. 20C). A significant number of cells incorporated BrdU if injected with the truncated RB protein after 14–16 hours post-arrest. If injected 17–19 hours after release, the truncated RB protein had no detectable inhibitory effect on entry into S phase.

Given that S phase began between 22 and 24 hours after release from nocodazole, the results suggested that cells become refractory to the inhibitory effect of injected RB protein about 6–10 hours prior to the G1/S transition. This confirmed the notion that the inhibitory effect of RB protein on the cell cycle was due to a block in progression through the G1 phase rather than a block of DNA synthesis itself. Furthermore, the observations implied that RB may function at a specific, relatively early time point within the G1 phase.

SV40 T Antigen Relieves the Blocked Cell Cycle Progression by the Truncated RB Protein As a test of the hypothesis that SV40 T-antigen can functionally inactivate RB protein upon binding, the effect of the truncated RB protein injection on G1 progression in the presence or absence of SV40 T antigen was compared. A 1 mM T peptide solution which was capable of binding to the p56$^{RB}$, was mixed with an equal volume of the truncated RB protein and injected into synchronized cells in early G1 phase. At this concentration, the peptide was at a 100 to 200-fold molar excess over the RB protein. About 28% of synchronized cells injected with the truncated RB protein/T peptide mixture entered S phase during the labeling period (Table 3). If the T peptide concentration was increased to 5 mM, or a 500 to 1000-fold molar excess, approximately 70% of injected cells could incorporate BrdU. By contrast, almost none of the cells progressed into S phase after injection with the truncated RB protein and a 500 to 1000-fold molar excess of a carboxy-terminal p53 peptide that did not bind the truncated RB protein.

The effects of injection of the truncated RB protein on African Green monkey kidney cell lines CV-1 and COS-7 were also compared. COS-7 cells were chosen since they were derived from CV-1 cells by transformation with an origin-defective SV-40 mutant, and they expressed a high level of T-antigen. Therefore, they can serve as a good system for testing the effect, if any, of the presence of endogenous T-antigen on the activity of the injected RB protein. The percentage of synchronized CV-1 cells injected with the truncated RB protein in early G1 phase that incorporated BrdU was at least 5-fold lower than cells injected with RαG alone (Table 3). Synchronized COS-7 cells, however, were not inhibited at all from progressing into S phase. These results indicated that the presence of endogenous T-antigen, or co-injection with a T-antigen peptide, could neutralize the inhibitory activity or RB protein. Thus, those skilled in the art can utilize this system to screen RB protein fragments to identify those fragments capable of blocking cell cycle progression by comparing the percentage of CV-1 to COS-7 cells entering S phase in the presence of the RB protein fragment.

The foregoing results provide functional evidence which indicates that RB protein can act by inhibiting progression through the cell cycle. Injection of the truncated p56$^{RB}$ protein does not detectably inhibit DNA synthesis per se, since aphidicolin or hydroxyurea arrested cells are not affected, but rather blocks progression through the G1 phase. This inhibition of cycle progression is dose-dependent, it is not due to general toxicity to the cells, and it is specific for RB protein because antibodies that bind specifically to the truncated RB protein can attenuate its activity. The cycling cell is sensitive to RB protein inhibition until roughly 6–10 hours before the onset of DNA replication; after this time, exogenously added truncated RB protein no longer inhibits progression into S phase. Assuming there is a small lag period between the truncated RB protein injection and its appearance in an active form in the nucleus, it may be concluded that RB protein inhibits progression to S phase at a critical point in G1 phase. The 6–10 hour time window prior to DNA synthesis may be analogous to the time period following the G1 restriction point, a point of irreversible commitment to S phase in mammalian cell lines.

The time window defined may not correspond precisely to the time point when RB protein functions under normal physiological conditions. The time it takes for injected full length RB protein or the truncated RB protein to appear in an active configuration and/or location is not clear from these experiments. However, RB proteins are transported to the nucleus within 15 minutes after cytoplasmic injection, and continued incubation of the cells injected with the truncated RB protein with aphidicolin for several hours prior to release and labeling does not decrease the percentage of cells which incorporate BrdU. These observations show that the time it takes RB protein to become functional after injection is short.

The transition from an active form of the full length RB protein to an inactive form has been assumed to occur at the G1/S boundary since the protein undergoes extensive phosphorylation at this point. However, because of the foregoing, an earlier time period, which seems to be critical for the truncated RB protein activity has been defined. Thus, RB may be involved in a regulatory decision which the cell makes at a point about 6–10 hours prior to the G1/S transition. The RB protein can be phosphorylated at multiple sites both in vivo and in vitro, yet it is not yet clear which phosphorylation sites are important for RB function. Subtle increases in phosphorylation of during G1 phase may be responsible for the cells' transition from an RB-responsive to a non-responsive state. Some phosphorylation of the recombinant, full length RB protein has been observed in the G1 phase, although this may have been due to incompletely synchronized cells.

The carboxy-terminal 56 kilodaltons of RB is sufficient to inhibit progression through the G1 phase. This indicates that the carboxy terminal half of the recombinantly produced, full length protein is, in fact, a functional domain with respect to its effect on the cell cycle. Two biochemical activities have been ascribed to the carboxy-terminal half of this protein, DNA binding and protein binding. Based on findings to date, the sequence specificity of RB binding to DNA is low; although RB binds with slightly higher affinity to DNA with high G/C content, no particular sequence is strongly preferred. On the other hand, specificity has been observed in binding of RB to proteins. The transforming proteins of several DNA transforming viruses as well as a subset of cellular proteins bind to the same domain of the recombinantly produced, full length RB protein therefore can compete with one another for RB protein binding. This region is where the majority of naturally occurring inactivating mutations of RB are located. It seems likely, then, that the block to progression of G1 phase by RB protein is dependent on specific protein-protein interactions.

Mixing the truncated RB protein with an SV40 T-antigen derived peptide, which can bind the truncated RB protein, eliminates its inhibitory consequences. Co-injection of the truncated RB protein with a T peptide containing a single amino acid substitution at a 500 to 1000-fold molar excess can also attenuate, to some extent, the block to cell cycle progression. Although the amino acid substitution lowers its affinity for RB protein in vitro, this mutant T peptide may still bind the truncated RB protein in vivo when present in vast molar excess. In contrast, injection of a totally irrelevant p53 peptide had no effect on the inhibitory activity of RB protein, which thus substantiated the specificity of the interaction observed between RB protein and T-antigen peptide. CV-1 cells injected in early G1 with the truncated RB protein are arrested before S phase while COS-7 cells, which express high levels of T-antigen, are not arrested, however. These observations, taken together, indicate that T-antigen binding does have functional consequences for RB protein. Since the injected the truncated RB protein is unphosphorylated, the test results are consistent with the hypothesis that the active form of RB protein, with respect to its inhibition of cell proliferation, is the unphosphorylated form. Therefore, the transforming proteins of some DNA tumor viruses, including SV40 T-antigen and adenovirus E1A, may promote cell growth, at least in part, by binding and inactivating underphosphorylated recombinantly produced full length RB protein. The immortalization of cells and the induced escape from quiescence upon expression of these transforming proteins are phenotypes consistent with deregulation of the cell cycle.

Given that the carboxy-terminal half of RB protein is biologically active, the question remains as to the function of the amino terminal half of the protein. Sequences within this region may be required for the proper phosphorylation of the protein. In murine cells, polypeptides similar to the truncated RB protein are not hyperphosphorylated. Also, several consensus sites for the cdc2/MPF kinase are present within this region. It follows that the amino terminal half of the RB protein may contain a regulatory domain which can modulate RB function. Release of the truncated RB protein block to G1 progression does not occur until 3–4 days after injection; this lengthy arrest period may be due to the inability of the cell to regulate RB protein in a normal manner, or to the relatively large amount of RB protein injected. A comparison of the activity in this assay of different RB proteins with mutations in phosphorylation sites would aid in resolving this issue. If the truncated RB protein is constitutively active, mutations creating such polypeptides would be expected to inhibit cell proliferation and thus place cells at a selective disadvantage. This may explain the lack of naturally occurring mutants within the amino terminal half of RB.

The results described here indicate that RB participates in control of cell cycle progression by acting at a control point within the G1 phase. This point is significantly earlier than the observed hyper-phosphorylation of the recombinantly produced RB protein as cells enter S phase. Thus, it is reasonable to propose a model which incorporates the test results as well as other known properties of the RB protein. Since RB has been shown to associate with several cellular proteins, and the protein binding domains of RB are sufficient to block cell cycle progression, it seems highly possible that the binding of cellular proteins is critical for the observed RB function. The model suggests that RB participates in regulation of the cell cycle by sequestering cellular proteins vital for DNA synthesis and/or cycle progression at a particular time period during the G1 phase. Inactivation of $p110^{RB}$ by mutation, by phosphorylation at key sites, or by binding with transforming proteins, permitting them to provide functions that are necessary for continuation of the cell cycle. Once cells commit themselves to continuation of the cell cycle by release of these proteins, full length RB protein can no longer effectively inhibit their function and therefore the block to cell cycle progression is relieved.

Sub-nuclear localization of RB may be crucial to its ability to sequester other proteins in an inactive form. RB protein segregates other proteins in an inactive form. RB protein segregates with cellular replication proteins to sites of Herpes virus DNA replication upon infection, a situation where normal regulation of the cell cycle is subverted. In G1, the underphosphorylated form of recombinant, full length RB is tightly associated with a particular nuclear locale. This purified protein also tends to polymerize, perhaps explaining the difficulty in maintaining its solubility at high concentrations, and it has limited homology to a certain class of intermediate filament proteins. These observations suggest that the recombinant full length protein may contribute to some structural component of the nucleus, and that association of this protein with this component is necessary for its inhibition of cell cycle progression. The hyperphosphorylation would presumably free the protein from its sub-nuclear location allowing it to provide some other function, or to reset its ability to sequester other proteins during the subsequent cell cycle. The model predicts that regulation of RB activity could be accomplished by specifying its nuclear location and/or the cellular proteins to which it binds.

The biological consequence of complete loss of RB gene and/or protein function is the generation of retinoblastoma tumors and some secondary tumors. Involvement of RB in the cell cycle provides a means to explain this phenomenon. RB may act to halt progression through G1 phase until the cell receives proper signals for commitment to continuation of the cell cycle. Thus, loss of RB function may contribute to tumor formation in different tissues by permitting unscheduled cell proliferation.

In view of the foregoing, it can be seen that the RB gene product is a nuclear phosphoprotein which undergoes changes in the phosphorylation status in synchrony with the cell cycle. To test whether RB regulates cell cycle progression, purified RB proteins, either full-length or a truncated form containing the T-antigen binding region, were injected into cells and the effect on entry into S phase determined. Synchronized cells injected early in G1 with either protein are inhibited from progressing into S phase. This effect is antagonized by co-injection with antibodies directed against RB. Injection of RB protein into cells arrested at the G1/S boundary or 6–10 hours before the end of G1 has no effect on BrdU incorporation suggesting that RB protein does not apparently perturb DNA synthesis in S phase. These results provide direct evidence that RB may regulate cell proliferation by restricting cell cycle progression at a specific point in Gi, and they also establish a biological assay for the activity of RB protein. Co-injection of RB protein with a T-antigen peptide, or injection into cells expressing T-antigen does not prevent cells from progressing into S phase. This experiment substantiates the hypothesis that T-antigen binding has functional consequences for RB protein.

TABLE 3

SV40 T-antigen relieves the block to G1 progression by $p56^{RB}$.

| Cell Line | Protein[a] | Number of Injected Cells[b] | Number of BrdU Stained Cells[c] | % of Injected Cells Entering S Phase |
|---|---|---|---|---|
| Saos-2 | $p56^{RB}$ | 247 | 10 | 4 |
|  | $p56^{RB}$ + T | 724 | 203 | 28 |
|  | $p56^{RB}$ + p53 | 727 | 7 | 1 |
| CV-1 | $p56^{RB}$ | 459 | 46 | 10 |
|  | Histone | 471 | 259 | 55 |
|  | RαG | 332 | 176 | 53 |
| COS-7 | $p56^{RB}$ | 257 | 224 | 87 |
|  | Histone | 191 | 159 | 83 |

[a]All proteins were injected at concentrations of about 1 mg/ml, except for $p56^{RB}$ in Saos-2 cells which was injected at about .3–.5 mg/ml.
[b]Cell lines are microinjected 6–8 hours after release from nocodazole treatment. The total number of injected cells (Texas Red positive) is indicated.
[c]Cells were incubated in growth media with BrdU for 24 hours after injection and prior to staining.

V. EXOGENOUS RB PROTEIN INHIBITS TUMOR GROWTH

Purification of RB Protein $p110^{RB}$ was purified from *E. coli* BL21 (DE3)/pLyS/pETRBc using a modification of the method described in

*Nature* (1991) 350:160–162. Briefly, 120 g of wet cell paste was resuspended in lysis buffer, (10 mM Tris-Cl, 10% glycerol, 1 mM EDTA, 1 mM DTT, 1 mM benzamidine, 1 μg/mL leupeptin, pH 8.5) processed through a microfluidizer at 13,000 psi and the soluble fraction was brought to 50% ammonium sulfate. Precipitated protein was recovered by centrifugation at 10,000×g and was solubilized in lysis buffer, clarified by centrifugation and dialyzed against lysis buffer. The dialysate was loaded on a phosphocellulose P-11 (Whatman) column in 10 mM Tris-Cl, 10% glycerol, 1 mM EDTA, 1 mM DTT, pH 8.5 and was washed and eluted with a gradient of 0–0.7M NaCl. Fractions containing $p56^{RB}$ and $p110^{RB}$ (as judged by SDS-gel electrophoresis) were pooled and protein was precipitated with 70% ammonium sulfate. The precipitate was recovered by centrifugation and was dialyzed into 20 mM sodium phosphate, 0.2M NaCl, 10% glycerol, 1 mM EDTA, pH 7.5, and was loaded onto a Sephacryl-200 (Pharmacia) sizing column. $p56^{RB}$ was separated from $p110^{RB}$ during this purification step. Pooled fractions of $p110^{RB}$ were then loaded onto a DEAE column (Whatman) and were washed with 10 mM Tris-Cl, 10% glycerol, 1 mM EDTA, pH 8.8 and eluted with a gradient of 0–0.25M NaCl. The $p110^{RB}$ and $p56^{RB}$ used in these studies were >95% pure as judged by Coomassie blue stained SDS-polyacrylamide gels. Purified $p110^{RB}$ and $p56^{RB}$ was dispensed into aliquots and stored frozen at −80° C. in 20 mM sodium phosphate, 0.2M NaCl, 10% glycerol, pH 7.5.

Individual lots of RB protein were assayed for biological activity with NCl-H596 NSCLC cells, using the $^{3}$H-thymidine uptake assay described below. An inactive (control) lot of $p110^{RB}$ was prepared using the procedure described above, except that the lysis and column buffers did not contain glycerol. The inactive lot of $p110^{RB}$ did not result in growth suppression of NCl-H596 cells in vitro at concentrations below 50 μg/mL.

$^{125}$I-$p110^{RB}$ and $^{125}$I-$p56^{RB}$ were prepared from purified $p110^{RB}$ or $p56^{RB}$ protein and $^{125}$I (ICN Biomedical, Irvine, Calif.) using the chloramine-T method (*Nature* (1962) 194:495).

Cell Lines

All cell lines used in this study were obtained from the American Type Culture Collection. Cell lines NCl-H596 (lung adenocarcinoma), A549 (squamous cell lung carcinoma), 5637 (human bladder carcinoma), NCl-H69 (small cell lung carcinoma), MDA-MB-468 (breast carcinoma), Saos2 (osteosarcoma), FHs 738Bl (normal human bladder), MRC-9 and WI-38 (normal human lung) and CCD 976Sk (normal human foreskin fibroblast) were passaged in Dulbecco's modified Eagle Medium: F-12 (v/v) with 2 mM glutamine and 10% (v/v) fetal bovine serum (heat inactivated) in a humidified-air/7% $CO_2$ incubator at 37° C.

Cell line phenotypes: In this study $RB^{pos}$ denotes cell lines in which there is expression of wild-type $p110^{RB}$. $RB^{neg}$ denotes cell lines that produce mutant, nonfunctional RB or cell lines in which RB protein expression is not detectable by immunostaining or western blotting with the α-RB MAb 3C8 (*J. Immunol. Meth.* (1994) 169:231–240).

In Vitro Growth Inhibition Assay

For dose-responsive curves of $p110^{RB}$-mediated growth inhibition, 2×$10^4$ cells were seeded in 96-well plates, allowed to adhere overnight and were incubated with 0–25 μg/mL of RB protein in RPMI-1640, 10% fetal bovine serum (heat inactivated). Assays were performed in triplicate. $p110^{RB}$-containing medium was changed every 6 hours for 72 hours. One μCi of $^{3}$H-thymidine was added to each well 12–18 hours before harvest. Cells were harvested and assayed for $^{3}$H-thymidine uptake as described in *Proc. Natl. Acad. Sci. USA* (1986) 83:4749–4753 and *Anal. Biochem.* (1971) 44:143–153. For the time course of $p110^{RB}$-mediated growth suppression, 2×$10^4$ NCl-H596 ($RB^{neg}$, NSCLC) cells were seeded into 96 well plates and were treated with 50 μg/mL $p110^{RB}$ in RPMI 1640, 10% fetal bovine serum (heat inactivated). Cells were then harvested at the indicated times and assayed for $^{3}$H-thymidine incorporation.

Nuclear Localization of $p110^{RB}$

The time-dependent nuclear localization of $p110^{RB}$ was assessed as follows: NCl-H596 tumor cells were seeded at $10^6$ cells/well (triplicate wells for each time point) in a 6-well plate in RPMI-1640 (10% FBS) and allowed to adhere overnight. 0.75 μCi of $^{125}$I-$p110^{RB}$ was added to the medium in 8 hour intervals for a total of 72 hours. Medium was replaced every 24 hours. A 0, 8, 24, 48 and 72 hours, cells were cooled to 4° C. and residual $^{125}$I-$p110^{RB}$ was removed by sequentially rinsing the cells with 1 ml of PBS three times. Cells were incubated with 0.5 ml of 0.25% trypsin (Irvine Scientific) in normal saline for 5 minutes followed by addition of 4 ml of RPMI-1640 containing 10% fetal bovine serum (heat inactivated). Cells were then harvested and pelleted by centrifugation at 500×g for 5 minutes at 4° C. The supernatant was removed and the cell pellet was resuspended in 1 mL ice cold hypotonic buffer (0.01M Tris-HCl, 1 mM $MgCl_2$, pH 7.6). Cells were homogenized by 15 strokes in a 15 ml dounce homogenizer (Wheaton). The homogenate was centrifuged at 500×g for 5 minutes at 4° C. and the pellet (nuclear fraction) was resuspended in 1 ml ice cold hypotonic buffer. The supernatant, containing the membrane and cytoplasmic fractions was further centrifuged at 10,400×g for 45 minutes at 4° C. The resulting supernatant cytoplasmic fraction was removed and the pellet (membrane fraction) was resuspended in 1 ml ice cold hypotonic buffer. One-tenth (0.1 ml) of each fraction was subjected to liquid scintillation counting (Cytoscint fluid).

Immunoprecipitation and Identification of $^{125}$I-$p110^{RB}$ in NCl-H596 Nuclear Fractions Three (3)×$10^6$ NCl-H596 non-small cell lung carcinoma (NSCLC) cells were seeded in 10 ml RPMI-1640 media (10% fetal bovine serum (heat inactivated)) in 100 mm tissue culture dishes (Costar) and were allowed to adhere overnight. Medium was removed and 10 ml of fresh RPMI-1640 containing 10% fetal bovine serum (heat inactivated) and 0.8 μCi $^{125}$I-$p110^{RB}$ (specific activity 0.008 μCi/μg) was added to each dish. At the indicated time points, cells were washed twice with 5 ml of HBSS, harvested and fractionated as described above. Cells harvested at 48 hours had media replaced with fresh RPMI-1640 containing 10% fetal bovine serum (heat inactivated) and 0.8 μCi $^{125}$I-$p110^{RB}$ at 24 hours. $^{125}$I-$p110^{RB}$ was immunoprecipitated with α-RB MAb 3C8 (disclosed in *J. Immunol. Meth.* (1994) 169:231–240) and immunoprecipitated complexes were fractionated on 8–16% Tris-glycine SDS-polyacrylamide gels, transferred to nitrocellulose and subject to analysis with the Phosphorimager Model SF (Molecular Biosystems). Other lung lines were assayed by the same method except at 24 hour medium was removed and replaced with fresh RPMI-1640 containing 10% fetal bovine serum (heat inactivated) and 0.8 μCi $^{125}$I-$p110^{RB}$. The purity of the nuclear and cytoplasmic fractions were assessed by measuring the enzymatic activity of NADH oxidase and 5'-nucleotidase in each fraction as described in *Biochim. Biophys. Acta.* (1971) 233:334–347 and *Biochem. J.* (1982) 203:245–251.

The comparison of nuclear localization of p110$^{RB}$ and p56$^{RB}$ in NCl-H596 NSCLC cells was performed as follows: 5×10$^5$ NCl-H596 cells were seeded in 1 ml RPMI-1640 media (10% fetal bovine serum (heat inactivated)) in each well of a 6-well tissue culture plate (Costar) and were allowed to adhere overnight. Medium was removed and 1 ml of fresh RPMI-1640 containing 10% fetal bovine serum (heat inactivated) and either 230 pCi $^{125}$I-p110$^{RB}$ (specific activity 9.23 pCi/μg) or 991 pCi $^{125}$I-p56$^{RB}$ (specific activity 39.6 pCi/μg) was added to each of 3 wells. At the indicated time points, cells from 3 wells were washed twice with 1 ml of HBSS, harvested, pooled and the nuclear fraction was isolated as described above. Nucleus-specific radioactivity was quantitated in a β-scintillation counter.

Peritumoral Treatment of Subcutaneous Tumors

Groups of 3 nude mice (Balb/C NCR nu/nu female, Simonsen, Gilroy, Calif.) were each subcutaneously inoculated with either 10$^7$ NCl-H596 (RB$^{neg}$) or 10$^7$ A549 (RB$^{pos}$) NSCLC cells. Tumor bearing mice were randomly assigned to different cages. When tumor size was approximately 9 mm$^2$, subcutaneous injections of RB protein were made around the tumor. Each tumor was divided into 4 quadrants and 25 μg of RB protein was subcutaneously injected into alternating quadrants every six hours for ten days. Each animal received a total of 100 μg of RB protein per day for a total of 1 mg during the 10 day delivery period. Tumor measurements were made in two dimensions using vernier calipers twice a week.

Intravenous Administration of p110$^{RB}$

Thirty-nine (39) female Balb/C nude mice (Simonsen Laboratories, Gilroy, Calif.) received a single subcutaneous injection of ~20×10$^6$ NCl-H596 (NSCLC, RB$^{neg}$) tumor cells. Tumors were permitted to grow for 21 days and external tumor sizes were measured with calipers. Mice were randomized by tumor size into one of four groups each containing 9–10 animals. Mice received single daily dozes (5 doses/week) for a period of 3 weeks of either active p110$^{RB}$, 50 μg/dose; active p110$^{RB}$ 200 μg/dose; or inactive p110$^{RB}$ 200 μg/dose. Biological activity of p110$^{RB}$ was determined by its ability to suppress growth of NCl-H596 tumor cells in the $^3$H-thymidine uptake assay described in FIG. 22. Tumor dimension (l,w,h) and body weights were measured twice per week by two independent investigators and animals were observed daily for signs of morbidity. Tumor volumes were estimated for each animal assuming a spherical geometry of radius equal to one-half the average of the measured tumor dimensions. Comparison of average tumor sizes between each group was performed using the Mann-Whitney U-test as implemented by StatView (Abacus Software, Berkeley, Calif.).

Effect of RB Protein on Tumor Cell Proliferation

The ability of RB protein to selectively inhibit growth of the RB$^{neg}$ non-small cell lung carcinoma line NCl-H596 is shown in FIG. 19. The results demonstrate that NCl-H596 cells are growth inhibited by p110$^{RB}$ in a dose dependent manner. The IC$_{50}$ for p110$^{RB}$ in this assay is approximately 5 μg/ml [~50 nM]. Interestingly, p56$^{RB}$, a C-terminal derivative of p110$^{RB}$ (amino acids 379–928) containing the "pocket" region necessary for growth suppression (*Mol. Cell Biol.* (1993) 13:3384–3391; *Genes and Develop.* (1992) 6:953–964) could only weakly suppress growth in NCl-H596 tumor cells (FIG. 19). More importantly, p110$^{RB}$ preferentially inhibits the RB$^{neg}$ NSCLC line NCl-H596, since the RB$^{pos}$ NSCLC line A549 is not growth inhibited by either p110$^{RB}$ or p56$^{RB}$ (FIG. 19).

The time dependent nature of p110$^{RB}$ mediated growth inhibition of NCl-H596 tumor cells also was investigated. When tumor cells are treated with 25 μg/ml p110$^{RB}$, a decrease in $^3$H-thymidine uptake is observed at 24 hours after the first addition of p110$^{RB}$ (FIG. 20) and maximum growth inhibition occurs at 48 hours. This delay is probably due to a combination of factors including internalization kinetics and the fact that the cell population is non-synchronized.

To demonstrate that the observed growth inhibition could occur in a variety of tumor cell types, four RB$^{neg}$ tumor lines, an RB$^{pos}$ tumor line and four normal epithelial cell lines were simultaneously treated with identical amounts of p110$^{RB}$ (Table 4). All RB$^{neg}$ tumor lines tested show a marked decrease (60–80% inhibition of DNA synthesis) in $^3$H-thymidine uptake at 72 hours. In contrast, the RB$^{pos}$ NSCLC line A549, normal lung epithelium lines MRC-9 and WI-38, normal bladder epithelium FHs 739Bl, and foreskin fibroblast line CCD 976Sk are not growth inhibited under these conditions. These data are consistent with earlier reports for modest effects on cell growth via overexpression of the RB gene in normal cells, although high levels of p110$^{RB}$ expression may be growth inhibitory.

TABLE 4

| Cell Line | Cell Type | RB Status | Relative Growth Rate |
|---|---|---|---|
| Normal Lines | | | |
| FHS739Bl | Bladder epithelium | + | 84 ± 1 |
| CCD976Sk | Foreskin Fibroblast | + | 89 ± 1.5 |
| MRC-9 | Lung epithelium | + | 86 ± 3 |
| WI-38 | Lung epithelium | + | 76 ± 3 |
| Tumor Lines | | | |
| A549 | NSCLC | + | 99 ± 1.5 |
| H596 | NSCLC | − | 11 ± 1.5 |
| NC1-H69 | SCLC | − | 30 ± 8 |
| MDA-MB-468 | breast adenocarcinoma | − | 24 ± 4 |
| 5637 | bladder carcinoma | − | 37 ± 1.5 |

Effect of p110$^{RB}$ on $^3$H-thymidine incorporation in Cell lines at 72 hours. 5 × 10$^3$ cells were seeded into each well of a 96-well plate and allowed to adhere overnight. p110$^{RB}$ was added to the media to a final concentration of 25 μg/mL. Media containing p110$^{RB}$ was replaced every 12 hours for a total of 72 hours. Cells were harvested and $^3$H-thymidine uptake was assayed as described previously. Cell division rates shown are the mean of 12 individual data points and are expressed as the percent of a buffer control ± standard error of the mean. RB status of "+" denotes wild-type RB; RB status of "−" denotes mutant RB or lack of detectable RB expression.

Cellular Uptake and Nuclear Localization of p110$^{RB}$ p110$^{RB}$ is a nuclear phosphoprotein and its interaction with key transcription elements such as E2F underscores its normal regulatory role in the cell cycle (for a review see *TIBS* (1992) 17:312–315 and *Science* (1992) 258:424–429). Thus, if p110$^{RB}$ is entering cells and affecting their growth by its normal pathway, then it must also localize to the nucleus of target cells. Accordingly, $^{125}$I-p110$^{RB}$ was added to cultures of NCl-H596 tumor cells. Cells were harvested and fractionated into membrane, cytoplasm and nuclear enriched components as described in herein. FIG. 21A shows the time-dependent internalization of $^{125}$I-p110$^{RB}$ into various subcellular fractions. Accumulation of acid-precipitable radioactivity occurred most rapidly in the nucleus, although detectable amounts were present in the membrane fraction between 8–14 hours after treatment. The time course (plateau at 48 hours) and nuclear localization (70% of internalized radioactivity in the nucleus) are consistent with the time-dependent growth inhibitory effect of p110$^{RB}$ described earlier in FIG. 21A. To demonstrate that intact 125I-p110$^{RB}$ was present in the nucleus of treated cells, nuclear fractions were isolated. Immunoprecipitates prepared with α-p110$^{RB}$ antibody were fractionated on SDS-polyacrylamide gels and subjected to autoradiography (FIG. 21B). A 110 kD radiolabelled band appeared in a time-dependent manner, indicating the presence of intact $^{125}$I-p110$^{RB}$ in the nucleus. The time-dependent nuclear accumulation of acid precipitable $^{125}$I cpm and immunoprecipitable $^{125}$I-p110$^{RB}$ was also examined in the RB$^{pos}$ lung tumor cell lines MRC-9 and A549 and yielded results similar to that of NCI-H596 (FIG. 21C). These results indicate that the relative insensitivity of these RB$^{pos}$ cell lines to RB protein is not due to their failure to internalize or localize p110$^{RB}$ to the nucleus. The weak growth inhibition response of RB$^{neg}$ lines to p56RB could be explained by the much lower intracellular levels of p56$^{RB}$ attained in the nucleus of target cells (FIG. 21D).

Diagnostic Determination of the ppRB$^{110}$ in the Tissue

Tumor cells disassociated from biopsy tissue from the subject was labeled with 35$^S$ methionine or $^{32}$P-phosphoric acid an immunoprecipitated with anti-ppRB$^{110}$ IgG according to the procedure described above. Alternatively, protein lysates extracted from bioptic tissue can be directly diagnosed using western blotting analysis probed with either radioactive labeled or non-radioactive labeled anti-RB specific antibody. The presence or absence of immunoprecipitated proteins serves as a diagnostic tool in determination of retinoblastoma or other diseases controlled by the retinoblastoma gene.

Tumor Suppressor Protein Therapy of Lung Cancer

Tumor suppressor genes achieve their oncogenic effect following mutation inactivation of both normal alleles. Recognition of the importance of tumor suppressor genes for human cancer first emerged with studies of retinoblastoma. In hereditary retinoblastoma, one inactivated copy of the retinoblastoma (RB) gene is inherited, and the second gene copy is inactivated during growth and differentiation of the offspring. Characterization of the RB gene has shown that it encodes a nuclear phosphoprotein (p110$^{RB}$). p110$^{RB}$ appears to regulate cell cycle progression, at least in part, through its association with several target proteins, including the transcription factor E2F. Alterations in RB gene structure and expression have now been associated with many human malignancies, including cancers of the lung, prostate, mammary glands, urogenital system and hematologic malignancies. Evidence supporting an important clinical role for altered RB gene expression in tumorigenesis is two-fold. First, introduction of a functioning copy of a normal RB gene into tumor cells characterized by RB gene mutations will suppress the malignant phenotype or the target cell. Second, decreased expression of p110$^{RB}$ has recently been shown to indicate a worsened prognosis in acute myelogenous leukemia and early stage bladder cancer patients (reviewed in *Annual Rev. Biochem.* (1993) 62:623–651.

The development of therapies for cancers characterized by RB gene mutations, or alterations in expression of p110$^{RB}$, offers an opportunity to specifically target a large group of cancers that currently are lacking in specific and effective treatments. One option for such a therapeutic is "protein replacement therapy," in which p110$^{RB}$, or a functional derivative of it, is introduced into tumor cells characterized by loss of expression of the wild type tumor suppressor protein. These results show that exogenously added p110$^{RB}$ can enter cells in culture, localize to the nuclear compartment, and inhibit tumor cell DNA synthesis. Furthermore, p110$^{RB}$ administered parenterally in a clinically relevant animal model of human lung cancer can block tumor growth. A truncated version of p110$^{RB}$, called p56$^{RB}$ also has limited activity in an in vivo model. These results provide further support for the application of tumor suppressor protein therapy for human lung cancers characterized by defective RB expression.

p110$^{RB}$ Inhibits Tumor Formation in vivo

The above described observations of RB-mediated growth suppression in vitro was extended to a nude mouse xenograft tumor model. Accordingly, subcutaneous NCI-H596 tumors were established in nude mice and RB protein therapy was initiated and maintained for 10 days. The subcutaneous, peritumoral administration of RB protein caused a substantial inhibition in tumor growth (FIG. 24). Tumor sizes in p110$^{RB}$-treated mice did not increase significantly for approximately 8 weeks, whereas tumors progressed more rapidly in mice treated with P56$^{RB}$ or control buffer. The effect of RB protein treatment is long lasting, since at day 75–90 the rate of increase in tumor mass in p110$^{RB}$-treated mice (~3 mm$^2$/day) is substantially less than that of buffer treated mice (~20 mm$^2$/day).

A549 NSCLC tumors were established in nude mice and used an identical treatment protocol to that described in FIG. 22A. The data (FIG. 22B) demonstrate that p110$^{RB}$ and p56$^{RB}$ protein therapy has no effect on the growth of the A549 tumors, indicating that tumor growth is reduced only for RB$^{neg}$ tumors.

While localized, subcutaneous therapy is useful for demonstrating the ability of RB protein to reduce tumorigenicity of lung cancer lines in vivo, systemic therapy is a more rigorous test of the potential therapeutic value of p110$^{RB}$. Accordingly, intravenous administration was used to deliver multiple doses of either active or inactive p110$^{RB}$ to Balb/C nude mice bearing subcutaneous NCl-H596 human lung tumors described above. The data (FIG. 23) demonstrate that systemically delivered p110$^{RB}$ effectively blocks tumor growth in a dose dependent fashion. Average tumor size on day 49 was significantly smaller for mice treated with 200 µg/dose of active p110$^{RB}$ than for animals treated with the same dose of inactive p110$^{RB}$ (p<0.01) or the lower dose (50 µg/dose) of p110$^{RB}$ (p<0.05). The highest rate of tumor growth was observed in mice that received inactive preparations of RB protein (as judged by lack of activity in the in vitro $^3$H-thymidine incorporation assay) or a buffer control. Mice treated with active p110$^{RB}$ showed no signs of toxicity or morbidity during the study.

Previous studies have demonstrated that reintroduction of the RB gene into an RB$_{neg}$ background reverses the tumorigenic phenotype in a variety of cell types as measured by growth in soft agar and subcutaneous tumor formation in nude mice. Introduction of a functional RB gene into RB$^{neg}$ tumor cells results in intracellular production of RB protein (see *Cancer Res.* (1992) 52:1968–1973). The growth inhibition resulting from RB gene replacement can also be observed if $p110^{RB}$ is introduced into tumor cells. This application shows that synchronized Saos2 cells microinjected with either $p110^{RB}$ or $p56^{RB}$ in early G1 undergo growth arrest and are blocked from entering S phase. Because microinjection is time consuming and is not practical for therapy of systemic disease, it as decided to determine if $RB^{neg}$ lines would respond to exogenously added RB protein.

Two NSCLC lines were initially chosen for this study. NCl-H596 does not express detectable levels of $p110^{RB}$ as judged by immunoblotting and ELISA whereas A549 produces normal amounts of $p110^{RB}$ (see *J. Immunol. Meth.* (1994) 169:231–240). The data reported herein clearly demonstrate a meaningful dose-response effect of $p110^{RB}$ on NCl-H596 NSCLC tumor cells in vitro. The growth of the $RB^{pos}$ A549 NSCLC carcinoma line was not suppressed by $p110^{RB}$, indicating a preferential effect of $p110^{RB}$ for cells defective in RB expression. This result also suggests that the growth inhibition observed with NCl-H596 NSCLC is not due to a nonspecific toxic component of our RB protein preparations.

$p110^{RB}$ suppresses the growth of three additional $RB^{neg}$ cell lines. The breast carcinoma line MDA-MB-468 harbors a partial RB gene deletion as well as a point mutation in it p53 gene (see *Mol. Cell Biol.* (1990) 9:1628–1634 and *Oncogene* (1993) 8:279–288). Introduction of a single-copy of the RB gene into MDA-MB-468 using retroviral vectors results in decreased tumorigenicity in nude mice and reduced ability to grow in soft agar, but the growth rate in culture was not affected. In the experiments shown herein, exogenous $p110^{RB}$ suppressed the growth of MDA-MB-468. The extent of growth suppression of MDA-MB-468 in vitro may be a function of the higher intracellular level of $p110^{RB}$ that was achieved in these experiments.

While 5637 and MDA-MB-468 cell lines produce no detectable RB protein, the SCLC line NCl H-69 produces an aberrantly migrating species of RB when analyzed by SDS-polyacrylamide gel electrophoresis (*Proc. Natl. Acad. Sci. USA* (1990) 87:2775–2779). A genomic point mutation in NCl H-69 causes abnormal precursor mRNA splicing, resulting in mRNA in which exon 21 is fused in frame to exon 23, eliminating 38 amino acids of the exon 22 coding sequence. The RB protein produced in these cells migrates with an apparent molecular weight of ~4 kD less than $p110^{RB}$ and is defective for E1A and SV-40 T-antigen binding. Reintroduction of wild-type $p110^{RB}$ into NCl H-69 therefore creates a situation in which both functional wild-type and non-functional mutant RB protein coexist. The presence of mutant RB in NCl H-69 does not appear to interfere with growth suppression by wild-type $p110^{RB}$ in this assay system.

The RB-mediated growth suppression in these experiments is specific for $RB^{neg}$ cell lines. Normal bladder, foreskin fibroblast, lung epithelium lines and an $RB^{pos}$ NSCLC line are not growth inhibited by $p110^{RB}$. Under normal culture conditions, overexpression of $p110^{RB}$ does not affect the growth rate of NIH-3T3 fibroblast cells (*Exp. Cell Res.* (1993) 207:99–106). These data are in direct contrast to another report that overexpression of wild-type $p110^{RB}$ leads to growth arrest in normal cells (*Oncogene* (1993) 8:2659–2672). In that study, lung epithelial lines such as WI-38 were growth arrested by transfection with a plasmid overexpressing RB cDNA and subsequent selection of stable transfectants. The inability to see growth suppression of normal cell lines is most likely due to limitations on the intracellular concentration of $p110^{RB}$ that can be achieved by our method. The uptake of radiolabeled $p_{110}$RB revealed that only a small fraction (0.5–1% of cpm added) of the $^{125}$I-$p110^{RB}$ was taken up by the cells.

Studies with microinjected RB protein in synchronized cells have shown that there is a significant delay between the time the protein is injected and the time at which growth suppression can be observed (*Cell* (1991) 67:293–302). The time course of $p110^{RB}$-mediated growth suppression (FIG. 21B) also reflects this delay. These data agree with the time-dependent nuclear localization of $^{125}$I-$p110^{RB}$ seen in FIG. 21B. The nuclear localization of exogenously added $p110^{RB}$ is consistent with reports of the requirement that $p110^{RB}$ be localized to the nucleus in order to have growth suppression activity (*Mol. Cell. Biol.* (1993) 13:4588–4599).

RB protein is an important regulator of cellular proliferation. The work presented herein presents a practical way of restoring normal RB function to $RB^{neg}$ tumors, without the need for genetic modification. This is significant, because loss of RB function occurs in a wide variety of tumor types. The growth suppression of a variety of $RB^{neg}$ tumor cells in vitro demonstrates that exogenous RB protein can functionally substitute for endogenous wild-type RB. While normal cells can take up $p110^{RB}$, they are not growth inhibited, demonstrating that $p110^{RB}$ has selective anti-proliferative activity against $RB^{neg}$ tumor cells. Since reduced tumorigenicity in vivo is a more sensitive indicator of the restoration of tumor suppression function, the experiments included nude mouse xenograft models. Recent observations indicate that reintroduction of the RB gene into $RB^{neg}$ SCLC cells carrying additional multiple genetic alterations suppresses their tumorigenicity in nude mice (*Oncogene* (1993) 8:2175–2181). Therefore, it is reasonable to expect that peptide sequences in the antennapedia homeobox peptide govern its cellular uptake by the neuronal cellular adhesion molecule (N-CAM) and its subsequent nuclear localization (*J. Cell Science* (1992) 102:717–722).

The growth suppression of a variety of $RB^{neg}$ tumor cells in vitro demonstrates that exogenous RB protein can functionally substitute for endogenous wild-type RB. While normal cells can take up $p110^{RB}$, they are not growth inhibited, suggesting that $p110^{RB}$ has selective anti-proliferative activity against $RB^{neg}$ tumor cells. Since reduced tumorigenicity in vivo is a more sensitive indicator of the restoration of tumor suppression function, the experiments included nude mouse xenograft models.

What is claimed is:

1. A method of treating pathologically proliferating cells lacking endogenous functional retinoblastoma protein, the method comprising contacting the proliferating cells with an effective amount of a retinoblastoma polypeptide comprising a C-terminal retinoblastoma polypeptide, the polypeptide having a molecular weight of about 56 kD, whereby cellular proliferation is inhibited.

2. The method of claim 1, wherein the retinoblastoma polypeptide is unphosphorylated.

3. The method of claim 1, wherein the retinoblastoma polypeptide is recombinantly expressed.

4. The method of claim 3, wherein the retinoblastoma polypeptide is expressed in *E. coli*.

5. The method of claim 3, wherein the retinoblastoma polypeptide is expressed by insect cells.

6. The method of claim 1, wherein the retinoblastoma polypeptide is pRB$^{56}$.

7. The method of claim 1, wherein the proliferating cells are cancer cells.

8. The method of claim 7, wherein the cancer cells are associated with retinoblastoma, osteosarcoma, breast cancer, small cell lung cancer, or fibrosarcoma.

9. The method of claim 1, wherein the proliferating cells lack retinoblastoma protein.

10. The method of claim 1, wherein the proliferating cells have a mutated retinoblastoma protein.

11. The method of claim 1, wherein the cellular proliferation is inhibited by cell death.

12. The method of claim 1, wherein the cellular proliferation is inhibited by suppression of a neoplastic phenotype.

13. The method of claim 1, wherein the step of contacting is carried out by administering to a patient an effective amount of the retinoblastoma protein.

14. The method of claim 13, wherein the retinoblastoma polypeptide is administered intravenously.

15. A method of treating pathologically proliferating cells lacking endogenous functional retinoblastoma protein, the method comprising contacting the proliferating cells with an effective amount of a C-terminal retinoblastoma polypeptide having a molecular weight of about 56 kD, whereby cellular proliferation is inhibited.

16. The method of claim 15, wherein the retinoblastoma polypeptide is pRB$^{56}$.

17. A pharmaceutical composition comprising a therapeutically effective amount of a retinoblastoma polypeptide and a pharmacologically suitable carrier, wherein the retinoblastoma polypeptide comprises a C-terminal retinoblastoma polypeptide, the polypeptide having a molecular weight of about 56 kD.

18. The composition of claim 17, wherein the retinoblastoma polypeptide is unphosphorylated.

19. The composition of claim 17, wherein the retinoblastoma polypeptide is recombinantly expressed.

20. The composition of claim 19, wherein the retinoblastoma polypeptide is expressed in *E. coli*.

21. The composition of claim 19, wherein the retinoblastoma polypeptide is expressed by insect cells.

22. The method of claim 17, wherein the retinoblastoma polypeptide is pRB$^{56}$.

23. A pharmaceutical composition comprising a therapeutically effective amount of a C-terminal retinoblastoma polypeptide having a molecular weight of about 56 kD and a pharmacologically suitable carrier.

24. The composition of claim 23, wherein the retinoblastoma polypeptide is pRB$^{56}$.

* * * * *